US012582480B2

(12) United States Patent
Roh et al.

(10) Patent No.: US 12,582,480 B2
(45) Date of Patent: Mar. 24, 2026

(54) DIGITAL IMAGE ANALYSIS FOR ROBOTIC INSTALLATION OF SURGICAL IMPLANTS

(71) Applicant: IX Innovation LLC, Seattle, WA (US)

(72) Inventors: Jeffrey Roh, Seattle, WA (US); Justin Esterberg, Mesa, AZ (US); John Cronin, Jericho, VT (US); Seth Cronin, Essex Junction, VT (US); Michael John Baker, Georgia, VT (US)

(73) Assignee: IX Innovation LLC, Seattle, WA (US)

( * ) Notice: Subject to any disclaimer, the term of this patent is extended or adjusted under 35 U.S.C. 154(b) by 133 days.

(21) Appl. No.: 18/516,482

(22) Filed: Nov. 21, 2023

(65) Prior Publication Data

US 2024/0156538 A1 May 16, 2024

Related U.S. Application Data

(63) Continuation-in-part of application No. 18/150,546, filed on Jan. 5, 2023, now Pat. No. 11,844,575, which
(Continued)

(51) Int. Cl.
*G06F 17/00* (2019.01)
*A61B 34/10* (2016.01)
(Continued)

(52) U.S. Cl.
CPC .............. *A61B 34/10* (2016.02); *A61B 34/37* (2016.02); *B25J 9/1671* (2013.01); *G06T 7/11* (2017.01);
(Continued)

(58) Field of Classification Search
CPC ... A61B 34/10; A61B 34/37; A61B 2034/102; A61B 2034/105; A61B 2034/107;
(Continued)

(56) References Cited

U.S. PATENT DOCUMENTS 9,820,818 B2   11/2017   Malackowski et al.
9,848,778 B2   12/2017   Soykan et al.
(Continued)

FOREIGN PATENT DOCUMENTS

WO   WO-2019245848 A1 * 12/2019 ........... A61B 17/142

OTHER PUBLICATIONS

Image-Guided Robotic Dental Implantation With Natural-Root Formed Implants (Year: 2012).*

*Primary Examiner* — Ronnie M Mancho
(74) *Attorney, Agent, or Firm* — Perkins Coie LLP

(57) ABSTRACT

Computer-implemented digital image analysis methods, apparatuses, and systems for robotic installation of surgical implants are disclosed. A disclosed apparatus plans a route within an anatomy of a patient from an incision site to a surgical implant site for robotic installation of a surgical implant. The apparatus uses digital imaging data to identify less-invasive installation paths and determine the dimensions of the surgical implant components being used. The apparatus segments the surgical implant into surgical implant subcomponents and modifies the surgical implant subcomponents, such that they can be inserted using the identified less-invasive installation paths.

20 Claims, 22 Drawing Sheets

Related U.S. Application Data is a continuation of application No. 17/879,979, filed on Aug. 3, 2022, now Pat. No. 11,547,486.

(51) Int. Cl.
   *A61B 34/37*     (2016.01)
   *B25J 9/16*     (2006.01)
   *G06T 7/11*     (2017.01)

(52) U.S. Cl.
   CPC ... *A61B 2034/102* (2016.02); *A61B 2034/105* (2016.02); *A61B 2034/107* (2016.02); *A61B 2034/108* (2016.02); *G06T 2207/30052* (2013.01)

(58) Field of Classification Search
   CPC ...... A61B 2034/108; A61B 2034/2055; A61B 34/30; B25J 9/1671; B25J 9/1689; G06T 7/11; G06T 2207/30052; G05B 2219/45119
   USPC ........................................................ 700/246
   See application file for complete search history.

(56) References Cited

U.S. PATENT DOCUMENTS

| | | | |
|---|---|---|---|
| 10,105,168 B2 | 10/2018 | Blau | |
| 10,426,560 B2 | 10/2019 | Bowling et al. | |
| 10,806,517 B2 | 10/2020 | Bonny et al. | |
| 10,987,175 B2 | 4/2021 | Britton et al. | |
| 10,987,176 B2 | 4/2021 | Poltaretskyi et al. | |
| 11,045,958 B2 | 6/2021 | Bowling et al. | |
| 11,160,580 B2 | 11/2021 | Hua | |
| 11,179,210 B2 | 11/2021 | Bowling et al. | |
| 11,298,244 B2 | 4/2022 | Schultz et al. | |
| 11,304,760 B1 | 4/2022 | Roh et al. | |
| 11,432,828 B1 | 9/2022 | Lang | |
| 11,439,469 B2 | 9/2022 | Poltaretskyi et al. | |
| 11,471,232 B2 | 10/2022 | Bowling et al. | |
| 11,478,310 B2 | 10/2022 | Poltaretskyi et al. | |
| 11,547,486 B1 | 1/2023 | Roh et al. | |
| 11,571,266 B1 * | 2/2023 | Roh | A61B 90/98 |
| 11,645,531 B2 * | 5/2023 | Moore | H04N 13/122 |
| | | | 345/419 |
| 2016/0242931 A1 | 8/2016 | Wong et al. | |
| 2018/0098704 A1 | 4/2018 | Soykan et al. | |
| 2019/0380792 A1 | 12/2019 | Poltaretskyi et al. | |
| 2020/0306011 A1 | 10/2020 | Chekhonin et al. | |
| 2020/0405148 A1 | 12/2020 | Tran | |
| 2021/0085220 A1 | 3/2021 | Poltaretskyi et al. | |
| 2021/0093329 A1 | 4/2021 | Poltaretskyi et al. | |
| 2021/0093389 A1 | 4/2021 | Poltaretskyi et al. | |
| 2021/0093391 A1 | 4/2021 | Poltaretskyi et al. | |
| 2021/0093395 A1 | 4/2021 | Chaoui et al. | |
| 2021/0093410 A1 | 4/2021 | Gaborit et al. | |
| 2021/0093414 A1 * | 4/2021 | Moore | G06F 30/10 |
| 2021/0097880 A1 | 4/2021 | Kuester et al. | |
| 2021/0097886 A1 | 4/2021 | Kuester et al. | |
| 2021/0104325 A1 | 4/2021 | Chaoui et al. | |
| 2021/0186614 A1 | 6/2021 | Forstein et al. | |
| 2021/0282858 A1 | 9/2021 | Hill et al. | |
| 2021/0308872 A1 | 10/2021 | Bowling et al. | |
| 2021/0391058 A1 | 12/2021 | Kostrzewski et al. | |
| 2022/0248955 A1 | 8/2022 | Tran | |
| 2022/0273450 A1 | 9/2022 | Steines et al. | |
| 2022/0338886 A1 | 10/2022 | Bonny et al. | |
| 2023/0023440 A1 | 1/2023 | Casey et al. | |
| 2023/0181258 A1 * | 6/2023 | Roh | A61B 90/37 |
| | | | 606/1 |
| 2023/0270562 A1 * | 8/2023 | Roh | G16H 30/40 |
| | | | 606/1 |
| 2024/0156538 A1 * | 5/2024 | Roh | A61B 34/10 |

* cited by examiner

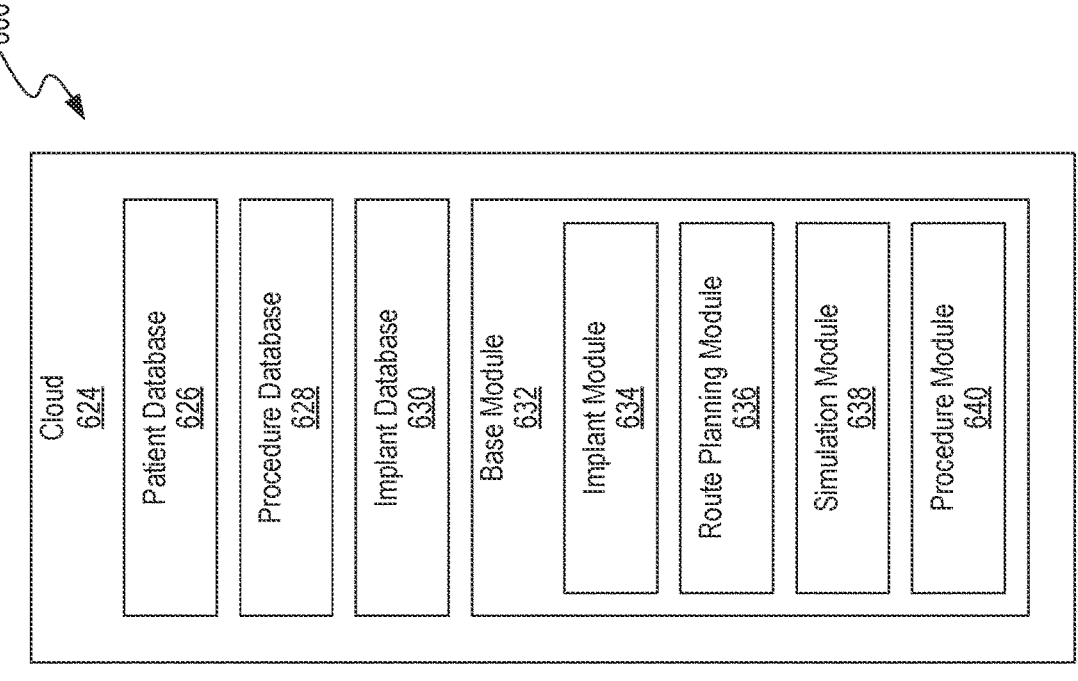
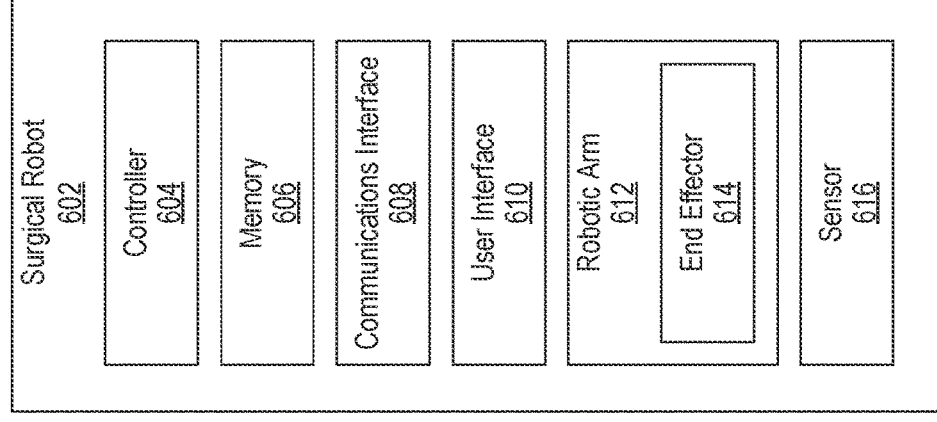
*FIG. 6*

| Patient ID | Age | Gender | Height (in.) | Allergies | Conditions | Image Files |
|---|---|---|---|---|---|---|
| M_0026 | 46 | Male | 70 | None | None | MRI_pelvis_3-20-2022 |
| F_0165 | 36 | Female | 65 | None | None | XRAY_r-knee_2-4-2022 |
| F_0654 | 48 | Female | 68 | Latex | Breast Cancer | CT_chest_1-5-2022 |
| M_0264 | 65 | Male | 72 | None | Coronary Heart Disease | CT_chest_2-16-2022 |
| F_0544 | 72 | Female | 63 | None | Osteoporosis | XRAY_pelvis_2-25-2022 |

*FIG. 7*

| Procedure ID | Patient ID | Surgeon ID | Procedure |
|---|---|---|---|
| 465463 | M_0026 | 1654 | Pelvis reconstruction |
| 847324 | F_0165 | 1548 | Knee replacement |
| 321698 | F_0654 | 1265 | Mastectomy and breast reconstruction |
| 765864 | M_0264 | 1874 | Triple bypass |
| 679465 | F_0544 | 1324 | Hip fracture repair |

*FIG. 8*

| Implant ID | Implant Component ID | Materials | Mechanisms | Width (cm) | Height (cm) | Length (cm) |
|---|---|---|---|---|---|---|
| A364 | 135 | Titanium Alloy | Butterfly hinges | 1.5 | 1 | 6 |
| A364 | 136 | Polypropylene | None | 2 | 1 | 3 |
| A364 | 137 | Cobalt-chromium Alloy | None | 1 | 2.5 | 5 |
| A364 | 138 | Medical-grade Silicone | None | 2 | 2 | 10 |
| A364 | 139 | Polyvinylchloride | None | 1 | 2 | 4 |
| A364 | 140 | Polyethylene | None | 1 | 2 | 4.5 |
| A364 | 141 | Polypropylene | None | 3 | 1.5 | 7 |
| A364 | 142 | Stainless Steel | Expanding mesh | 1 | 1 | 5 |
| A364 | 143 | Titanium | Telescoping tubing | 0.5 | 0.5 | 5 |
| A364 | 144 | Zirconia | None | 1.5 | 1.5 | 3 |

*FIG. 9*

Tibia

Fibula

Calcaneal tendon

Calcaneus

Superior extensor retinaculum

Inferior extensor retinaculum

Extensor digitorum longus tendons

1610

DIGITAL IMAGE ANALYSIS FOR ROBOTIC INSTALLATION OF SURGICAL IMPLANTS

CROSS-REFERENCE TO RELATED APPLICATIONS

The application is a continuation-in-part of U.S. patent application Ser. No. 18/150,546, filed Jan. 5, 2023, which is a continuation of U.S. patent application Ser. No. 17/879, 979, filed Aug. 3, 2022, now U.S. Pat. No. 11,547,486, which are incorporated herein by reference in their entireties.

TECHNICAL FIELD

The present disclosure is generally related to digital image analysis for automated and robotic surgical procedures.

BACKGROUND

More than 200 million surgeries are performed worldwide each year, and recent reports reveal that adverse event rates for surgical conditions remain unacceptably high, despite traditional patient safety initiatives. Adverse events resulting from surgical interventions can be related to errors occurring before or after the procedure, as well as technical surgical errors during the operation. For example, adverse events can occur due to (i) a breakdown in communication within and among the surgical team, care providers, patients, and their families; (ii) delays in diagnosis or failure to diagnose; and (iii) delays in treatment or failure to treat. The risk of complications during surgery can include anesthesia complications, hemorrhaging, high blood pressure, a rise or fall in body temperature, etc. Such adverse events can further occur due to medical errors, infections, underlying physical or health conditions of the patient, reactions to anesthetics or other drugs, etc. Conventional methods for preventing wrong-site, wrong-person, wrong-procedure errors, or retained foreign objects are typically based on communication between the patient, the surgeon(s), and other members of the health care team. However, conventional methods are typically insufficient to prevent surgical errors and adverse events during surgery.

BRIEF DESCRIPTION OF THE DRAWINGS

FIG. 6 is a block diagram illustrating an example robotic surgical system, in accordance with one or more embodiments.

FIG. 7 illustrates a structure of an example database for performing route planning for robotic surgical implant installation, in accordance with one or more embodiments.

FIG. 8 illustrates a structure of an example database for performing route planning for robotic surgical implant installation, in accordance with one or more embodiments.

FIG. 9 illustrates a structure of an example database for performing route planning for robotic surgical implant installation, in accordance with one or more embodiments.

DETAILED DESCRIPTION

Figure 1:
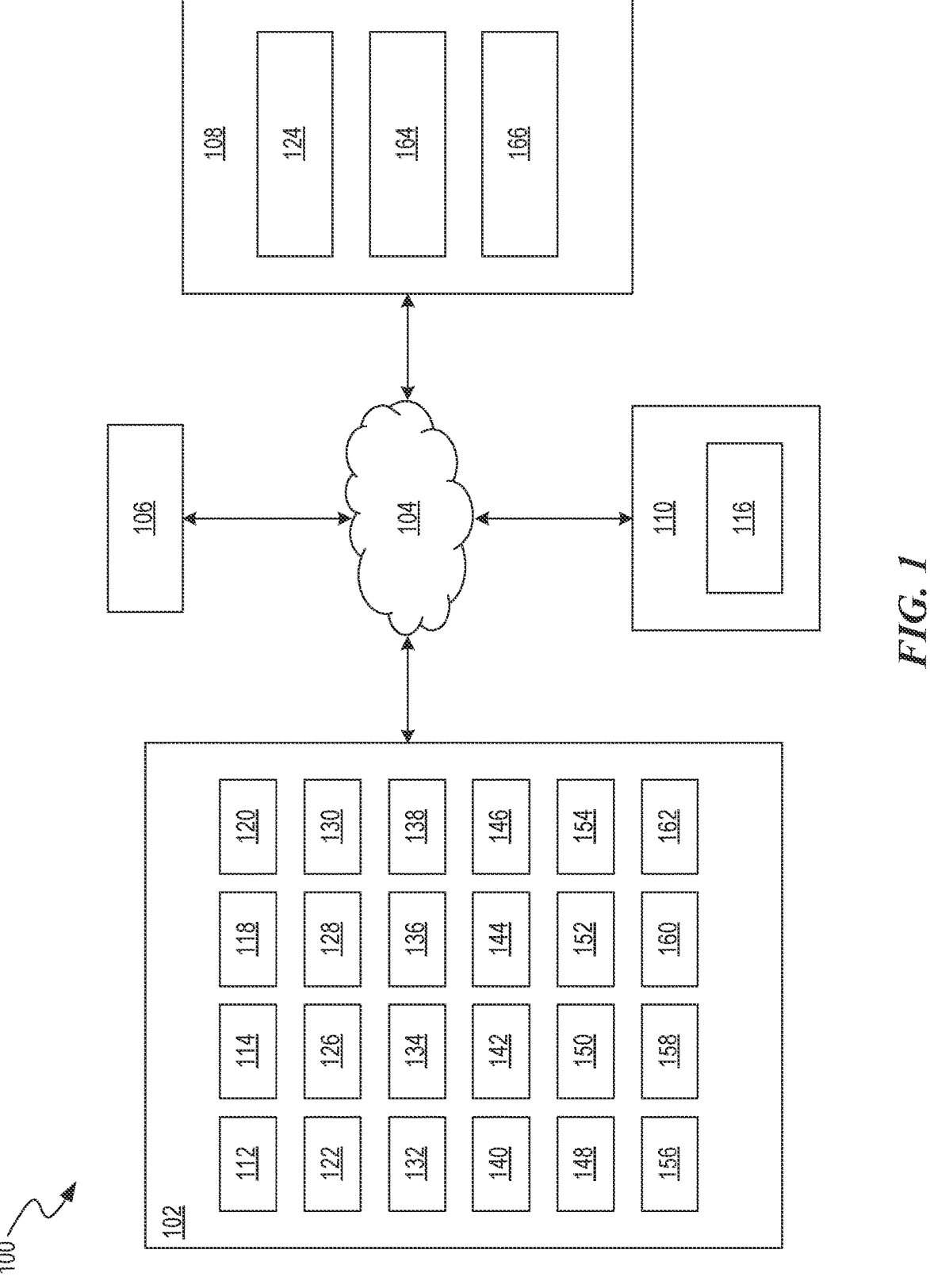
FIG. 1 is a block diagram illustrating an example surgical system, in accordance with one or more embodiments.

Embodiments of the present disclosure will be described more thoroughly from now on with reference to the accompanying drawings. Like numerals represent like elements throughout the several figures, and in which example embodiments are shown. However, embodiments of the claims can be embodied in many different forms and should not be construed as limited to the embodiments set forth herein. The examples set forth herein are non-limiting examples and are merely examples, among other possible examples. Throughout this specification, plural instances (e.g., "610") can implement components, operations, or structures (e.g., "610a") described as a single instance. Further, plural instances (e.g., "610") refer collectively to a set of components, operations, or structures (e.g., "610a") described as a single instance. The description of a single component (e.g., "610a") applies equally to a like-numbered component (e.g., "610b") unless indicated otherwise. These and other aspects, features, and implementations can be expressed as methods, apparatuses, systems, components, program products, means or steps for performing a function, and in other ways. These and other aspects, features, and implementations will become apparent from the following descriptions, including the claims.

The embodiments disclosed herein provide computer-implemented digital image analysis methods for robotic installation of surgical implants. The embodiments enable the visualization and maneuvering of surgical implants within a patient's body for minimally invasive surgery. Traditional surgery methods can sometimes result in unintended harm to a patient because of the difficulty or inability to visualize a surgical tool's movements within the patient's body. For example, traditional laparoscopic procedures typically use rigid tool extensions to maneuver within a patient's body that can limit movement and cause internal injury to the patient. For traditional surgical methods to access a desired surgical site within or on a patient's body, success requires not only proper location of the incisions but also sufficient space to maneuver tools into required positions and orientations.

Further, the disclosed embodiments herein describe methods, apparatuses, and systems for route planning for robotic surgical implant installation. The disclosed apparatus plans a route within a patient's body from an incision site to a surgical implant site to enable the installation of a surgical implant within the patient's body. The disclosed system uses imaging data to identify a less-invasive installation path, and determines the dimensions of the surgical implant components being used. The system segments the surgical implant into surgical implant subcomponents, and modifies the surgical implant subcomponents, such that they can be inserted using the identified less invasive installation path.

In some embodiments, a method of determining a route for installing an artificial structure (e.g., a surgical implant or a surgical implant component) in a patient's body using minimally invasive techniques includes imaging the patient's body to obtain at least one image of the patient. A surgical implant is segmented into multiple implant components. An incision site and an implant site in the patient's body are identified. At least two separate routes are identified between the incision site and the implant site for the implant components to pass through. Based on the identified routes, the system determines at least one surgical movement modality for the surgical implant segments. Movement of the implant components using the at least one surgical movement modality through the identified routes is simulated. The system identifies at least one route through which at least one surgical implant component can be navigated from the incision site to the implant site using the surgical movement modality.

The advantages and benefits of the methods, systems, and apparatuses disclosed herein include compatibility with best practice guidelines for performing surgery in an operating room, e.g., from regulatory bodies and professional standards organizations such as the Association for Surgical Technologists. The systems for route planning for robotic surgical implant installation disclosed use computer networks, the Internet, intranets, and supporting technologies to implement a cost-effective technology to collect, transmit, store, analyze, and use information in electronic formats. The disclosed embodiments especially facilitate the robotic installation of surgical implants without requiring larger incisions in the patient's body, thus improving healing and recovery times.

The disclosed methods enable the installation and assembly of surgical implants using implant components, e.g., metal rods, plates, or screws. The modularity provided by the embodiments improves a surgical robot's flexibility in managing the variability in physiology between patients. Further, the disclosed apparatuses enable treatment of a wider range of physiological defects. The disclosed surgical systems use the modularity and design of surgical implant components to reduce the impact on the patient to improve recovery times. Moreover, the disclosed embodiments reduce injury to the patient's body by reducing incision sizes and preventing internal injury while navigating through the patient's body during installation of a surgical implant. Thus, patient recovery times are improved. The disclosed route planning methods to navigate the patient's unique physiology further enables improved procedure times while reducing harm to the patient. The disclosed surgical implant designs when paired with image-based route planning enable minimally invasive implantation of even complex surgical implants. In addition, the advantages of the convolutional neural network (CNN) used for machine learning (ML) in the disclosed embodiments include the obviation of feature extraction and the use of shared weight in convolutional layers, which means that the same filter (weights bank) is used for each node in the layer; this both reduces memory footprint and improves performance.

FIG. 1 is a block diagram illustrating an example surgical system 100, in accordance with one or more embodiments. The system 100 includes various surgical and medical equipment (e.g., a patient monitor 112) located within an operating room 102 or a doctor's office 110, a console 108 for performing surgery or other patient care, and a database 106 for storing electronic health records. The console 108 is the same as or similar to the console 420 illustrated and described in more detail with reference to FIG. 4A. The system 100 is implemented using the components of the example computer system 300 illustrated and described in more detail with reference to FIG. 3. Likewise, embodiments of the system 100 can include different and/or additional components or can be connected in different ways.

The operating room 102 is a facility, e.g., within a hospital, where surgical operations are carried out in an aseptic environment. Proper surgical procedures require a sterile field. In some embodiments, the sterile field is maintained in the operating room 102 in a medical care facility such as a hospital, the doctor's office 110, or an outpatient surgery center.

In some embodiments, the system 100 includes one or more medical or surgical patient monitors 112. The monitors 112 can include a vital signs monitor (a medical diagnostic instrument), which can be a portable, battery-powered, multi-parametric, vital signs monitoring device used for both ambulatory and transport applications as well as bedside monitoring. The vital signs monitor can be used with an isolated data link to an interconnected portable computer or the console 108, allowing snapshot and trended data from the vital signs monitor to be printed automatically at the console 108, and also allowing default configuration settings to be downloaded to the vital signs monitor. The vital signs monitor is capable of use as a stand-alone unit as well as part of a bi-directional wireless communications network that includes at least one remote monitoring station (e.g., the console 108). The vital signs monitor can measure multiple physiological parameters of a patient wherein various sensor output signals are transmitted either wirelessly or by means of a wired connection to at least one remote site, such as the console 108.

In some embodiments, the monitors 112 include a heart rate monitor, which is a sensor and/or a sensor system applied in the context of monitoring heart rates. The heart rate monitor measures, directly or indirectly, any physiological condition from which any relevant aspect of heart rate can be gleaned. For example, some embodiments of the heart rate monitor measure different or overlapping physiological conditions to measure the same aspect of heart rate. Alternatively, some embodiments measure the same, different, or overlapping physiological conditions to measure different aspects of heart rate, e.g., number of beats, strength of beats, regularity of beats, beat anomalies, etc.

In some embodiments, the monitors 112 include a pulse oximeter or SpO2 monitor, which is a plethysmograph or any instrument that measures variations in the size of an organ or body part of the patient on the basis of the amount of blood passing through or present in the body part. The pulse oximeter is a type of plethysmograph that determines the oxygen saturation of the blood by indirectly measuring the oxygen saturation of the patient's blood (as opposed to measuring oxygen saturation directly through a blood sample) and changes in blood volume in the skin. The pulse oximeter can include a light sensor that is placed at a site on the patient, usually a fingertip, toe, forehead, or earlobe, or in the case of a neonate, across a foot. Light, which can be produced by a light source integrated into the pulse oximeter, containing both red and infrared wavelengths, is directed onto the skin of the patient, and the light that passes through the skin is detected by the pulse oximeter. The intensity of light in each wavelength is measured by the pulse oximeter over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths when a pulse occurs, it is possible to determine blood oxygen saturation of hemoglobin in arterial blood. This relies on the observation that highly oxygenated blood will relatively absorb more red light and less infrared light than blood with a lower oxygen saturation.

In some embodiments, the monitors 112 include an end-tidal CO2 monitor or capnography monitor used for measurement of the level of carbon dioxide that is released at the end of an exhaled breath (referred to as end-tidal carbon dioxide, ETCO2). An end-tidal CO2 monitor or capnography monitor is widely used in anesthesia and intensive care. ETCO2 can be calculated by plotting expiratory CO2 with time. Further, ETCO2 monitors are important for the measurement of applications such as cardiopulmonary resuscitation (CPR), airway assessment, procedural sedation and analgesia, pulmonary diseases such as obstructive pulmonary disease, pulmonary embolism, etc., heart failure, metabolic disorders, etc. The end-tidal CO2 monitor can be configured as side stream (diverting) or mainstream (non-diverting). A diverting end-tidal CO2 monitor transports a portion of a patient's respired gases from the sampling site to the end-tidal CO2 monitor, while a non-diverting end-tidal CO2 monitor does not transport gas away. Also, measurement by the end-tidal CO2 monitor is based on the absorption of infrared light by carbon dioxide where exhaled gas passes through a sampling chamber containing an infrared light source and photodetector on both sides. Based on the amount of infrared light reaching the photodetector, the amount of carbon dioxide present in the gas can be determined.

In some embodiments, the monitors 112 include a blood pressure monitor that measures blood pressure, particularly in arteries. The blood pressure monitor uses a non-invasive technique (by external cuff application) or an invasive technique (by a cannula needle inserted in an artery, used in the operating room 102) for measurement. The non-invasive method (referred to as a sphygmomanometer) works by measurement of force exerted against arterial walls during (i) ventricular systole (i.e., systolic blood pressure occurs when the heart beats and pushes blood through the arteries) and (ii) ventricular diastole (i.e., diastolic blood pressure occurs when the heart rests and is filling with blood) thereby measuring systole and diastole, respectively. The blood pressure monitor can be of three types: automatic/digital, manual (aneroid-dial), and manual (mercury-column). The sphygmomanometer can include a bladder, a cuff, a pressure meter, a stethoscope, a valve, and a bulb. The cuff inflates until it fits tightly around the patient's arm, cutting off the blood flow, and then the valve opens to deflate it. The blood pressure monitor operates by inflating a cuff tightly around the arm; as the cuff reaches the systolic pressure, blood begins to flow in the artery, creating a vibration, which is detected by the blood pressure monitor, which records the systolic pressure. The techniques used for measurement can be auscultatory or oscillometric.

In some embodiments, the monitors 112 include a body temperature monitor. The body temperature monitor measures the temperature invasively or non-invasively by placement of a sensor into organs such as the bladder, rectum, esophagus, tympanum, etc., and mouth, armpit, etc., respectively. The body temperature monitor is of two types: contact and non-contact. Temperature can be measured in two forms: core temperature and peripheral temperature. Temperature measurement can be done by thermocouples, resistive temperature devices (RTDs, thermistors), infrared radiators, bimetallic devices, liquid expansion devices, molecular change-of-state, and silicon diodes. A body temperature monitor commonly used for the measurement of temperature includes a temperature sensing element (e.g., temperature sensor) and a means for converting to a numerical value.

In some embodiments, the monitors 112 measure respiration rate or breathing rate—the rate at which breathing occurs—and which is measured by the number of breaths the patient takes per minute. The rate is measured when a person is at rest and simply involves counting the number of breaths for one minute by counting how many times the chest rises. Normal respiration rates for an adult patient at rest are in the range: 12 to 16 breaths per minute. A variation can be an indication of an abnormality/medical condition or the patient's demographic parameters. The monitors 112 can indicate hypoxia, a condition with low levels of oxygen in the cells, or hypercapnia, a condition in which high levels of carbon dioxide are in the bloodstream. Pulmonary disorders, asthma, anxiety, pneumonia, heart diseases, dehydration, and drug overdose are some abnormal conditions, which can cause a change to the respiration rate, thereby increasing or reducing the respiration rate from normal levels.

In some embodiments, the monitors 112 measure an electrocardiogram (EKG or ECG), a representation of the electrical activity of the heart (graphical trace of voltage versus time) by placement of electrodes on the skin/body surface. The electrodes capture the electrical impulse, which travels through the heart causing systole and diastole or the pumping of the heart. This impulse provides information related to the normal functioning of the heart and the production of impulses. A change can occur due to medical conditions such as arrhythmias (tachycardia, where the heart rate becomes faster, and bradycardia, where the heart rate becomes slower), coronary heart disease, heart attacks, or cardiomyopathy. The instrument used for measurement of the electrocardiogram is called an electrocardiograph, which measures the electrical impulses by the placement of electrodes on the surface of the body and represents the ECG by a PQRST waveform. A PQRST wave is read as: P wave, which represents the depolarization of the left and right atrium and corresponds to atrial contraction; QRS complex, which indicates ventricular depolarization and represents the electrical impulse as it spreads through the ventricles; and T wave, which indicates ventricular repolarization and follows the QRS complex.

In some embodiments, the monitors 112 perform neuromonitoring, also called intraoperative neurophysiological monitoring (IONM). For example, the monitors 112 assess functions and changes in the brain, brainstem, spinal cord, cranial nerves, and peripheral nerves during a surgical procedure on these organs. Monitoring includes both continuous monitoring of neural tissue as well as the localization of vital neural structures. IONM measures changes in these organs where the changes are indicative of irreversible damage or injuries in the organs, aiming at reducing the risk of neurological deficits after operations involving the nervous system. Monitoring is effective in localization of anatomical structures, including peripheral nerves and the sensorimotor cortex, which helps in guiding a surgical robot during dissection. Electrophysiological modalities employed in neuromonitoring are an extracellular single unit and local field recordings (LFP), somatosensory evoked potential (SSEP), transcranial electrical motor evoked potentials (TCeMEP), electromyography (EMG), electroencephalography (EEG), and auditory brainstem response (ABR). The use of neurophysiological monitoring during surgical procedures requires anesthesia techniques to avoid interference and signal alteration due to anesthesia.

In some embodiments, the monitors 112 measure motor evoked potential (MEP), electrical signals that are recorded from descending motor pathways or muscles following stimulation of motor pathways within the brain. MEP is determined by measurement of the action potential elicited by non-invasive stimulation of the motor cortex through the scalp. MEP is for intraoperative monitoring and neurophysiological testing of the motor pathways specifically during spinal procedures. The technique of monitoring for measurement of MEP is defined based on parameters, such as a site of stimulation (motor cortex or spinal cord), method of stimulation (electrical potential or magnetic field), and site of recording (spinal cord or peripheral mixed nerve and muscle). The target site is stimulated by the use of electrical or magnetic means.

In some embodiments, the monitors 112 measure somatosensory evoked potential (SSEP or SEP): the electrical signals generated by the brain and the spinal cord in response to sensory stimulus or touch. SSEP is used for intraoperative neurophysiological monitoring in spinal surgeries. The measurements are reliable, which allows for continuous monitoring during a surgical procedure. The sensor stimulus commonly given to the organs can be auditory, visual, or somatosensory SEPs and applied on the skin, peripheral nerves of the upper limbs, lower limbs, or scalp. The stimulation technique can be mechanical, electrical (provides larger and more robust responses), or intraoperative spinal monitoring modality.

In some embodiments, the monitors 112 provide electromyography (EMG): the evaluation and recording of electrical signals or electrical activity of the skeletal muscles. An electromyography instrument, electromyograph, or electromyogram for the measurement of the EMG activity records electrical activity produced by skeletal muscles and evaluates the functional integrity of individual nerves. The nerves monitored by an EMG instrument can be intracranial, spinal, or peripheral nerves. The electrodes used for the acquisition of signals can be invasive or non-invasive electrodes. The technique used for measurement can be spontaneous or triggered. Spontaneous EMG refers to the recording of myoelectric signals such as compression, stretching, or pulling of nerves during surgical manipulation. Spontaneous EMG is recorded by the insertion of a needle electrode. Triggered EMG refers to the recording of myoelectric signals during stimulation of a target site such as a pedicle screw with incremental current intensities.

In some embodiments, the monitors 112 provide electroencephalography (EEG), measuring the electrical signals in the brain. Brain cells communicate with each other through electrical impulses. EEG can be used to help detect potential problems associated with this activity. An electroencephalograph is used for the measurement of EEG activity. Electrodes ranging from 8 to 16 pairs are attached to the scalp, where each pair of electrodes transmits a signal to one or more recording channels. EEG is a modality for intraoperative neurophysiological monitoring and assessing cortical perfusion and oxygenation during a variety of vascular, cardiac, and neurosurgical procedures. The waves produced by EEG are alpha, beta, theta, and delta.

In some embodiments, the monitors 112 include sensors, such as microphones or optical sensors, that produce images or video captured from at least one of multiple imaging devices, for example, cameras attached to manipulators or end effectors, cameras mounted to the ceiling or other surface above the surgical theater, or cameras mounted on a tripod or other independent mounting device. In some embodiments, the cameras are body worn by a surgical robot or other surgical staff, cameras are incorporated into a wearable device, such as an augmented reality device like Google Glass™, or cameras are integrated into an endoscopic, microscopic, or laparoscopic device. In some embodiments, a camera or other imaging device (e.g., ultrasound) present in the operating room 102 is associated with one or more areas in the operating room 102. The sensors can be associated with measuring a specific parameter of the patient, such as respiratory rate, blood pressure, blood oxygen level, heart rate, etc.

In some embodiments, the system 100 includes a medical visualization apparatus 114 used for visualization and analysis of objects (preferably two-dimensional (2D) or three-dimensional (3D) objects) in the operating room 102. The medical visualization apparatus 114 provides the selection of points at surfaces, selection of a region of interest, or selection of objects. The medical visualization apparatus 114 can also be used for diagnosis, treatment planning, intraoperative support, documentation, or educational purposes. The medical visualization apparatus 114 can further include microscopes, endoscopes/arthroscopes/laparoscopes, fiber optics, surgical lights, high-definition monitors, operating room cameras, etc. Two-dimensional (2D) or three-dimensional (3D) visualization software provides visual representations of scanned body parts via virtual models, offering significant depth and nuance to static two-dimensional medical images. The software facilitates improved diagnoses, narrowed surgical operation learning curves, reduced operational costs, and shortened image acquisition times.

In some embodiments, the system 100 includes an instrument 118 such as an endoscope, arthroscope, or laparoscope for minimally invasive surgery (MIS), in which procedures are performed by cutting a minimal incision in the body. An endoscope refers to an instrument used to visualize, diagnose, and treat problems inside hollow organs where the instrument is inserted through natural body openings such as the mouth or anus. An endoscope can perform a procedure as follows: a scope with a tiny camera attached to a long, thin tube is inserted. A surgical robot moves it through a body passageway or opening to see inside an organ. It can be used for diagnosis and surgery (such as for removing polyps from the colon). An arthroscope refers to an instrument used to visualize, diagnose, and treat problems inside a joint by a TV camera inserted through small portals/incisions and to perform procedures on cartilage, ligaments, tendons, etc. An arthroscope can perform the procedure as follows: a surgical robot makes a small incision in a patient's skin and inserts a pencil-sized instrument with a small lens and lighting system to magnify the target site (joint) and viewing of the interior of the joint by means of a miniature TV camera and then performs the procedure. A laparoscope refers to an instrument used to visualize, diagnose, and treat problems inside soft organs like the abdomen and pelvis by a TV camera inserted through small portals/incisions and to perform procedures.

In some embodiments, the system 100 includes fiber optics 120, which refer to flexible, transparent fiber made by drawing glass (silica) or plastic to a diameter slightly thicker than that of a human hair. Fiber optics 120 are arranged in bundles called optical cables and used to transmit light signals across long distances. Fiber optics 120 are used most often as a means to transmit light between the two ends of the fiber and find wide usage in the medical field. Traditional surgery requires sizable and invasive incisions to expose internal organs and operate on affected areas, but with fiber optics 120 much smaller surgical incisions can be performed. Fiber optics 120 contain components such as a core, cladding, and buffer coating. Fiber optics 120 can be inserted in hypodermic needles and catheters, endoscopes, operation theater tools, ophthalmological tools, and dentistry tools. Fiber optic sensors include a light source, optical fiber, external transducer, and photodetector. Fiber optic sensors can be intrinsic or extrinsic. Fiber optic sensors can be categorized into four types: physical, imaging, chemical, and biological.

In some embodiments, the system 100 includes surgical lights 122 (referred to as operating lights) that perform illumination of a local area or cavity of the patient. Surgical lights 122 play an important role in illumination before, during, and after a medical procedure. Surgical lights 122 can be categorized by lamp type as conventional (incandescent) and LED (light-emitting diode). Surgical lights 122 can be categorized by mounting configuration as ceiling-mounted, wall-mounted, or floor stand. Surgical lights 122 can be categorized by type as tungsten, quartz, xenon halogens, and/or LEDs. Surgical lights 122 include sterilizable handles, which allow a surgical robot to adjust light positions. Some important factors affecting surgical lights 122 can be illumination, shadow management (cast shadows and contour shadows), the volume of light, heat management, or fail-safe surgical lighting.

In some embodiments, the system 100 includes a surgical tower 128, e.g., used in conjunction with the robotic surgical system 160 disclosed herein, for MIS. The surgical tower 128 includes instruments used for performing MIS or surgery, which is performed by creating small incisions in the body. The instruments are also referred to as minimally invasive devices or minimally invasive access devices. The procedure of performing MIS can also be referred to as a minimally invasive procedure. MIS is a safer, less invasive, and more precise surgical procedure. Some medical procedures where the surgical tower 128 is useful and widely used are procedures for lung, gynecological, head and neck, heart, and urological conditions. MIS can be robotic or non-robotic/endoscopic. MIS can include endoscopic, laparoscopic, arthroscopic, natural orifice intraluminal, and natural orifice transluminal procedures. A surgical tower access device can also be designed as an outer sleeve and an inner sleeve that telescopingly or slidably engage with one another. When a telescope is used to operate on the abdomen, the procedure is called laparoscopy. The surgical tower 128 typically includes access to a variety of surgical tools, such as for electrocautery, radiofrequency, lasers, sensors, etc.

In some embodiments, radiofrequency (RF) is used in association with MIS devices. The RF can be used for the treatment of skin by delivering it to the skin through a minimally invasive surgical tool (e.g., fine needles), which does not require skin excision. The RF can be used for real-time tracking of MIS devices such as laparoscopic instruments. The RF can provide radiofrequency ablation to a patient suffering from atrial fibrillation through smaller incisions made between the ribs. The RF can be used to perform an endoscopic surgery on the body such as the spine by delivery of RF energy.

In some embodiments, the system 100 includes an instrument 130 to perform electrocautery for burning a part of the body to remove or close off a part of it. Various physiological conditions or surgical procedures require the removal of body tissues and organs, a consequence of which is bleeding. In order to achieve hemostasis and for removing and sealing all blood vessels that are supplied to an organ after surgical incision, the electrocautery instrument 130 can be used. For example, after removing part of the liver for removal of a tumor, etc., blood vessels in the liver must be sealed individually. The electrocautery instrument 130 can be used for sealing living tissue such as arteries, veins, lymph nodes, nerves, fats, ligaments, and other soft tissue structures. The electrocautery instrument 130 can be used in applications such as surgery, tumor removal, nasal treatment, or wart removal. Electrocautery can operate in two modes, monopolar or bipolar. The electrocautery instrument 130 can consist of a generator, a handpiece, and one or more electrodes.

In some embodiments, the system 100 includes a laser 132 used in association with MIS devices. The laser 132 can be used in MIS with an endoscope. The laser 132 is attached to the distal end of the endoscope and steered at high speed by producing higher incision quality than with existing surgical tools thereby minimizing damage to surrounding tissue. The laser 132 can be used to perform MIS using a laparoscope in the lower and upper gastrointestinal tract, eye, nose, and throat. The laser 132 is used in MIS to ablate soft tissues, such as a herniated spinal disc bulge.

In some embodiments, sensors 134 are used in association with MIS devices and the robotic surgical system 160 described herein. The sensors 134 can be used in MIS for tactile sensing of surgical tool-tissue interaction forces. During MIS, the field of view and workspace of surgical tools are compromised due to the indirect access to the anatomy and lack of surgeon's hand-eye coordination. The sensors 134 provide a tactile sensation to the surgeon by providing information regarding shape, stiffness, and texture of organ or tissue (different characteristics) to the surgeon's hands through a sense of touch. This detects a tumor through palpation, which exhibits a "tougher" feel than that of healthy soft tissue, pulse felt from blood vessels, and abnormal lesions. The sensors 134 can output shape, size, pressure, softness, composition, temperature, vibration, shear, and normal forces. The sensors 134 can be electrical or optical, consisting of capacitive, inductive, piezoelectric, piezoresistive, magnetic, and auditory. The sensors 134 can be used in robotic or laparoscopic surgery, palpation, biopsy, heart ablation, and valvuloplasty.

In some embodiments, the system 100 includes an imaging system 136 (instruments are used for the creation of images and visualization of the interior of a human body for diagnostic and treatment purposes). The imaging system 136 is used in different medical settings and can help in the screening of health conditions, diagnosing causes of symptoms, or monitoring of health conditions. The imaging system 136 can include various imaging techniques such as X-ray, fluoroscopy, magnetic resonance imaging (MRI), ultrasound, endoscopy, elastography, tactile imaging, thermography, medical photography, and nuclear medicine, e.g., positron emission tomography (PET). Some factors which can drive the market are cost and clinical advantages of medical imaging modalities, a rising share of ageing populations, increasing prevalence of cardiovascular or lifestyle diseases, and increasing demand from emerging economies.

In some embodiments, the imaging system 136 includes X-ray medical imaging instruments that use X-ray radiation (i.e., X-ray range in the electromagnetic radiation spectrum) for the creation of images of the interior of the human body for diagnostic and treatment purposes. An X-ray instrument is also referred to as an X-ray generator. It is a non-invasive instrument based on different absorption of X-rays by tissues based on their radiological density (radiological density is different for bones and soft tissues). For the creation of an image by the X-ray instrument, X-rays produced by an X-ray tube are passed through a patient positioned to the detector. As the X-rays pass through the body, images appear in shades of black and white, depending on the type and densities of tissue the X-rays pass through. Some of the applications where X-rays are used can be bone fractures, infections, calcification, tumors, arthritis, blood vessel blockages, digestive problems, or heart problems. The X-ray instrument can consist of components such as an X-ray tube, operating console, collimator, grid, detector, radiographic film, etc.

In some embodiments, the imaging system 136 includes MRI medical imaging instruments that use powerful magnets for the creation of images of the interior of the human body for diagnostic and treatment purposes. Some of the applications where MRI can be used are brain/spinal cord anomalies, tumors in the body, breast cancer screening, joint injuries, uterine/pelvic pain detection, or heart problems. For the creation of the image by an MRI instrument, magnetic resonance is produced by powerful magnets, which produce a strong magnetic field that forces protons in the body to align with that field. When a radiofrequency current is then pulsed through the patient, the protons are stimulated, and spin out of equilibrium, straining against the pull of the magnetic field. Turning off the radiofrequency field allows detection of energy released by realignment of protons with the magnetic field by MRI sensors. The time taken by the protons for realignment with the magnetic field and energy release is dependent on environmental factors and the chemical nature of the molecules. MRI is more widely suitable for imaging of non-bony parts or soft tissues of the body. MRI can be less harmful as it does not use damaging ionizing radiation as in the X-ray instrument. MRI instruments can consist of magnets, gradients, radiofrequency systems, or computer control systems. Some areas where imaging by MRI should be prohibited can be people with implants.

In some embodiments, the imaging system 136 uses computed tomography imaging (CT) that uses an X-ray radiation (i.e., X-ray range in the electromagnetic radiation spectrum) for the creation of cross-sectional images of the interior of the human body. CT refers to a computerized X-ray imaging procedure in which a narrow beam of X-rays is aimed at a patient and quickly rotated around the body, producing signals that are processed by the machine's computer to generate cross-sectional images—or "slices"—of the body. A CT instrument is different from an X-ray instrument as it creates 3-dimensional cross-sectional images of the body while the X-ray instrument creates 2-dimensional images of the body; the 3-dimensional cross-sectional images are created by taking images from different angles, which is done by taking a series of tomographic images from different angles. The diverse images are collected by a computer and digitally stacked to form a 3-dimensional image of the patient. For creation of images by the CT instrument, a CT scanner uses a motorized X-ray source that rotates around the circular opening of a donut-shaped structure called a gantry while the X-ray tube rotates around the patient shooting narrow beams of X-rays through the body. Some of the applications where CT can be used can be blood clots; bone fractures, including subtle fractures not visible on X-ray; or organ injuries.

In some embodiments, the imaging system 136 includes ultrasound imaging, also referred to as sonography or ultrasonography, that uses ultrasound or sound waves (also referred to as acoustic waves) for the creation of cross-sectional images of the interior of the human body. Ultrasound waves in the imaging system 136 can be produced by a piezoelectric transducer, which produces sound waves and sends them into the body. The sound waves that are reflected are converted into electrical signals, which are sent to an ultrasound scanner. Ultrasound instruments can be used for diagnostic and functional imaging or for therapeutic or interventional procedures. Some of the applications where ultrasound can be used are diagnosis/treatment/guidance during medical procedures (e.g., biopsies, internal organs such as liver/kidneys/pancreas, fetal monitoring, etc.), in soft tissues, muscles, blood vessels, tendons, or joints. Ultrasound can be used for internal imaging (where the transducer is placed in organs, e.g., vagina) and external imaging (where the transducer is placed on the chest for heart monitoring or the abdomen for fetal monitoring). An ultrasound machine can consist of a monitor, keyboard, processor, data storage, probe, and transducer.

In some embodiments, the system 100 includes a stereotactic navigation system 138 that uses patient imaging (e.g., CT, MRI) to guide surgical robots in the placement of specialized surgical instruments and implants. The patient images are taken to guide a surgical robot before or during the medical procedure. The stereotactic navigation system 138 includes a camera having infrared sensors to determine the location of the tip of the probe being used in the surgical procedure. This information is sent in real-time so that the surgical robot has a clear image of the precise location where it is working in the body. The stereotactic navigation system 138 can be framed (requires attachment of a frame to the patient's head using screws or pins) or frameless (does not require the placement of a frame on the patient's anatomy). The stereotactic navigation system 138 can be used for diagnostic biopsies, tumor resection, bone preparation/implant placement, placement of electrodes, otolaryngologic procedures, or neurosurgical procedures.

In some embodiments, the system 100 includes an anesthesiology machine 140 that is used to generate and mix medical gases, such as oxygen or air, and anesthetic agents to induce and maintain anesthesia in patients. The anesthesiology machine 140 delivers oxygen and anesthetic gas to the patient and filters out expiratory carbon dioxide. The anesthesiology machine 140 can perform functions such as providing oxygen (O2), accurately mixing anesthetic gases and vapors, enabling patient ventilation, and minimizing anesthesia-related risks to patients and staff. The anesthesiology machine 140 can include the following essential components: a source of O2, O2 flowmeter, vaporizer (anesthetics include isoflurane, halothane, enflurane, desflurane, sevoflurane, and methoxyflurane), patient breathing circuit (tubing, connectors, and valves), and scavenging system (removes any excess anesthetics gases). The anesthesiology machine 140 can be divided into three parts: the high pressure system, the intermediate pressure system, and the low pressure system. The process of anesthesia starts with oxygen flow from a pipeline or cylinder through the flowmeter; the O2 flows through the vaporizer and picks up the anesthetic vapors; the O2-anesthetic mix then flows through the breathing circuit and into the patient's lungs, usually by spontaneous ventilation or normal respiration.

In some embodiments, the system 100 includes a surgical bed 142 equipped with mechanisms that can elevate or lower the entire bed platform; flex, or extend individual components of the platform; or raise or lower the head or the feet of the patient independently. The surgical bed 142 can be an operation bed, cardiac bed, amputation bed, or fracture bed. Some essential components of the surgical bed 142 can be a bed sheet, woolen blanket, bath towel, and bed block. The surgical bed 142 can also be referred to as a post-operative bed, which refers to a special type of bed made for the patient who is coming from the operation theater or from another procedure that requires anesthesia. The surgical bed 142 is designed in a manner that makes it easier to transfer an unconscious or weak patient from a stretcher/wheelchair to the bed. The surgical bed 142 should protect bed linen from vomiting, bleeding, drainage, and discharge; provide warmth and comfort to the patient to prevent shock; provide necessary positions, which are suitable for operation; protect patient from being chilled; and be prepared to meet any emergency.

In some embodiments, the system 100 includes a Jackson frame 144 (or Jackson table), which refers to a frame or table that is designed for use in spinal surgeries and can be used in a variety of spinal procedures in supine, prone, or lateral positions in a safe manner. Two peculiar features of the Jackson table 144 are the absence of central table support and an ability to rotate the table through 180 degrees. The Jackson table 144 is supported at both ends, which keeps the whole of the table free. This allows the visualization of a patient's trunk and major parts of extremities as well. The Jackson frame 144 allows the patient to be slid from the cart onto the table in the supine position with appropriate padding placed. The patient is then strapped securely on the Jackson table 144.

In some embodiments, the system 100 includes a disposable air warmer 146 (sometimes referred to as a Bair™ or Bair Hugger™). The disposable air warmer 146 is a convective temperature management system used in a hospital or surgery center to maintain a patient's core body temperature. The disposable air warmer 146 includes a reusable warming unit and a single-use disposable warming blanket for use during surgery. It can also be used before and after surgery. The disposable air warmer 146 uses convective warming consisting of two components: a warming unit and a disposable blanket. The disposable air warmer 146 filters air and then forces warm air through disposable blankets, which cover the patient. The blanket can be designed to use pressure points on the patient's body to prevent heat from reaching areas at risk for pressure sores or burns. The blanket can also include drainage holes where fluid passes through the surface of the blanket to linen underneath, which will reduce the risk of skin softening and reduce the risk of unintended cooling because of heat loss from evaporation.

In some embodiments, the system 100 includes a sequential compression device (SCD) 148 used to help prevent blood clots in the deep veins of legs. The sequential compression device 148 uses cuffs around the legs that fill with air and squeeze the legs. This increases blood flow through the veins of the legs and helps prevent blood clots. A deep vein thrombosis (DVT) is a blood clot that forms in a vein deep inside the body. Some of the risks of using the SCD 148 can be discomfort, warmth, sweating beneath the cuff, skin breakdown, nerve damage, or pressure injury.

In some embodiments, the system 100 includes a bed position controller 150, which refers to an instrument for controlling the position of the patient bed. Positioning a patient in bed is important for maintaining alignment and for preventing bedsores (pressure ulcers), foot drop, and contractures. Proper positioning is also vital for providing comfort for patients who are bedridden or have decreased mobility related to a medical condition or treatment. When positioning a patient in bed, supportive devices such as pillows, rolls, and blankets, along with repositioning, can aid in providing comfort and safety. The patient can be in the following positions in a bed: supine position, prone position, lateral position, Sims' position, Fowler's position, semi-Fowler's position, orthopedic or tripod position, or Trendelenburg position.

In some embodiments, the system 100 includes environmental controls 152. The environmental controls 152 can be operating room environmental controls for control or maintenance of the environment in the operating room 102 where procedures are performed to minimize the risk of airborne infection and to provide a conducive environment for everyone in the operating room 102 (e.g., surgeon, anesthesiologist, nurses, and patient). Some factors that can contribute to poor quality in the environment of the operating room 102 are temperature, ventilation, and humidity, and those conditions can lead to profound effects on the health and work productivity of people in the operating room 102. As an example: surgeons prefer a cool, dry climate since they work under bright, hot lights; anesthesia personnel prefer a warmer, less breezy climate; patient condition demands a relatively warm, humid, and quiet environment. The operating room environmental controls can control the environment by taking care of the following factors: environmental humidity, infection control, or odor control. Humidity control can be performed by controlling the temperature of anesthesia gases; infection can be controlled by the use of filters to purify the air.

In some embodiments, the environmental controls 152 include a heating, ventilation, and air conditioning (HVAC) system for regulating the environment of indoor settings by moving air between indoor and outdoor areas, along with heating and cooling. HVAC can use a different combination of systems, machines, and technologies to improve comfort. HVAC can be necessary to maintain the environment of the operating room 102. The operating room 102 can be a traditional operating room (which can have a large diffuser array directly above the operating table) or a hybrid operating room (which can have monitors and imaging equipment 136 that consume valuable ceiling space and complicate the design process). HVAC can include three main units, for example, a heating unit (e.g., furnace or boiler), a ventilation unit (natural or forced), and an air conditioning unit (which can remove existing heat). HVAC can be made of components such as air returns, filters, exhaust outlets, ducts, electrical elements, outdoor units, compressors, coils, and blowers. The HVAC system can use central heating and AC systems that use a single blower to circulate air via internal ducts.

In some embodiments, the environmental controls 152 include an air purification system for removing contaminants from the air in the operating room 102 to improve indoor air quality. Air purification can be important in the operating room 102 as surgical site infection can be a reason for high mortality and morbidity. The air purification system can deliver clean, filtered, contaminant-free air over the surgical bed 142 using a diffuser, airflow, etc., to remove all infectious particles down and away from the patient. The air purification system can be an air curtain, multi-diffuser array, or single large diffuser (based on laminar diffuser flow) or High-Efficiency Particulate Air filter (HEPA filter). A HEPA filter protects a patient from infection and contamination using a filter, which is mounted at the terminal of the duct. A HEPA filter can be mounted on the ceiling and deliver clean, filtered air in a flow to the operating room 102 that provides a sweeping effect that pushes contaminants out via the return grilles that are usually mounted on the lower wall.

In some embodiments, the system 100 includes one or more medical or surgical tools 154. The surgical tools 154 can include orthopedic tools (also referred to as orthopedic instruments) used for treatment and prevention of deformities and injuries of the musculoskeletal system or skeleton, articulations, and locomotive system (i.e., set formed by skeleton, muscles attached to it, and the part of the nervous system that controls the muscles). A major percentage of orthopedic tools are made of plastic. The orthopedic tools can be divided into the following specialties: hand and wrist, foot and ankle, shoulder, and elbow, arthroscopic, hip, and knee. The orthopedic tools can be fixation tools, relieving tools, corrective tools, or compression-distraction tools. A fixation tool refers to a tool designed to restrict movements partially or completely in a joint, e.g., hinged splints (for preserving a certain range of movement in a joint) or rigid splints. A relieving tool refers to a tool designed to relieve pressure on an ailing part by transferring support to healthy parts of an extremity, e.g., Thomas splint and the Voskoboinikova apparatus. A corrective tool refers to a surgical tool designed to gradually correct a deformity, e.g., corsets, splints, orthopedic footwear, insoles, and other devices to correct abnormal positions of the foot. A compression-distraction tool refers to a surgical tool designed to correct acquired or congenital deformities of the extremities, e.g., curvature, shortening, and pseudarthrosis such as Gudushauri. A fixation tool can be an internal fixation tool (e.g., screws, plates) or external fixation tools used to correct a radius or tibia fracture. The orthopedic tools can be bone-holding forceps, drill bits, nail pins, hammers, staples, etc.

In some embodiments, the surgical tools 154 include a drill for making holes in bones for insertion of implants like nails, plates, screws, and wires. The drill tool functions by drilling cylindrical tunnels into bone. Drills can be used in orthopedics for performing medical procedures. If the drill does not stop immediately when used, the use of the drill on bones can have some risks, such as harm caused to bone, muscle, nerves, and venous tissues, which are wrapped by surrounding tissue. Drills vary widely in speed, power, and size. Drills can be powered as electrical, pneumatic, or battery. Drills generally can work on speeds below 1000 rpm in orthopedic settings. Temperature control of drills is an important aspect in the functioning of the drill and is dependent on parameters such as rotation speed, torque, orthotropic site, sharpness of the cutting edges, irrigation, and cooling systems. The drill can include a physical drill, power cord, electronically motorized bone drill, or rotating bone shearing incision work unit.

In some embodiments, the surgical tools 154 include a scalpel for slicing, cutting, or osteotomy of bone during orthopedic procedure. The scalpel can be designed to provide clean cuts through osseous structures with minimal loss of viable bone while sparing adjacent elastic soft tissues largely unaffected while performing a slicing procedure. This is suited for spine applications where bone must be cut adjacent to the dura and neural structures. The scalpel does not rotate but performs cutting by an ultrasonically oscillating or forward/backward moving metal tip. Scalpels can prevent injuries caused by a drill in a spinal surgery such as complications such as nerve thermal injury, grasping soft tissue, tearing dura mater, and mechanical injury.

In some embodiments, stitches (also referred to as sutures) or a sterile, surgical thread is used to repair cuts or lacerations and is used to close incisions or hold body tissues together after a surgery or an injury. Stitches can involve the use of a needle along with an attached thread. Stitches can be either absorbable (the stitches automatically break down harmlessly in the body over time without intervention) or non-absorbable (the stitches do not automatically break down over time and must be manually removed if not left indefinitely). Stitches can be based on material monofilament, multifilament, and barb. Stitches can be classified based on size. Stitches can be based on synthetic or natural material. Stitches can be coated or un-coated.

In some embodiments, the surgical tools 154 include a stapler used for fragment fixation when inter-fragmental screw fixation is not easy. When there is vast damage and a bone is broken into fragments, staples can be used between these fragments for internal fixation and bone reconstruction. For example, they can be used around joints in ankle and foot surgeries, in cases of soft tissue damage, or to attach tendons or ligaments to the bone for reconstruction surgery. Staplers can be made of surgical grade stainless steel or titanium, and they are thicker, stronger, and larger.

In some embodiments, other medical or surgical equipment, such as a set of articles, surgical tools, or objects, is used to implement or achieve an operation or activity. A medical equipment refers to an article, instrument, apparatus, or machine used for diagnosis, prevention, or treatment of a medical condition or disease, or to the detection, measurement, restoration, correction, or modification of structure/function of the body for some health purpose. The medical equipment can perform functions invasively or non-invasively. In some embodiments, the medical equipment includes components such as a sensor/transducer, a signal conditioner, a display, or a data storage unit, etc. In some embodiments, the medical equipment includes a sensor to receive a signal from instruments measuring a patient's body, a transducer for converting one form of energy to electrical energy, a signal conditioner such as an amplifier, filter, etc., to convert the output from the transducer into an electrical value, a display to provide a visual representation of the measured parameter or quantity, or a storage system to store data, which can be used for future reference. A medical equipment can perform diagnosis or provide therapy; for example, the equipment delivers air into the lungs of a patient who is physically unable to breathe, or breathes insufficiently, and moves it out of the lungs.

In some embodiments, the system includes a machine 156 to aid in breathing. The machine 156 can be a ventilator (also referred to as a respirator) that provides a patient with oxygen when they are unable to breathe on their own. A ventilator is required when a person is not able to breathe on their own. A ventilator can perform a function of gently pushing air into the lungs and allow it to come back out. The ventilator functions by delivery of positive pressure to force air into the lungs, while usual breathing uses negative pressure by the opening of the mouth, and air flows in. The ventilator can be required during surgery or after surgery. The ventilator can be required in case of respiratory failure due to acute respiratory distress syndrome, head injury, asthma, lung diseases, drug overdose, neonatal respiratory distress syndrome, pneumonia, sepsis, spinal cord injury, cardiac arrest, etc., or during surgery. The ventilator can be used with a face mask (non-invasive ventilation, where the ventilation is required for a shorter duration of time) or with a breathing tube also referred to as an endotracheal tube (invasive ventilation, where the ventilation is required for a longer duration of time). Ventilator use can have some risks such as infections, fluid build-up, muscle weakness, lung damage, etc. The ventilator can be operated in various modes, such as assist-control ventilation (ACV), synchronized intermittent-mandatory ventilation (SIMV), pressure-controlled ventilation (PCV), pressure support ventilation (PSV), pressure-controlled inverse ratio ventilation (PCIRV), airway pressure release ventilation (APRV), etc. The ventilator can include a gas delivery system, power source, control system, safety feature, gas filter, and monitor.

In some embodiments, the machine 156 is a continuous positive airway pressure (CPAP) used for the treatment of sleep apnea disorder in a patient. Sleep apnea refers to a disorder in which breathing repeatedly stops and starts while a patient is sleeping, often because throat/airways briefly collapse or something temporarily blocks them. Sleep apnea can lead to serious health problems, such as high blood pressure and heart trouble. A CPAP instrument helps the patient with sleep apnea to breathe more easily during sleep by sending a steady flow of oxygen into the nose and mouth during sleep, which keeps the airways open and helps the patient to breathe normally. The CPAP machine can work by a compressor/motor, which generates a continuous stream of pressurized air that travels through an air filter into a flexible tube. The tube delivers purified air into a mask sealed around the nose/mouth of the patient. The airstream from the instrument pushes against any blockages, opening the airways so lungs receive plenty of oxygen, and breathing does not stop as nothing obstructs oxygen. This helps the patient to not wake up to resume breathing. CPAP can have a nasal pillow mask, nasal mask, or full mask. A CPAP instrument can include a motor, a cushioned mask, a tube that connects the motor to the mask, a headgear frame, and adjustable straps. The essential components can be a motor, a cushioned mask, and a tube that connects the motor to the mask.

In some embodiments, the system 100 includes surgical supplies, consumables 158, or necessary supplies for the system 100 to provide care within the hospital or surgical environment. The consumables 158 can include gloves, gowns, masks, syringes, needles, sutures, staples, tubing, catheters, or adhesives for wound dressing, in addition to other surgical tools needed by surgical robots, doctors, and nurses to provide care. Depending on the device, mechanical testing can be carried out in tensile, compression, or flexure; in dynamic or fatigue; via impact; or with the application of torsion. The consumables 158 can be disposable (e.g., time-saving, have no risk of healthcare-associated infections, and cost-efficient) or sterilizable (to avoid cross-contamination or risk of surgical site infections).

In some embodiments, the system 100 includes a robotic surgical system 160 (sometimes referred to as a medical robotic system or a robotic system) that provides intelligent services and information to the operating room 102 and the console 108 by interacting with the environment, including human beings, via the use of various sensors, actuators, and human interfaces. The robotic surgical system 160 can be employed for automating processes in a wide range of applications, ranging from industrial (manufacturing), domestic, medical, service, military, entertainment, space, etc. The medical robotic system market is segmented by product type into surgical robotic systems, rehabilitative robotic systems, non-invasive radiosurgery robots, and hospital and pharmacy robotic systems. Robotic surgeries can be performed using tele-manipulators (e.g., input devices 166 at the console 108), which use the surgeon's actions on one side to control one or more "effectors" on the other side. The medical robotic system 160 provides precision and can be used for remotely controlled, minimally invasive procedures. The robotic surgical system 160 includes computer-controlled electromechanical devices that work in response to controls (e.g., input devices 166 at the console 108) manipulated by the surgeons.

In some embodiments, the system 100 includes equipment tracking systems 162, such as RFID, which is used to tag an instrument with an electronic tag and tracks it using the tag. Typically, this could involve a centralized platform that provides details such as location, owner, contract, and maintenance history for all equipment in real-time. A variety of techniques can be used to track physical assets, including RFID, global positioning system (GPS), Bluetooth low energy (BLE), barcodes, near-field communication (NFC), Wi-Fi, etc. The equipment tracking system 162 includes hardware components, such as RFID tags, GPS trackers, barcodes, and QR codes. The hardware component is placed on the asset, and it communicates with the software (directly or via a scanner), providing the software with data about the asset's location and properties. In some embodiments, the equipment tracking system 162 uses electromagnetic fields to transmit data from an RFID tag to a reader. Reading of RFID tags can be done by portable or mounted RFID readers. The read range for RFID varies with the frequency used. Managing and locating important assets is a key challenge for tracking medical equipment. Time spent searching for critical equipment can lead to expensive delays or downtime, missed deadlines and customer commitments, and wasted labor. The problem has previously been solved by using barcode labels or manual serial numbers and spreadsheets; however, these require manual labor. The RFID tag can be passive (smaller and less expensive, read ranges are shorter, have no power of their own, and are powered by the radio frequency energy transmitted from RFID readers/antennas) or active (larger and more expensive, read ranges are longer, have a built-in power source and transmitter of their own).

In some embodiments, the system 100 includes medical equipment, computers, software, etc., located in the doctor's office 110 that is communicably coupled to the operating room 102 over the network 104. For example, the medical equipment in the doctor's office 110 can include a micro-scope 116 used for viewing samples and objects that cannot be seen with an unaided eye. The microscope 116 can have components such as eyepieces, objective lenses, adjustment knobs, a stage, an illuminator, a condenser, or a diaphragm. The microscope 116 works by manipulating how light enters the eye using a convex lens, where both sides of the lens are curved outwards. When light reflects off of an object being viewed under the microscope 116 and passes through the lens, it bends toward the eye. This makes the object look bigger than it is. The microscope 116 can be compound (light-illuminated and the image seen with the microscope 116 is two-dimensional), dissection or stereoscope (light-illuminated and the image seen with the microscope 116 is three-dimensional), confocal (laser-illuminated and the image seen with the microscope 116 is on a digital computer screen), scanning electron (SEM) (electron-illuminated and the image seen with the microscope 116 is in black and white), or transmission electron microscope (TEM) (elec-tron-illuminated and the image seen with the microscope 116 is the high magnification and high resolution).

The system 100 includes an electronic health records (EHR) database 106 that contains patient records. The EHR is a digital version of patients' paper charts. The EHR database 106 can contain more information than a traditional patient chart, including, but not limited to, a patient's medical history, diagnoses, medications, treatment plans, allergies, diagnostic imaging, lab results, etc. In some embodiments, the steps for each procedure disclosed herein are stored in the EHR database 106. Electronic health records can also include data collected from the monitors 112 from historical procedures. The EHR database 106 is implemented using components of the example computer system 300 illustrated and described in more detail with reference to FIG. 3.

In some embodiments, the EHR database 106 includes a digital record of patients' health information, collected, and stored systematically over time. The EHR database 106 can include demographics, medical history, history of present illness (HPI), progress notes, problems, medications, vital signs, immunizations, laboratory data, or radiology reports. Software (in memory 164) operating on the console 108 or implemented on the example computer system 300 (e.g., the instructions 304, 308 illustrated and described in more detail with reference to FIG. 3) are used to capture, store, and share patient data in a structured way. The EHR database 106 can be created and managed by authorized providers and can make health information accessible to authorized providers across practices and health organizations, such as laborato-ries, specialists, medical imaging facilities, pharmacies, emergency facilities, etc. The timely availability of EHR data enables healthcare providers to make more accurate decisions and provide better care to the patients by effective diagnosis and reduced medical errors. Besides providing opportunities to enhance patient care, the EHR database 106 can also be used to facilitate clinical research by combining patients' demographics into a large pool. For example, the EHR database 106 can support a wide range of epidemio-logical research on the natural history of disease, drug utilization, and safety, as well as health services research.

The console 108 is a computer device, such as a server, computer, tablet, smartphone, smart speaker, etc., imple-mented using components of the example computer system 300 illustrated and described in more detail with reference to FIG. 3. In some embodiments, the steps for each procedure disclosed herein are stored in memory 164 on the console 108 for execution.

In some embodiments, the operating room 102 or the console 108 includes high-definition monitors 124, which refer to displays in which a clearer picture is possible than with low-definition, low-resolution screens. The high-defi-nition monitors 124 have a higher density of pixels per inch than past standard TV screens. Resolution for the high-definition monitors 124 can be 1280×720 pixels or more (e.g., Full HD, 1920×1080; Quad HD, 2560×1440; 4K, 3840×2160; 8K, 7680×4320 pixels). The high-definition monitor 124 can operate in progressive or interlaced scan-ning mode. High-definition monitors used in medical appli-cations can offer improved visibility; allow for precise and safe surgery with rich color reproduction; provide suitable colors for each clinical discipline; provide better visibility, operability with a large screen and electronic zoom, higher image quality in low light conditions, better visualization of blood vessels and lesions, and high contrast at high spatial frequencies; be twice as sensitive as conventional sensors; and make it easier to determine tissue boundaries (fat, nerves, vessels, etc.).

In some embodiments, the console 108 includes an input interface or one or more input devices 166. The input devices 166 can include a keyboard, a mouse, a joystick, any hand-held controller, or a hand-controlled manipulator, e.g., a tele-manipulator used to perform robotic surgery.

In some embodiments, the console 108, the equipment in the doctor's office 110, and the EHR database 106 are communicatively coupled to the equipment in the operating room 102 by a direct connection, such as ethernet, or wirelessly by the cloud over the network 104. The network 104 is the same as or similar to the network 314 illustrated and described in more detail with reference to FIG. 3. For example, the console 108 can communicate with the robotic surgical system 160 using the network adapter 312 illus-trated and described in more detail with reference to FIG. 3.

In embodiments, the system 100 uses quantum comput-ing. Quantum computing refers to the use of a computational device or method that uses properties of quantum states defined by quantum mechanics such as superposition, entanglement, etc., to perform computations. Quantum devices use qubits, which are the quantum equivalent of bits in a classical computing system. Qubits have at least two quantum states or probable outcomes. These outcomes, combined with a coefficient representing the probability of each outcome, describes the possible states, or bits of data, which can be represented by the qubits according to the principle of quantum superposition. These states can be manipulated to shift the probability of each outcome, or additionally, add additional possible outcomes to perform computations, the final state of which can be measured to achieve the result.

Quantum computing provides significant benefits in the areas of encryption and the simulation of natural systems. Encryption is aided by the uncertain nature of quantum computing in that data is represented by an indeterminate state of probable outcomes, therefore making decryption virtually impossible. The simulation of natural systems, such as chemical and biological interactions, benefit from the fact that the nature of quantum computing is the same as the systems being simulated. In medical fields, quantum com-puting shows the greatest promise for drug discovery and simulating the interaction of drugs with biologic systems, however the same technology can also be used to predict the interaction of a biologic system with an implanted device, preventing rejection of an implant by a patient's body. Quantum computing can be used to investigate long term functioning of an implant. Further, quantum computing can be used to study the reaction of a patient to a surgical procedure, during a simulation, before a procedure, or actively during a procedure.

Figure 2:
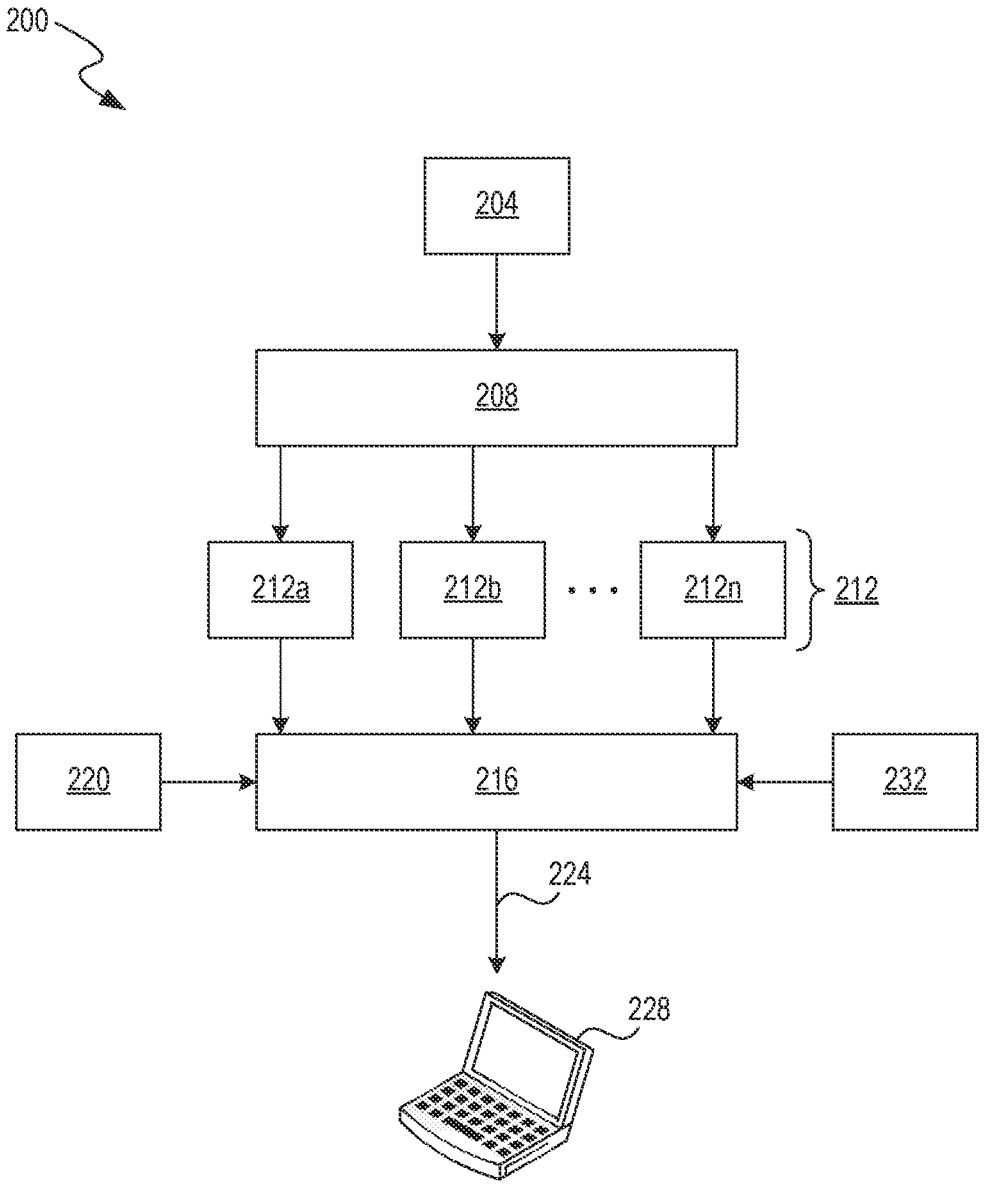
FIG. 2 is a block diagram illustrating an example machine learning (ML) system, in accordance with one or more embodiments.

FIG. 2 is a block diagram illustrating an example machine learning (ML) system 200, in accordance with one or more embodiments. The ML system 200 is implemented using components of the example computer system 300 illustrated and described in more detail with reference to FIG. 3. For example, the ML system 200 can be implemented on the console 108 using instructions programmed in the memory 164 illustrated and described in more detail with reference to FIG. 1. Likewise, embodiments of the ML system 200 can include different and/or additional components or be connected in different ways. The ML system 200 is sometimes referred to as a ML module.

The ML system 200 includes a feature extraction module 208 implemented using components of the example computer system 300 illustrated and described in more detail with reference to FIG. 3. In some embodiments, the feature extraction module 208 extracts a feature vector 212 from input data 204. For example, the input data 204 can include one or more physiological parameters measured by the monitors 112 illustrated and described in more detail with reference to FIG. 1. The feature vector 212 includes features 212a, 212b, . . . , 212n. The feature extraction module 208 reduces the redundancy in the input data 204, e.g., repetitive data values, to transform the input data 204 into the reduced set of features 212, e.g., features 212a, 212b, . . . , 212n. The feature vector 212 contains the relevant information from the input data 204, such that events or data value thresholds of interest can be identified by the ML model 216 by using this reduced representation. In some example embodiments, the following dimensionality reduction techniques are used by the feature extraction module 208: independent component analysis, Isomap, kernel principal component analysis (PCA), latent semantic analysis, partial least squares, PCA, multifactor dimensionality reduction, nonlinear dimensionality reduction, multilinear PCA, multilinear subspace learning, semidefinite embedding, autoencoder, and deep feature synthesis.

In alternate embodiments, the ML model 216 performs deep learning (also known as deep structured learning or hierarchical learning) directly on the input data 204 to learn data representations, as opposed to using task-specific algorithms. In deep learning, no explicit feature extraction is performed; the features 212 are implicitly extracted by the ML system 200. For example, the ML model 216 can use a cascade of multiple layers of nonlinear processing units for implicit feature extraction and transformation. Each successive layer uses the output from the previous layer as input. The ML model 216 can thus learn in supervised (e.g., classification) and/or unsupervised (e.g., pattern analysis) modes. The ML model 216 can learn multiple levels of representations that correspond to different levels of abstraction, wherein the different levels form a hierarchy of concepts. In this manner, the ML model 216 can be configured to differentiate features of interest from background features.

In alternative example embodiments, the ML model 216, e.g., in the form of a CNN generates the output 224, without the need for feature extraction, directly from the input data 204. The output 224 is provided to the computer device 228 or the console 108 illustrated and described in more detail with reference to FIG. 1. The computer device 228 is a server, computer, tablet, smartphone, smart speaker, etc., implemented using components of the example computer system 300 illustrated and described in more detail with reference to FIG. 3. In some embodiments, the steps performed by the ML system 200 are stored in memory on the computer device 228 for execution. In other embodiments, the output 224 is displayed on the high-definition monitors 124 illustrated and described in more detail with reference to FIG. 1.

A CNN is a type of feed-forward artificial neural network in which the connectivity pattern between its neurons is inspired by the organization of a visual cortex. Individual cortical neurons respond to stimuli in a restricted area of space known as the receptive field. The receptive fields of different neurons partially overlap such that they tile the visual field. The response of an individual neuron to stimuli within its receptive field can be approximated mathematically by a convolution operation. CNNs are based on biological processes and are variations of multilayer perceptrons designed to use minimal amounts of preprocessing.

The ML model 216 can be a CNN that includes both convolutional layers and max pooling layers. The architecture of the ML model 216 can be "fully convolutional," which means that variable sized sensor data vectors can be fed into it. For all convolutional layers, the ML model 216 can specify a kernel size, a stride of the convolution, and an amount of zero padding applied to the input of that layer. For the pooling layers, the model 216 can specify the kernel size and stride of the pooling.

In some embodiments, the ML system 200 trains the ML model 216, based on the training data 220, to correlate the feature vector 212 to expected outputs in the training data 220. As part of the training of the ML model 216, the ML system 200 forms a training set of features and training labels by identifying a positive training set of features that have been determined to have a desired property in question, and, in some embodiments, forms a negative training set of features that lack the property in question.

The ML system 200 applies ML techniques to train the ML model 216, that when applied to the feature vector 212, outputs indications of whether the feature vector 212 has an associated desired property or properties, such as a probability that the feature vector 212 has a particular Boolean property, or an estimated value of a scalar property. The ML system 200 can further apply dimensionality reduction (e.g., via linear discriminant analysis (LDA), PCA, or the like) to reduce the amount of data in the feature vector 212 to a smaller, more representative set of data.

The ML system 200 can use supervised ML to train the ML model 216, with feature vectors of the positive training set and the negative training set serving as the inputs. In some embodiments, different ML techniques, such as linear support vector machine (linear SVM), boosting for other algorithms (e.g., AdaBoost), logistic regression, naïve Bayes, memory-based learning, random forests, bagged trees, decision trees, boosted trees, boosted stumps, neural networks, CNNs, etc., are used. In some example embodiments, a validation set 232 is formed of additional features, other than those in the training data 220, which have already been determined to have or to lack the property in question. The ML system 200 applies the trained ML model 216 to the features of the validation set 232 to quantify the accuracy of the ML model 216. Common metrics applied in accuracy measurement include: Precision and Recall, where Precision refers to a number of results the ML model 216 correctly predicted out of the total it predicted, and Recall is a number of results the ML model 216 correctly predicted out of the total number of features that had the desired property in question. In some embodiments, the ML system 200 iteratively re-trains the ML model 216 until the occurrence of a stopping condition, such as the accuracy measurement indication that the ML model 216 is sufficiently accurate, or a number of training rounds having taken place. The validation set 232 can include data corresponding to confirmed anatomical features, tissue states, tissue conditions, diagnoses, or combinations thereof. This allows the detected values to be validated using the validation set 232. The validation set 232 can be generated based on analysis to be performed.

Figure 3:
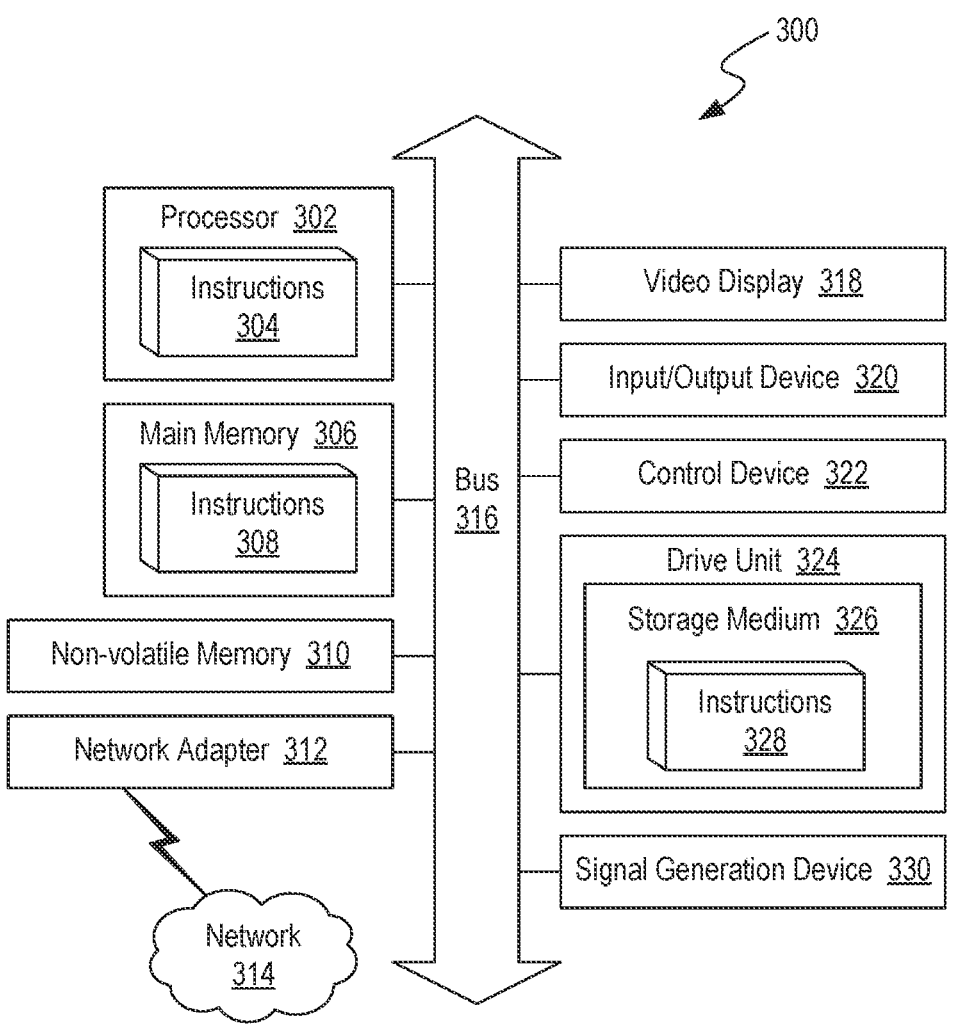
FIG. 3 is a block diagram illustrating an example computer system, in accordance with one or more embodiments.

FIG. 3 is a block diagram illustrating an example computer system, in accordance with one or more embodiments. Components of the example computer system 300 can be used to implement the monitors 112, the console 108, or the EHR database 106 illustrated and described in more detail with reference to FIG. 1. In some embodiments, components of the example computer system 300 are used to implement the ML system 200 illustrated and described in more detail with reference to FIG. 2. At least some operations described herein can be implemented on the computer system 300.

The computer system 300 can include one or more central processing units ("processors") 302, main memory 306, non-volatile memory 310, network adapters 312 (e.g., network interface), video displays 318, input/output devices 320, control devices 322 (e.g., keyboard and pointing devices), drive units 324 including a storage medium 326, and a signal generation device 320 that are communicatively connected to a bus 316. The bus 316 is illustrated as an abstraction that represents one or more physical buses and/or point-to-point connections that are connected by appropriate bridges, adapters, or controllers. The bus 316, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The computer system 300 can share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the computer system 300.

While the main memory 306, non-volatile memory 310, and storage medium 326 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 328. The term "machine-readable medium" and "storage medium" shall also be taken to include any medium that is capable of storing, encoding, or carrying a set of instructions for execution by the computer system 300.

In general, the routines executed to implement the embodiments of the disclosure can be implemented as part of an operating system or a specific application, component, program, object, module, or sequence of instructions (collectively referred to as "computer programs"). The computer programs typically include one or more instructions (e.g., instructions 304, 308, 328) set at various times in various memory and storage devices in a computer device. When read and executed by the one or more processors 302, the instruction(s) cause the computer system 300 to perform operations to execute elements involving the various aspects of the disclosure.

Moreover, while embodiments have been described in the context of fully functioning computer devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 310, floppy and other removable disks, hard disk drives, optical discs (e.g., Compact Disc Read-Only Memory (CD-ROMS), Digital Versatile Discs (DVDs)), and transmission-type media such as digital and analog communication links.

The network adapter 312 enables the computer system 300 to mediate data in a network 314 with an entity that is external to the computer system 300 through any communication protocol supported by the computer system 300 and the external entity. The network adapter 312 can include a network adapter card, a wireless network interface card, a router, an access point, a wireless router, a switch, a multi-layer switch, a protocol converter, a gateway, a bridge, a bridge router, a hub, a digital media receiver, and/or a repeater.

The network adapter 312 can include a firewall that governs and/or manages permission to access proxy data in a computer network and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall can additionally manage and/or have access to an access control list that details permissions including the access and operation rights of an object by an individual, a machine, and/or an application, and the circumstances under which the permission rights stand.

Figure 4A:
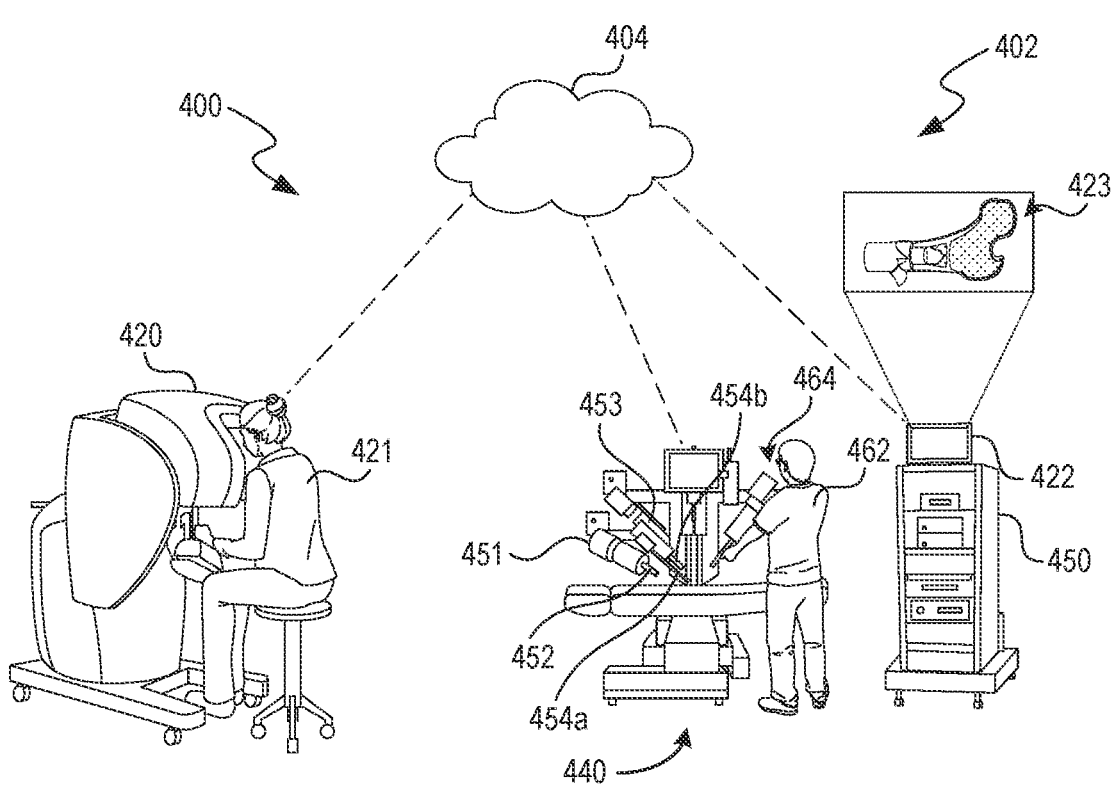
FIG. 4A is a block diagram illustrating an example robotic surgical system, in accordance with one or more embodiments.

FIG. 4A is a block diagram illustrating an example robotic surgical system 400, in accordance with one or more embodiments. The robotic surgical system 400 is the same as or similar to the robotic surgical system 160 illustrated and described in more detail with reference to FIG. 1. The robotic surgical system 400 can include components and features discussed in connection with FIGS. 1-3 and 4B-5. For example, the robotic surgical system 400 can include a console 420 with features of the console 108 of FIG. 1. Likewise, the components and features of FIG. 4A can be included or used with other embodiments disclosed herein. For example, the description of the input devices of FIG. 4A applies equally to other input devices (e.g., input devices 166 of FIG. 1). The robotic surgical system 400 can be configured to provide telepresence control by one or more consultants at remote locations based on a pre-operative surgical plan, inter-operative surgical event(s) at the surgical suite, etc. Machine learning (ML) algorithms and other techniques disclosed herein can be used to manage surgical suite resources, schedule consultants, manage permission rights, and/or adjust network flow to improve surgical outcomes. For example, flow of network traffic at the surgical suite can be controlled to maintain a threshold level of control of the medical equipment by the user. The user is typically a medical professional, e.g., a surgeon, a nurse, a surgeon's assistant, or doctor.

The robotic surgical system 400 includes a user device or console 420 ("console 420"), a surgical robot 440, and a computer or data system 450. The console 420 can be operated by a surgeon and can communicate with components in an operating room 402, remote devices/servers, a network 404, or databases (e.g., database 106 of FIG. 1) via the network 404. The robotic surgical system 400 can include surgical control software and can include a guidance system (e.g., ML guidance system, AI guidance system, etc.), surgical planning software, event detection software, surgical tool software, etc. or other features disclosed herein to perform surgical step(s) or procedures or implement steps of processes discussed herein.

A consultant device 401 can communicate via the network 404 with components of the robotic surgical system 400, monitoring equipment, or other components of the robotic surgical system 400. The surgical robot 440, or other components disclosed herein, can communicate with and send collected data (e.g., sensor readings, instrument data, surgical robot data, etc.) to at least one database or data system 450, which are accessible to the consultant(s). This information can be used to, for example, create new ML training data sets, generate procedure plans, perform future simulations, post-operatively analyze surgical procedures, or the like. The controller or data system 450 can be incorporated, used with, or otherwise interact with other databases, systems, and components disclosed herein. In some embodiments, the data system 450 can be incorporated into the surgical robot 440 or other systems disclosed herein. In some embodiments, the data system 450 can be located at a remote location and can communicate with a surgical robot via one or more networks. For example, the data system 450 can communicate with a hospital via a network, such as a wide area network, a cellular network, etc. One or more local networks at the hospital can establish communication channels between pieces of surgical equipment within the surgical room. A mobile network test module may measure the latency of the wireless communication established between the robotic surgical system and the consultant device 401 to manage network flow. A measured/determined latency of a wireless network may be the same as a latency of a network that includes the wireless network, where the network may include a starting point/node for data to be transmitted to an ending point/node, and where the data is communicated by one computer/device associated with a surgical site to another computer/device associated with a location of the remote physician/surgeon. Scheduling of consultants can be based, at least in part, on expected latency (e.g., latency within the network 404 or other network) required to perform the telesurgery based on the received one or more surgery data. For example, a scheduling module may be configured to determine the requirement of the bandwidth (e.g., 10 MHz, 20 MHz, 30 MHz, etc.) needed and/or expected latency (e.g., ±50 milliseconds, ±70 milliseconds, ±100 milliseconds, etc.). The parameters for scheduling participation of the consultant device 401 can be selected by a surgical team, healthcare provider, or the like.

The user 421 can use the console 420 to view and control the surgical robot 440. The console 420 can be communicatively coupled to one or more components disclosed herein and can include input devices operated by one, two, or more users. The input devices can be hand-operated controls, but can alternatively, or in addition, include controls that can be operated by other parts of the user's body, such as, but not limited to, foot pedals. The console 420 can include a clutch pedal to allow the user 421 to disengage one or more sensor-actuator components from control by the surgical robot 440. The console 420 can also include display or output so that the one of more users can observe the patient being operated on, or the product being assembled, for example. In some embodiments, the display can show images, such as, but not limited to, medical images, video, etc. For surgical applications, the images could include, but are not limited to, real-time optical images, real-time ultrasound, real-time OCT images and/or other modalities, or could include pre-operative images, such as MRI, CT, PET, etc. The various imaging modalities can be selectable, programmed, superimposed, and/or can include other information superimposed in graphical and/or numerical or symbolic form.

The robotic surgical system 400 can include multiple consoles 420 to allow multiple users to simultaneously or sequentially perform portions of a surgical procedure. The term "simultaneous" herein refers to actions performed at the same time or in the same surgical step. The number and configuration of consoles 420 can be selected based on the surgical procedure to be performed, number and configurations of surgical robots, surgical team capabilities, or the like.

In embodiments, the robotic surgical system 400 performs robotic joint arthroscopic procedures based on patient data to improve outcomes. For example, the robotic surgical system 400 analyzes patient joint data to identify and evaluate anatomical structures, tissue (e.g., bone, soft tissue, etc.), biomechanics, and other features of the joints. The robotic surgical system 400 can perform one or more simulations to develop a robotic-enabled surgical plan that achieves one or more targeted outcomes. Image processing can be applied to patient images (e.g., scans, video, or the like) to determine elasticity, strength, and other properties of soft tissue, such as cartilage, tendons, synovial fluid, or the like.

The robotic surgical system 400 can assign properties to structures of the joint to accurately represent the functionality of the joint. This allows simulations to accurately represent complex anatomical structures. Advantageously, the robotic-enabled surgical plan can include surgical steps that can be performed with a higher degree of accuracy than manually performed steps. Additionally, the robotic surgical system 400 can dynamically modify surgical steps based on real-time analysis of the surgical site using ML algorithms to improve performance. In some embodiments, the robotic-enabled surgical plan can include both autonomously performed robotic surgical steps and manual surgical steps. This allows a surgical team to participate interactively with the robotic surgical system 400.

Pre-operative simulations can use a virtual patient-specific model that matches the pre-operative anatomy to generate pre-operative surgical plans. Intraoperative data can be used to generate intraoperative virtual models for intraoperative simulations performed to modify pre-operative surgical plans. For example, continuous or periodic intraoperative imaging of a surgical site can be performed to update the virtual model. If a tissue structure is modified (e.g., cut, removed, etc.), the virtual model can be updated accordingly. One or more simulations can then be performed using the modified virtual model to assess predicted outcomes based on the current state of the surgical site. Additionally, the system 900 can determine additional imaging that may be available. For example, when internal tissues are exposed via incisions or ports, the robotic surgical system 400 can automatically image the exposed internal tissue. This allows tissue analyses to be performed using near real-time or real-time acquired data.

The robotic surgical system 400 can be incorporated into or used with technology discussed in connection with FIGS. 1-18B. For example, one or more components of the robotic surgical system 400 can be incorporated into the operating room 102 discussed in connection with FIG. 1. By way of another example, a user interface and/or imaging device of the robotic surgical system 400 can be part of interface 420 discussed in connection with FIG. 4B. Output from the robotic surgical system 400 can be transmitted to controller 450 in FIG. 5 and/or various other components disclosed herein. Accordingly, the robotic surgical system 400 can be incorporated into robotic surgery systems, or utilized to perform manual surgical procedures or to perform other procedures disclosed herein.

With continued reference to FIG. 4A, the robotic surgical system 400 can include a surgical robot 440 configured to perform robotic joint arthroscopic surgery involving the extensor retinaculum. The surgical robot 440 can include the features and components discussed in connection with FIGS. 1-18B. The surgical robot 440 can receive one or more user inputs, workflow objects, and/or data files containing surgical actions for robotic movements. The user inputs can include, without limitation, type of procedure, targeted outcome, physician notes, or other user inputs disclosed herein. The workflow objects can include surgical techniques, surgical steps, surgical processes, etc. The data files can include executable instructions for performing the techniques/processes for specific surgical tools 154. The surgical robot 440 can determine one or more end effectors and/or surgical tools for performing robotic arthroscopic surgery. The end effectors and/or surgical tools can be displayed by a user interface for selective enabling and/or disabling by the user. The data files can be generated using ML algorithms and/or other techniques disclosed herein. In some embodiments, the surgical robot 440 can be designed to assist a surgeon in performing a surgical operation on a patient. The surgical robot 440 can include a controller, memory, and at least one robotic arm with an end effector. Likewise, embodiments of the system of FIG. 4A can include different and/or additional components disclosed herein or can be connected in different ways.

Robotic arthroscopic surgical steps can be displayed on the user interface (e.g., interfaces of displays 401/422, interface or GUI 461) in a sequence to enable execution of the data files containing the robotic movements. The arthroscopic surgical plan can be displayed for pre-operative viewing for surgical planning and/or intraoperative viewing (i.e., while the robotic surgical system robotically operates on the patient) for monitoring the procedure. For intraoperative viewing, the robotic surgical system 400 can determine information to be displayed based on received user input while controlling one or more of the tools operated by the robotic surgical system according to the user input. For example, predicted outcomes can be adjusted based on enabling and/or disabling of a surgical tool. The robotic surgical system 400 can select and display predicted outcomes and can also display surgical steps, surgical plans, patient databases (e.g., patient databases), joint data (e.g., joint data discussed in connection with FIGS. 15 and 17-18B), or other data. For example, a patient database and associated real-time generated predicted joint movement can be simultaneously displayed while the robotic surgical system 400 controls end effectors or surgical tools 154.

The robotic surgical system 400 automatically designs a surgical workflow for and performs robotic joint arthroscopic surgery. The system of FIG. 4A includes surgical robot 440, which is a robotic system designed to perform or assist a surgeon in performing a surgical operation on a patient. In embodiments, surgical robot 440 includes a controller, a memory, and at least one robotic arm having an end effector. Likewise, embodiments of the robotic surgical system 400 can include different and/or additional components or can be connected in different ways.

The robotic surgical system 400 can perform multi-modality imaging pre-operatively, intraoperatively, and/or post-operatively. Pre-operative images can be used to generate pre-operative plans. Intraoperative images can be used to modify surgical plans, update virtual models of surgical sites, provide monitoring of the surgical procedure to a surgical team, or combinations thereof. Post-operative multiple images can be generated to evaluate the predicted outcome of the procedure, success of the procedure, or the like. In some embodiments, tests are performed during one or more scans of the target region. In a single scan test, the robotic surgical system 400 can concurrently perform multiple tests while moving along the tissue sample. In multiple scan tests, the robotic surgical system 400 sequentially performs tests during corresponding scans and/or concurrently performs multiple tests during each scan. The tests can include, without limitation, mobility tests, range of motion tests, stability tests (e.g., lateral angle stability tests), and functional tests (e.g., foot lift tests, functional hop tests, Y-balance tests, etc.), and can be performed for one or more regions of interest. The robotic surgical system 400 can generate scanning/testing protocols for specific joints based on the patient's condition. The robotic surgical system 400 can perform different testing, imaging, and/or scanning protocols based on the analysis to be performed. The robotic surgical system 400 can compare pre-operative data and post-operative data to determine prediction accuracy scores for the surgical procedure, rehabilitation protocols, or the like. In response to prediction accuracy scores falling below a threshold score, the ML algorithm can be retrained to increase accuracy scores. The robotic surgical system 400 can generate patient-specific rehabilitation protocols based on the post-operative condition of the patient.

The robotic surgical system 400 can generate a virtual model based on captured images and can perform surgical simulations using the virtual model to predict at least one of joint functionality, stability of the joint, or the like. In embodiments, robotic surgical system 400 determines a next step of a surgical procedure to be performed by surgical robot 440 in accordance with a surgical plan. For example, an arthroscopic surgical plan can be modified based on the surgical simulations to achieve at least one of target post-operative functionality, stability of the joint, or other characteristics of the joints. Pre-operative images can be used to perform pre-operative surgical simulations to generate an initial surgical plan. Intraoperative images can be used to perform intraoperative simulations to allow for adjustments to the surgical plan based on newly captured image data. For example, if an unplanned alteration to tissue occurs, robotic surgical system 400 can identify the alteration and perform new simulations to determine how the alteration may affect the joint. The robotic surgical system 400 generates a modified surgical plan to achieve desired post-operative outcomes.

The robotic surgical system 400 can control imaging equipment to capture images of the altered tissue to generate an alternate or modified surgical plan. In the procedures discussed herein, the robotic surgical system 400 can acquire and analyze images to determine how to robotically apply one or more sutures to anchors. Post-operative simulations (e.g., functionality simulations, stability simulations, range of motion simulations) can use a real-time three-dimensionally generated virtual model. In some procedures, the robotic surgical system 400 can identify, using image processing techniques, one or more damaged tissue structures contributing to instability of a joint. The robotic surgical system 400 can then determine locations of anchoring and tethers for compensating for the one or more damaged tissue structures so as to, for example, increase stability of the joint while maintaining a predetermined threshold joint functionality value. The predetermined threshold joint functionality value for maintaining a minimum range of motion of the joint can be inputted by the user or determined by robotic surgical system 400. Example ranges of motion of joints are discussed in connection with FIGS. 7, 8A, and 8B.

In embodiments, tests are performed during one or more scans of the target region. In a single scan test, the robotic surgical system 400 can concurrently perform multiple tests while moving along the tissue sample. In multiple scan tests, system 600 sequentially performs tests during corresponding scans and/or concurrently performs multiple tests during each scan. The robotic surgical system 400 can perform different testing, imaging, and/or scanning protocols based on the analysis to be performed.

The robotic surgical system 400 can facilitate communication with another robotic surgical system, doctor, surgeon, or other medical professional by providing results (e.g., multi-modality data, raw data, visualizations of the data, and the like) from the test(s) in real-time. Further, the robotic surgical system 400 can combine the results from imaging device(s) to provide a diagnosis of a tissue sample, target region, surgical site, or combinations thereof. In surgical procedures, the results can be automatically transmitted to a surgical robot that analyzes the results to perform one or more surgical steps. Surgical robot 440 can request additional information from the robotic surgical system 400 to, for example, complete a surgical step, confirm completion of a surgical step, plan a surgical step, plan a series of surgical steps, or the like. For example, robotic surgical system 400 can receive multi-modality results from another system to perform a multi-modality-guided robotic surgical step. In embodiments, the results are displayed via display 422 for viewing by the surgical team, as shown in FIG. 4A. Additionally, or alternatively, the results can be viewable via console 420 by user 421 of FIG. 4A while, for example, monitoring or performing one or more surgical steps.

The robotic surgical system 400 includes the surgical robot 440 for performing robotic joint arthroscopic surgery for the lateral EDL tendon portion of the anatomy. The EDL is situated at the lateral part of the front of the leg. The EDL arises from the lateral condyle of the tibia, from the upper three-quarters of the anterior surface of the body of the fibula, from the upper part of the interosseous membrane, from the deep surface of the fascia, and from the intermuscular septa between the EDL and the tibialis anterior on the medial, and the peroneal muscles on the lateral side. Between the EDL and the tibialis anterior are the upper portions of the anterior tibial vessels and deep peroneal nerve. The EDL passes under the superior and inferior extensor retinaculum of the foot in company with the fibularis tertius, and divides into four slips, which run forward on the dorsum of the foot and are inserted into the second and third phalanges of the four lesser toes. The extensor retinaculum of the arm is located on the back of the forearm, just proximal to the hand. The extensor retinaculum is continuous with the palmar carpal ligament, which is located on the anterior side of the forearm. The superior extensor retinaculum of the leg is the upper part of the extensor retinaculum of the foot, which extends from the ankle to the heelbone.

The surgical robot 440 can request additional information from the robotic surgical system 400 to, for example, complete a surgical step, confirm completion of a surgical step, plan a surgical step, plan a series of surgical steps, or the like. For example, the robotic surgical system 400 can receive multi-modality results from another system to perform a multi-modality-guided robotic surgical step. In embodiments, the results are displayed via display 422 for viewing by the surgical team, as shown in FIG. 4A. Additionally, or alternatively, the results can be viewable via console 420 by a user 421 of FIG. 4A while, for example, monitoring or performing one or more surgical steps.

The robotic surgical system 400 comprises surgical robot 440, which is a robotic system designed to assist a surgeon in performing a surgical operation on a patient. Surgical robot 440 includes a controller, memory, and at least one robotic arm with an end effector. Surgical robot 440 may further include a user interface for accepting control inputs from a user, such as a surgeon or other medical professional and a communications interface for transmitting and receiving data to and from a cloud for the purpose of training an AI operating within the surgical robot or receiving remote commands from a remote user or an AI existing external to the surgical robot 440. The surgical robot 440 may additionally comprise a plurality of sensors for providing feedback to the user or an AI.

In embodiments, robotic surgical system 400 is used to simulate virtual models. Virtual models can be two-dimensional virtual models, three-dimensional models, and other models for representing anatomical features of the patient. The virtual models can have predefined kinematics, properties (e.g., tissue properties, cartilage properties, bone properties, implant properties, suture properties, anchor properties, etc.), dynamic characteristics, or the like. This allows virtual models to accurately represent pre-operative conditions of complex anatomical structures, such as joints, movement of surgical robots, operation of tools, etc. Pre-operative virtual models can represent predicted outcomes for joints, such as improved functionality, stability, or the like. The virtual models can be used to perform simulations to generate simulation data. In some embodiments, virtual models can incorporate or be based on 3D renderings of medical images.

Extended-reality surgical simulation environments can include virtual models that can be manipulated to simulate robotic steps performed by a surgical robot under control of the user, operating autonomously according to a surgical plan, etc. User input (e.g., user input via hand controls, a user interface, voice commands, etc.) can be used to control movements of virtual models of tools, end effectors, manipulators, multiple surgical robots, or the like. The surgical steps can be also be performed on virtual models representing anatomical structures. The system and/or user can analyze the simulated surgical steps to modify surgical plans, determine surgical steps, practice surgical steps, or the like. In some embodiments, the system can receive multiple models from databases, including manufacturer databases (e.g., manufactures of surgical equipment), hospital databases, etc. The models can be transformed into virtual models that can be imported into a single simulation environment. For example, the system can retrieve stored CAD models (e.g., IGES files, STEP files, universal CAD files) from manufactures of surgical instruments. The CAD models can be converted into virtual models that can be imported into the surgical simulation environment. This allows simulations to be performed for equipment from different manufactures. The robotic surgical system 400 can generate three-dimensional movements (e.g., anatomical movements, movements of the surgical tools, movements of the surgical robot, movements of implants, etc.) within the extended-reality (XR) surgical simulation environment to simulate surgical steps performed by the one or more surgical tools.

A 3D rendering is a mathematical representation of an object or surface as such object or surface would appear by width, breadth, and depth dimensions. The 3D rendering that is generated transforms the medical images into high-quality, detailed, and lifelike images. The 3D rendering can be generated by robotic surgical system 400. For example, robotic surgical system 400 uses computer graphics processing to generate 3D data and models. The robotic surgical system 400 creates a lifelike or non-photorealistic image. The 3D rendering output is a digital file of an object created using software or through 3D scanning.

In embodiments, robotic surgical system 400 includes a CAD GUI. The CAD GUI is a user interface for a computer software system to design surgical processes for patients. CAD refers to the use of computers to aid in the creation, modification, analysis, or optimization of a design, such as a surgical procedure. CAD software is used to increase the productivity of the designer or user, such as a doctor or medical professional, to improve the quality of design, to improve communications through documentation, and to create a database for the procedure. CAD output is often in the form of electronic files for print, machining, or other manufacturing operations.

The GUI is an interface(s) that may either accept inputs from users, provide outputs to users, or perform both actions. In one case, a user can interact with the interface(s) using one or more user-interactive objects and devices. The user-interactive objects and devices may include user input buttons, switches, knobs, levers, keys, trackballs, touchpads, cameras, microphones, motion sensors, heat sensors, inertial sensors, touch sensors, or a combination of the above. Further, the interface(s) may be implemented as a command line interface (CLI), a GUI, a voice interface, or a web-based user interface.

The CAD GUI enables a user, such as a surgeon, doctor, medical professional, etc., to view an area of a patient's body that requires surgery in a 3D space. The CAD GUI also allows the user to select various surgical tools 154, materials, and techniques required for the surgery and allows the user to manipulate the surgical tools 154, materials, and techniques, as rendered over the patient's 3D image to perform the processes and steps needed for the surgery in a virtual space. The user's movements and actions may be saved and stored in an operation database to assist the surgeon in performing the surgery or to provide the surgical robot 440 with the approximate (x, y, z) coordinates to perform the surgery.

The CAD GUI allows other users to view or replay the surgery in the 3D space to alter or adjust movements or actions to perform the surgery. In some embodiments, the CAD GUI may provide the user or surgical robot 440 with a list of materials needed, a list of surgical tools 154 required, a workflow process of the surgical procedure, a 3D visual replay of the surgical procedure, etc. A hospital network provides medical information of a patient to the surgical robot network, such as electronic health records, medical images (MRIs, X-rays, etc.), a list of the patient's doctors and health care professionals, the patient's current medications and prescriptions, the patient's medical history, the names of the patient's specialists, etc.

A GUI or guided user interface may be an interface(s) may either accept inputs from users or provide outputs to the users or may perform both the actions. In one case, a user can interact with the interface(s) using one or more user-interactive objects and devices. The user-interactive objects and devices may comprise user input buttons, switches, knobs, levers, keys, trackballs, touchpads, cameras, microphones, motion sensors, heat sensors, inertial sensors, touch sensors, or a combination of the above. Further, the interface(s) may either be implemented as a CLI, a GUI, a voice interface, or a web-based user interface. The CAD GUI 946 allows a user, such as a surgeon, doctor, medical professional, etc., to view an area of a patient's body that requires surgery in a 3D space. In embodiments, at least one surgical step described by a surgical workflow is indicated by a user using CAD GUI 946. For example, CAD GUI 946 enables a user to select various surgical tools 154, materials, and techniques required for the surgery and allows the user to manipulate the surgical tools 154, materials, and techniques, rendered over a patient's 3D image to perform the processes and steps needed for the surgery in a virtual space.

In embodiments, one or more ML systems trained to correlate feature vectors to prior patient data having favorable outcomes are executed. For example, surgical robot 440 includes one or more ML systems trained to correlate feature vectors to expected outputs in the training data. As part of the training of an ML model, the ML system can form a training set of favorable outcomes (e.g., prior patient data with favorable outcomes) and training labels by identifying a positive training set of features that have been determined to have a desired property in question, and, in some embodiments, forms a negative training set of features that lack the property in question. The property in question can include, without limitation, one or more threshold outcomes/scores, therapeutic effect(s), or other criteria selected by, for example, a user or surgical team.

The surgical robot 440 can include a correlation module configured to retrieve data from a surgery database based on the surgery type. The correlation module performs correlations on selected parameter(s) to determine if parameters are highly correlated. The correlation module determines if the correlation coefficient is over the predetermined threshold, for example, over a correlation coefficient (e.g., a predetermined correlation coefficient). If it is determined that the correlation coefficient is over the predetermined threshold, then the correlation module extracts the best match data point from the data set. The correlation module then stores the data entry for the best match data point in a recommendation database. If it is determined that the correlation coefficient is not over the predetermined threshold, or after the data entry for the best match data point is stored in the recommendation database, the correlation module determines if there are more parameters remaining in the surgery database. If it is determined that there are more parameters remaining in the surgery database, the correlation module selects the next parameter in the surgery database and the process returns to performing correlations on the parameters. If it is determined that there are no more parameters remaining in the surgery database, the correlation module returns to the base module.

The recommendation module can begin by being initiated by the base module. The recommendation module filters the recommendation database based on the correlation coefficient (e.g., the highest correlation coefficient). The recommendation module selects the highest correlated data entry in the recommendation database. Other techniques can be used.

For arthroscopic procedures, the training data can include, without limitation, pre-operative data, post-operative data, outcomes (e.g., short-term outcomes, long-term outcomes, etc.), and surgical data (e.g., adverse events, physician input, etc.). For leg-related procedures, the training data can include threshold criteria (e.g., threshold values, threshold scores, etc.), scores (e.g., American Orthopedic Foot and Ankle Society (AOFAS) score, Visual Analogue Scale (VAS) score, Cumberland Ankle Instability Tool (CAIT) scores, quality of life scores, pain scores, etc.), stress radiographs to measure tilt test (e.g., talar tilt test) and anterior drawer tests, or the like. The threshold criteria can be selected as a favorable outcome. The values/scores can be selected as threshold outcomes or therapeutic effect(s) for approving surgical plans, simulations, etc. For arm-related procedures, the training data can include, without limitation, thresholding values/scores, Disabilities of the Arm, Shoulder, and Hand (DASH) questionnaire scores, etc. The surgical robot 440 can set up and train the ML model as discussed in connection with FIG. 2 and can include one or more ML systems (e.g., ML system 200 of FIG. 2).

The surgical robot 440 can also generate surgical procedures or plans with joint stabilization predictions (e.g., post-operative stability scores of joints, long-term stability scores of joints, etc.), joint mechanics predictions (e.g., one or more target characteristics of joint mechanics), predicted restored function of the joint, combinations thereof, or the like. The surgical robot 440 can manage pain by, for example, determining ligament-attachment joint stabilization steps for utilizing connectors to adjust movement of the joint. For example, robotic surgical system 400 can identify attachment sites to be physically connected to other structures (e.g., ligaments, bones, muscle, etc.) of the joints.

In some implementations, robotic surgical system 400 can identify one or more attachment points along an anatomical structure (e.g., extensor retinaculum, dorsal carpal ligament, posterior annular ligament, antebrachial fascia, etc.) that are capable of serving as attachment points for limiting motion of the joint, reinforcing the joint, limiting range of motion of the joint, combinations thereof, or the like. Images of the anatomical structure can be analyzed to determine the contribution of the anatomical structure to properties of the joint. The robotic surgical system 400 can then identify the number and position of attachment points based on the desired forces to be applied to the anatomical structures. The properties of implantable connectors can be selected based on target outcomes. For example, unextendible, flexible sutures can connect a ligament to a bone on the opposite side of a joint to limit or fix a range of motion of a joint. This can allow the joint to have normal range of motion in one direction while limiting the range of motion in an opposite direction.

The surgical robot 440 can use one or more ML systems to analyze real-time data (e.g., video, images, etc.) of a surgery site to determine one or more candidate surgical steps, generate predicted outcomes for candidate surgical steps, and/or generate simulations for physician review. As shown in FIG. 4C, a physician can view a surgical site 465 annotated with, for example, labeled structures of a joint, joint mechanics information, plan surgical steps, surgical tools, or the like.

In embodiments, robotic surgical system 400 analyzes patient joint data to evaluate at least one of anatomical structures, tissue, or biomechanics of joints of the patient. A simulation is performed to generate a surgical plan, wherein the surgical plan is intended to achieve a targeted outcome for the surgical procedure. For example, patient data 472 includes, without limitation, target sites (e.g., attachment sites, anchor sites), joint data, mobility data, and other patient data related to the surgical procedure. Example information for display is discussed in connection with FIGS. 6A, 6B, 7, 8A, and 8B. The robotic surgical system 400 can predict post-operative outcomes based on, for example, properties of ligaments, properties of implantable connectors, etc. to improve joint stabilization, limit disease progression, and/or improve patient biomechanics. The predicted post-operative outcomes can be for a selected time or period of time. For example, robotic surgical system 400 can predict post-operative outcomes one month after surgery, six months after surgery, one year after surgery, two years after surgery, or the like. Age-related changes to anatomical structures, tissue, and other anatomical elements can be used to generate the predicted time-varying post-operative outcomes. By way of example, soft tissue, such as ligaments, may become hardened or lose elasticity over a period of time. The robotic surgical system 400 can predict biomechanics at joints based on such tissue changes. This allows a user to evaluate long-term outcomes of surgical procedures based on typical age-related effects.

In embodiments, patient joint data comprises patient images. Analyzing the patient joint data comprises applying image processing to the patient images to determine elasticity or strength of at least one of cartilage, tendons, or synovial fluid of the patient. For example, robotic surgical system 400 generates post-operative outcomes based on different types of simulations. The simulations can include nonlinear characteristics (e.g., micromechanics, mechanical behavior, etc.) of soft tissue. Linear, nonlinear, and other mechanical properties can be applied to tissue to generate linear finite element models, nonlinear finite element models, joint modeling (e.g., linear joint modeling, nonlinear joint modeling, dynamic joint modeling, etc.), or the like. For example, the robotic surgical system 400 can model and simulate the dynamic behavior of nonlinear anatomical structures of a joint. The dominant characteristics of the joints can be identified and used to determine anatomical features to be modified.

In embodiments, robotic surgical system 400 includes an imaging device, which is any device capable of collecting data which can be used to create an image, or a representation of a physical structure or phenomena. In embodiments, a plurality of surgical tools comprise an imaging sensor. The terms imaging device and imaging sensor are used interchangeably herein. The imaging device can include any device capable of detecting sound or electromagnetic waves and assembling a visual representation of the detected waves. Imaging devices can collect waves from any part of the electromagnetic spectrum or sounds at any range of frequencies, often as a matrix of independently acquired measurements that each represent a pixel of a 2D or 3D image. These measurements may be taken simultaneously or in series via a scanning process or a combination of methods. Some pixels of an image produced by an imaging device may be interpolated from direct measurements representing adjacent pixels in order to increase the resolution of a generated image.

The imaging device can include an algorithm or software module capable of determining qualitative or quantitative data from medical images. The algorithm can be a deep learning algorithm trained on a data set of medical images.

The imaging device may further refer to a device used to acquire medical imagery by any means including MRI, CT, or X-ray. The imaging device may further refer to a device used to acquire medical imagery by PET, ultrasound, or arthrography. The imaging device may further refer to a device used to acquire medical imagery by angiography, fluoroscopy, or myelography.

The imaging device can be controlled to acquire images that can be annotated with, for example, patient information, procedure information, or the like. The patient information can include, without limitation, damaged structures of the joint, joint mechanics information (e.g., a range of motion, degrees of freedom, areas contributing to joint instability, motion of FIGS. 7-8B, etc.), ligaments, bone, soft tissue, muscle, synovial sacs, or the like. The procedure information can include, for example, completed surgical steps, planned future surgical steps, information (e.g., calculations, technique information, etc.), attachment sites (e.g., anchor sites, suture sites, etc.), connector information (e.g., number of connectors, dimensions of connectors, properties of connectors, orientation of connectors, routing of connectors, etc.), and other information discussed in connection with FIGS. 1-8B, and other information disclosed herein.

The imaging device refers to any device capable of collecting data which can be used to create an image, or a representation of a physical structure or phenomena. An imaging device may include any device capable of detecting sound or electromagnetic waves and assembling a visual representation of the detected waves. The imaging device may collect waves from any part of the electromagnetic spectrum or sounds at any range of frequencies, often as a matrix of independently acquired measurements which each representing a pixel of a two or three-dimensional image. These measurements may be taken simultaneously or in series via a scanning process or a combination of methods. Some pixels of an image produced by an imaging device can be interpolated from direct measurements representing adjacent pixels in order to increase the resolution of a generated image.

In embodiments, a surgery is designed to address ankle instability to, for example, improve an outcome score, such as the AOFAS score, VAS score, overall joint score, composite joint score (e.g., composite score based on weighted AOFAS and VAS scores), etc. For example, the ankle can be pre-operatively and/or post-operatively evaluated to generate both pre-operative scores (e.g., AOFAS scores, VAS scores, etc.), and/or post-operative scores. Scores can be used to evaluate the ankles, subtalar, talonavicular, and calcaneocuboid joints, as well as arthrodesis, fractures, arthroplasty, and instabilities. The wrists, hands, shoulders, knee, and other anatomical structures can be scored using different scoring protocols.

In embodiments, robotic surgical system 400 determines that a surgical step is complete based on a surgical plan. For example, the surgical plan is generated to achieve a threshold score, increase/decrease a pre-operative score(s) (e.g., threshold increase/decrease of AOFAS score, VAS score, respectively), etc. The Brostrom-Gould repair surgery is primarily used to repair the anterior talofibular ligament (ATFL) in the ankle. The recovery time for the procedure varies according to the patient but usually takes a minimum of 3-6 months. The surgery stabilizes the ankle, improves the ankle's mechanics, and restores function. The surgery helps a patient to experience less pain related to his or her injury and ankle sprains, as well as to avoid early arthrosis.

Figure 4B:
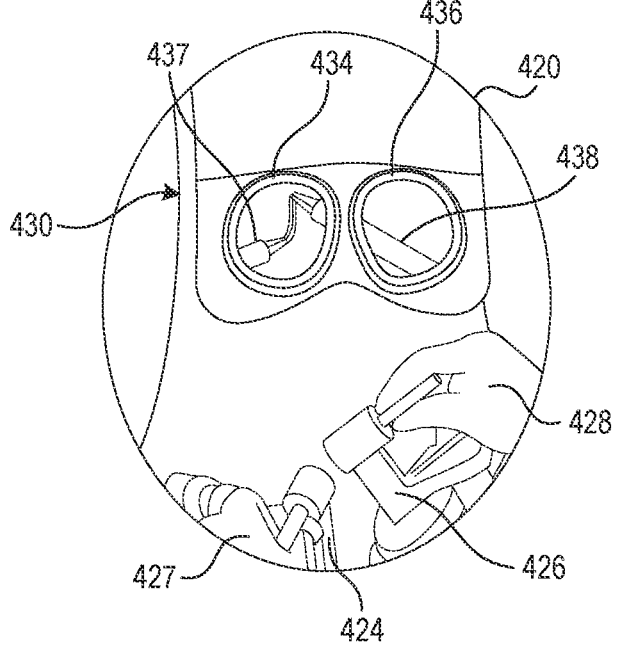
FIG. 4B illustrates an example console of the robotic surgical system of FIG. 4A, in accordance with one or more embodiments.
Figure 4C:
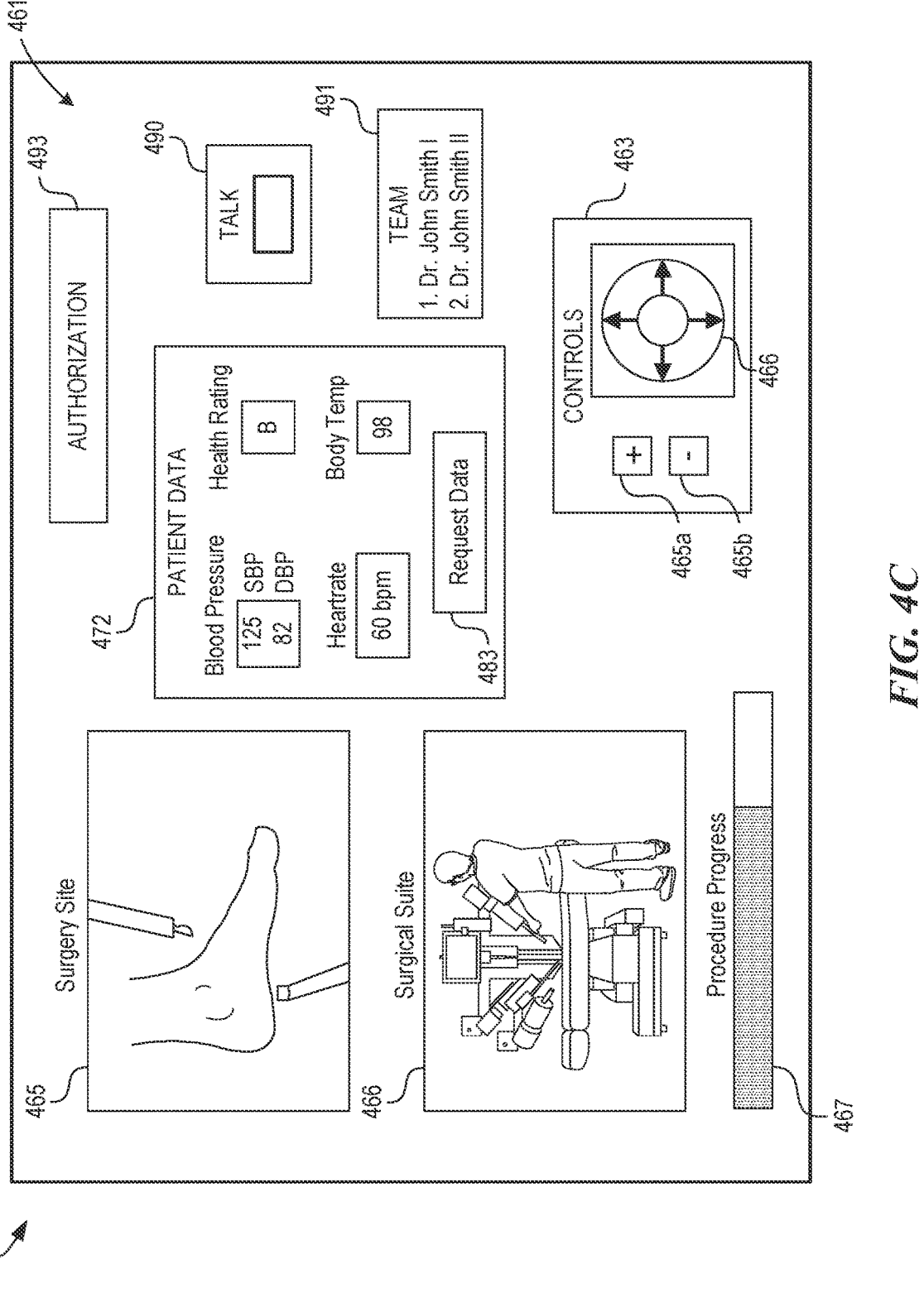
FIG. 4C illustrates an example display of a user device, in accordance with one or more embodiments.

FIG. 4B illustrates an example console 420 of the robotic surgical system 400 of FIG. 4A, in accordance with one or more embodiments. The console 420 includes hand-operated input devices 424, 426, illustrated held by the user's left and right hands 427, 428, respectively. A viewer 430 includes left and right eye displays 434, 436. The user can view, for example, the surgical site, instruments 437, 438, or the like. The user's movements of the input devices 424, 426 can be translated in real-time to, for example, mimic the movement of the user on the viewer 430 and display (e.g., display 124 of FIG. 1) and within the patient's body while the user can be provided with output, such as alerts, notifications, and information. The information can include, without limitation, surgical or implantation plans, patient vitals, modification to surgical plans, values, scores, predictions, simulations, and other output, data, and information disclosed herein. The console 420 can be located at the surgical room or at a remote location.

The viewer 430 can display at least a portion of a surgical plan, including multiwavelength images, imaging modality information, fused data sets, tissue types, mapped images (e.g., tissue types maps, bone tissue maps, tissue density maps, diseased tissue maps, tissue condition maps, etc.), past and future surgical steps, patient monitor readings (e.g., vitals), surgical room information (e.g., available team members, available surgical equipment, surgical robot status, or the like), images (e.g., pre-operative images, images from simulations, real-time images, instructional images, etc.), and other surgical assist information. In some embodiments, the viewer 430 can be a VR/AR headset, display, or the like. The robotic surgical system 400, illustrated and described in more detail with reference to FIG. 4A, can further include multiple viewers 430 so that multiple members of a surgical team can view the surgical procedure. The number and configuration of the viewers 430 can be selected based on the configuration and number of surgical robots.

In some embodiments, user 462 uses a visualization device 464 to monitor a surgical procedure. The visualization device 464 is a wearable artificial reality or extended reality (XR) device. The visualization device 464 can communicate, via the network 404, with components of the operating room 402 and can be a wearable augmented-reality (AR) device that provides virtually reality simulations for assisting with surgical procedures by, for example, displaying information (e.g., surgical plan information, identifying anatomical features (e.g., tissue, organs, abnormal features, normal features, or non-targeted tissue), or other information. The system 400 can coordinate or synchronize activities of the user. Example visualization devices are discussed in connection with FIGS. 19-22.

Referring again to FIG. 4A, the surgical robot 440 can include one or more controllers, computers, sensors, arms, articulators, joints, links, grippers, motors, actuators, imaging systems, effector interfaces, end effectors, or the like. For example, a surgical robot with a high number of degrees of freedom can be used to perform complicated procedures whereas a surgical robot with a low number of degrees of freedom can be used to perform simple procedures. The configuration (e.g., number of arms, articulators, degrees of freedom, etc.) and functionality of the surgical robot 440 can be selected based on the procedures to be performed.

The surgical robot 440 can operate in different modes selected by a user, set by the surgical plan, and/or selected by the robotic surgical system 400. In some procedures, the surgical robot 440 can remain in the same mode throughout a surgical procedure. In other procedures, the surgical robot 440 can be switched between modes any number of times. The configuration, functionality, number of modes, and type of modes can be selected based on the desired functionality and user control of the robotic surgical system 400. The robotic surgical system 400 can switch between modes based on one or more features, such as triggers, notifications, warnings, events, etc. Different example modes are discussed below. A trigger can be implemented in software to execute a jump to a particular instruction or step of a program. A trigger can be implemented in hardware, e.g., by applying a pulse to a trigger circuit.

In a user control mode, a user 421 controls, via the console 420, movement of the surgical robot 440. The user's movements of the input devices can be translated in real-time into movement of end effectors 452 (one identified).

In a semi-autonomous mode, the user 421 controls selected steps and the surgical robot 440 autonomously performs other steps. For example, the user 421 can control one robotic arm to perform one surgical step while the surgical robot 440 autonomously controls one or more of the other arms to concurrently perform another surgical step. In another example, the user 421 can perform steps suitable for physician control. After completion, the surgical robot 440 can perform steps involving coordination between three or more robotic arms, thereby enabling complicated procedures. For example, the surgical robot 440 can perform steps involving four or five surgical arms, each with one or more end effectors 452. The surgical robot 440 can include a multi-modality imager 453 having imaging devices 454a, 454b (collectively "imaging devices 454"). The imaging devices 454 can be, for example, PET scanners, ultrasound imagers, MRI imagers, CT scanners, cameras (e.g., camera imager hardware, digital cameras, etc.), infrared imagers, etc. In embodiments, the surgical robot 440 retrieves/receives images from standalone X-ray machines, MRI machines, CT scanners, etc. Example imaging devices are discussed in connection with FIGS. 1 and 6. The number, imaging capabilities, and configurations of the imaging devices 454 can be selected based on the imaging to be performed.

The robotic surgical system 400 can automatically generate multi-modality images based on surgical plans and then perform one or more surgical steps of a planned surgical procedure. In embodiments, the robotic surgical system 400 analyzes a surgical plan for a patient to generate an imaging plan for obtaining patient information for diagnostic purposes, modifying the surgical plan, performing surgical steps (e.g., one surgical step, multiple surgical steps, all surgical steps), etc. The imaging plan can include, without limitation, one or more regions of interest, targeted information, predicted features of interest, information for diagnostic purposes, or the like. The robotic surgical system 400 can generate the imaging plan based on imaging capabilities of the multi-modality imager 453. The robotic surgical system 400 can notify the surgical team to add or replace imaging devices 454 to achieve the desired imaging capability.

The robotic surgical system 400 can retrieve available images of a patient from, for example, electronic medical records, image databases, and/or other imaging sources. The robotic surgical system 400 can identify and retrieve images that can be processed for producing one or more multi-modality images. The robotic surgical system 400 can determine whether additional unavailable images could be useful for generating multi-modality images that (1) meet at least one threshold criteria (e.g., a confidence score), (2) identify features of interest, (3) have diagnostic capability criteria, etc. In some procedures, the robotic surgical system 400 retrieves available images and determines imaging programs or parameters (e.g., positions, imaging settings, etc.) of one or more of the imaging devices 454 corresponding to the available images. In embodiments, a machine learning system (see FIG. 2) can be used to generate imaging plans based on training sets. The training sets can include, for example, single modality training sets, composite multi-modality training sets, confirmed diagnostic training sets, and other training sets. This allows the robotic surgical system 400 to perform re-training procedures for continuously or periodically training the machine learning system. Newly-captured images can be keyed to or matched with the retrieved images, thereby increasing accuracy of the multi-modality images. During intro-operative imaging, the images can be analyzed in real-time to further control the robotic surgical system 400.

In an autonomous mode, the surgical robot 440 can autonomously perform steps under the control of the data system 450. The robotic surgical system 400 can be pre-programmed with instructions for performing the steps autonomously. For example, command instructions can be generated based on a surgical plan. The surgical robot 440 autonomously performs steps or the entire procedure. The user 421 and surgical team can observe the surgical procedure to modify or stop the procedure. Advantageously, complicated procedures can be autonomously performed without user intervention to enable the surgical team to focus and attend to other tasks. Although the robotic surgical system 400 can autonomously perform steps, the surgical team can provide information in real-time that is used to continue the surgical procedure. The information can include surgical robot input, surgical team observations, and other data input.

The robotic surgical system 400 can also adapt to the user control to facilitate completion of the surgical procedure. In some embodiments, the robotic surgical system 400 can monitor, via one or more sensors, at least a portion of the surgical procedure performed by the surgical robot 440. The robotic surgical system 400 can identify an event, such as a potential adverse surgical event, associated with a robotically performed surgical task. For example, a potential adverse surgical event can be determined based on acquired monitoring data and information for the end effector, such as surgical tool data from a medical device report, database, manufacturer, etc. The robotic surgical system 400 can perform one or more actions based on the identified event. The actions can include, without limitation, modification of the surgical plan to address the potential adverse surgical event, thereby reducing the risk of the event occurring. The adverse surgical event can include one or more operating parameters approaching respective critical thresholds, as discussed in connection with FIG. 12. The adverse surgical events can be identified using a machine learning model trained using, for example, prior patient data, training sets (e.g., tool data), etc.

In some embodiments, the robotic surgical system 400 determines whether a detected event (e.g., operational parameters outside a target range or exceeding a threshold, etc.) is potentially an adverse surgical event based on one or more criteria set by the robotic surgical system 400, user, or both. The adverse surgical event can be an adverse physiological event of the patient, surgical robotic malfunction, surgical errors, or other event that can adversely affect the patient or the outcome of the surgery. Surgical events can be defined and inputted by the user, surgical team, healthcare provider, manufacturer of the robotic surgery system, or the like.

The robotic surgical system 400 can take other actions in response to identification of an event. If the robotic surgical system 400 identifies an end effector malfunction or error, the robotic surgical system 400 can stop usage of the end effector and replace the malfunctioning component (e.g., surgical tool or equipment) to complete the procedure. The robotic surgical system 400 can monitor hospital inventory, available resources in the surgical room 402, time to acquire equipment (e.g., time to acquire replacement end effectors, surgical tools, or other equipment), and other information to determine how to proceed with surgery. The robotic surgical system 400 can generate multiple proposed surgical plans for continuing with the surgical procedure. The user and surgical team can review the proposed surgical plans to select an appropriate surgical plan. The robotic surgical system 400 can modify a surgical plan with one or more corrective surgical steps based on identified surgical complications, sensor readings, or the like. The surgical steps include, without limitation, cauterizing, cutting tissue, clamping tissue, stapling tissue, excising tissue, implanting items, alternative steps to replace planned surgical steps, manipulating tissue, or other steps disclosed herein. The surgical steps can be selected to keep the patient's vital(s) within a target range, for example, based on one or more surgical criteria (e.g., overall surgical time, length of surgical step, etc.).

The robotic surgical system 400 can retrieve surgical system information from a database to identify events. The database can describe, for example, maintenance of the robotic surgery system, specifications of the robotic surgery system, specifications of end effectors, surgical procedure information for surgical tools, consumable information associated with surgical tools, operational programs and parameters for surgical tools, monitoring protocols for surgical tools, or the like. The robotic surgical system 400 can use other information in databases disclosed herein to generate rules for triggering actions, identifying warnings, defining events, or the like. Databases can be updated with data (e.g., intraoperative data collected during the surgical procedure, simulation data, etc.) to intraoperatively adjust surgical plans, collect data for ML/AI training sets, or the like. Data from on-site and off-site simulations (e.g., pre-, or post-operative virtual simulations, simulations using models, etc.) can be generated and collected.

The surgical robot 440 can include robotic arms 451 (one identified) with robotic links, motors, and integrated or removable end effectors 452 (one identified). The end effectors 452 can include, without limitation, imagers (e.g., cameras, optical guides, etc.), robotic grippers, instrument holders, cutting instruments (e.g., cutters, scalpels, or the like), drills, cannulas, reamers, rongeurs, scissors, clamps, or other equipment or surgical tools disclosed herein. In some embodiments, the end effectors can be reusable or disposable surgical tools. The number and configuration of end effectors can be selected based on the configuration of the robotic system, procedure to be performed, surgical plan, etc. Imaging and viewing technologies can integrate with the surgical robot 440 to provide more intelligent and intuitive results.

The data system 450 can improve surgical planning, monitoring (e.g., via the display 422), data collection, surgical robotics/navigation systems, intelligence for selecting instruments, implants, etc. The data system 450 can execute, for example, surgical control instructions or programs for a guidance system (e.g., ML guidance system, AI guidance system, etc.), surgical planning programs, event detection programs, surgical tool programs, etc. For example, the data system 450 can increase procedure efficiency and reduce surgery duration by providing information insertion paths, surgical steps, or the like. The data system 450 can be incorporated into or include other components and systems disclosed herein. As shown by FIG. 4A, the display 422 can display, for example, a diagnosis of tissue, images, maps, surgical plans, etc. For example, the display 422 can display a diagnostic image or map showing, for example, a bone in image 423 (discussed in more detail below with reference to multi-modality imaging), regions of interest (e.g., zones of diseased tissue, regions of tissue with specific characteristic(s), margins, etc.), features of interest, anatomical elements (e.g., cartilage, soft tissue, etc.), or the like. An example image is discussed in connection with FIG. 15. In some embodiments, a diagnostic image can include tissue density, tissue state, identified disease tissue, or the like. The system 402 can use the displayed data to perform one or more surgical steps. A user can view the display 422 to confirm the position of the tissue during the procedure.

Referring to FIGS. 4A and 4C, the consultant device 401 can display procedure information from the surgery room, equipment controls, and other data disclosed herein. Referring now to FIG. 4C, the consultant device can display a GUI 461 for telepresence consulting. The GUI 461 includes an authorization input 493 for authorizing the consultant for participation in a surgical procedure and displays procedure and patient data 465, 466, 472, 491. Imaging equipment can automatically capture images for surgical side viewing via a display 465. The GUI 461 includes a procedure progress 467 that can be updated to show completed progress for the procedure, and controls 463 can be used to operate machines/applications. The user can customize the GUI 461 by rearranging the displayed items for convenience.

The consultant can use an authorization input 493 to, for example, input user authorization information (e.g., access codes, pins, etc.), employee credential information, surgical procedure information (e.g., serial number or code for the surgical procedure), or the like to access and operate equipment. If the consultant needs additional permission rights, the consultant can request the additional permission rights using the authorization input 493. For example, if an adverse event occurs during the procedure requiring the consultant to provide additional care, the consultant can request access to the additional equipment (e.g., robotic arms of surgical robot, breathing machine, heart rate monitor, etc.) via the authorization input 493. The surgical suite system can receive the requested authorization and perform an authorization protocol routine to determine whether the consultant should be granted permission rights to the additionally requested equipment. The surgical suite system can analyze the surgical plan, planned permission rights (e.g., plan of permission rights assigning permission rights to features or steps of the surgical plan), consultant credentials and/or expertise, and/or other information disclosed herein to determine whether to grant permissions. If requested permission rights are denied, the on-site medical team can be notified of the denied request and consultant input, recommendation, etc. If the request is granted, the system can automatically establish communication and control channels for displaying the additional information for the additional equipment via the consultant device 401. The procedure progress 467 can show completed progress for the modified procedure based on the additional equipment.

Dynamic updating of the equipment controls 463 on the consultant device 401 allows the user to acquire control of additional medical equipment in the same consulting session without disrupting communication channels. This reduces the risk of latency and/or network problems that could affect the medical procedure. The controls 463 can be configured to perform all or some of the controls as discussed in connection with FIG. 4B. For example, the controls 463 can include a touch input control module 466 with input features 465a, 465b that can be used to increase or decrease, respectively, settings of equipment. The touch input control module 466 can be used to control movement of, for example, robotic surgical arms, robotic manipulators, and effectors, or the like. For example, the touch input control module 466 can be configured to provide the same controllability as the hand-operated input devices 424, 426 of FIG. 4B. In some embodiments, the controls 463 of FIG. 4C can be modified to include controls for the additional equipment such that the consultant has access to controls for operating newly available equipment in real-time while continuing to view real-time patient data 472. Data collected by and/or associated with additional equipment can automatically be added to the patient data 472.

The consultant device 401 can include a procedure viewer 465, a surgical suite or room viewer 466, and/or other viewers or windows for providing viewing (e.g., real-time or near real-time viewing) of the surgical suite (e.g., viewing at operating rooms, recovery rooms, etc.), medical team, medical equipment, etc. The consultant device 401 can display patient data 472 that can include, for example, blood pressure, health rating, heart rate, body temperature, vitals, physician notes, and/or additional patient data useful to the consultant. To change or receive additional patient data, the consultant can use a request data button 483 to send a message or notification to the on-site surgical team to provide additional patient data. The consultant can use a talk feature 490 to verbally communicate with the surgical team. The consultant device 401 can also display the surgical team information 491. The surgical team information can list physicians, nurses, staff, consultants, and other staffing information.

The robotic surgical system 400, illustrated and described in more detail with reference to FIG. 4A, can further include multiple consultant devices 401 so that multiple members of a surgical team or consultants can view the surgical procedure. The number and configuration of the consultant devices 401 can be selected based on the configuration and number of surgical robots, monitoring equipment, etc. The consultant device 401 can also display procedure data, including a surgical plan (e.g., a surgical plan including completed and future planned surgical steps), patient monitor readings, surgical suite or room information (e.g., available team members, available surgical equipment, surgical robot status, or the like), images (e.g., pre-operative images, images from simulations, real-time images, instructional images, etc.), and other surgical assist information. In some embodiments, the consultant device 401 can be an AR/VR headset, display, or the like.

Referring to FIG. 4A, the robotic surgical system 400 can be used to perform open procedures, minimally invasive procedures, such as laparoscopic surgeries, non-robotic laparoscopic/abdominal surgery, retroperitoneoscopy, arthroscopy, pelviscopy, nephroscopy, cystoscopy, cisternoscopy, sinoscopy, hysteroscopy, urethroscopy, and the like. The methods, components, apparatuses, and systems can be used with many different systems for conducting robotic or MIS. One example of a surgical system and surgical robots which can incorporate methods and technology is the DAVINCI™ system available from Intuitive Surgical, Inc.™ of Mountain View, California. However, other surgical systems, robots, and apparatuses can be used.

The robotic surgical system 400 can perform one or more simulations using selected entry port placements and/or robot positions, to allow a surgeon or other user to practice procedures. The practice session can be used to generate, modify, or select a surgical plan. In some embodiments, the system can generate a set of surgical plans for physician consideration. The physician can perform practice sessions for each surgical plan to determine and select a surgical plan to be implemented. In some embodiments, the systems disclosed herein can perform virtual surgeries to recommend a surgical plan. The physician can review the virtual simulations to accept or reject the recommended surgical plan. The physician can modify surgical plans pre-operatively or intraoperatively.

Embodiments can provide a means for mapping the surgical path for neurosurgery procedures that minimize damage through AI mapping. The software for AI is trained to track the least destructive pathway. A surgical robot can make an initial incision based on a laser marking on the skin that illuminates the optimal site. Next, a robot can make a small hole and insert surgical equipment (e.g., guide wires, cannulas, etc.) that highlights the best pathway. This pathway minimizes the amount of tissue damage that occurs during surgery. Mapping can also be used to identify one or more insertion points associated with a surgical path. Mapping can be performed before treatment, during treatment, and/or after treatment. For example, pretreatment and post-treatment mapping can be compared by the surgeon and/or ML/AI system. The comparison can be used to determine next steps in a procedure and/or further train the ML/AI system. In some embodiments, the system determines the location, number, angle, and depth of arthroscopic ports (e.g., tubes, rods, etc.) to place in a patient. The system can select the location, number, angle, and depth of the arthroscopic ports based on the maneuverability of the surgical robot, maneuverability of the end effectors of the surgical robot and/or the availability of the surgical tool to place the arthroscopic ports in the patient.

Figure 5:
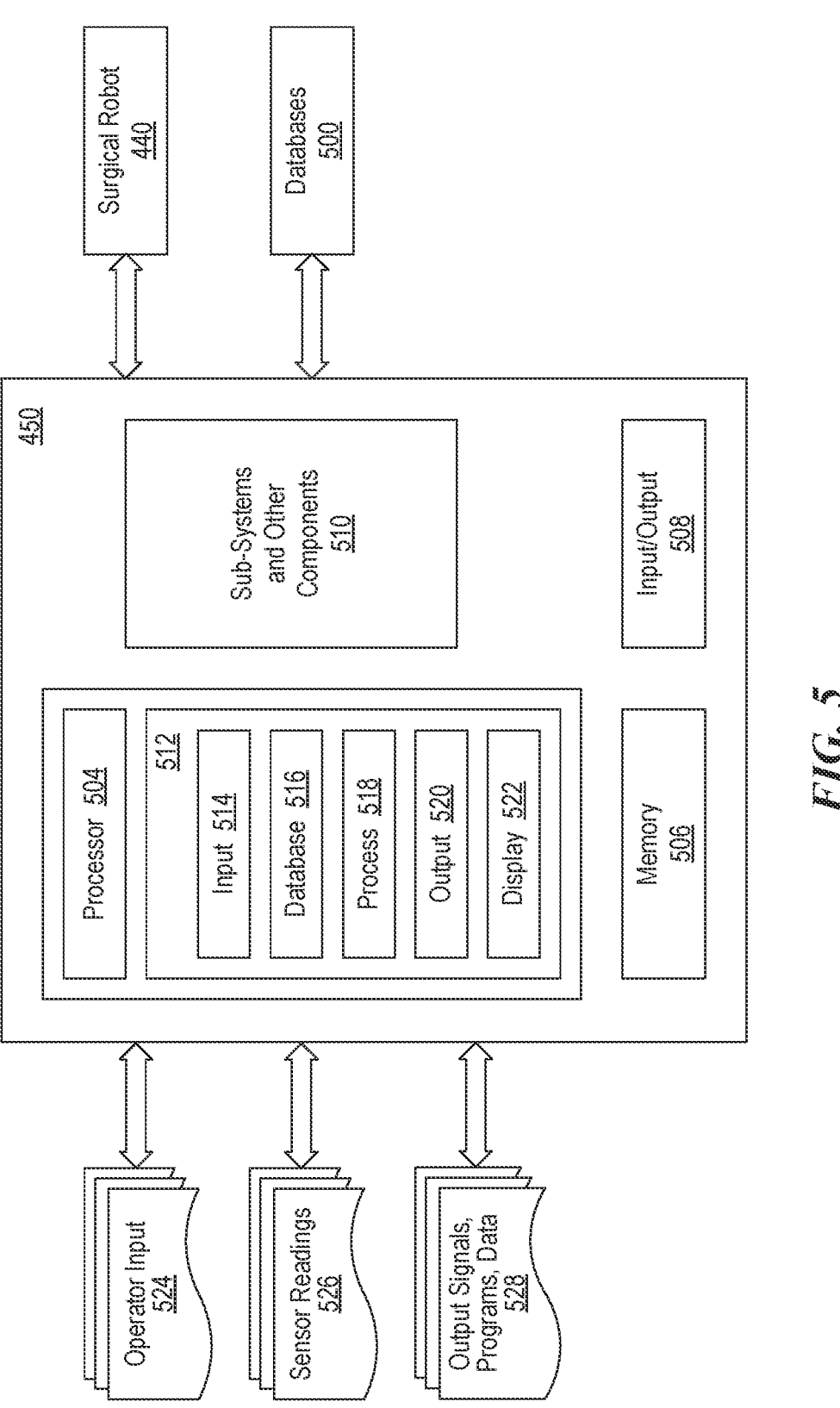
FIG. 5 is a schematic block diagram illustrating subcomponents of the robotic surgical system of FIG. 4A, in accordance with one or more embodiments.

FIG. 5 is a schematic block diagram illustrating subcomponents of the robotic surgical system 400 of FIG. 4A in accordance with embodiment of the present technology. The data system 450 has one or more processors 504, a memory 506, input/output devices 508, and/or subsystems and other components 510. The processor 504 can perform any of a wide variety of computing processing, image processing, robotic system control, plan generation or modification, and/or other functions. Components of the data system 450 can be housed in a single unit (e.g., within a hospital or surgical room) or distributed over multiple, interconnected units (e.g., though a communications network). The components of the data system 450 can accordingly include local and/or devices.

As illustrated in FIG. 5, the processor 504 can include a plurality of functional modules 512, such as software modules, for execution by the processor 504. The various implementations of source code (i.e., in a conventional programming language) can be stored on a computer-readable storage medium or can be embodied on a transmission medium in a carrier wave. The modules 512 of the processor 504 can include an input module 514, a database module 516, a process module 518, an output module 520, and, optionally, a display module 524 for controlling the display.

In operation, the input module 514 accepts an operator input 524 via the one or more input devices, and communicates the accepted information or selections to other components for further processing. The database module 516 organizes plans (e.g., robotic control plans, surgical plans, etc.), records (e.g., maintenance records, patient records, historical treatment data, etc.), surgical equipment data (e.g., instrument specifications), control programs, and operating records and other operator activities, and facilitates storing and retrieving of these records to and from a data storage device (e.g., internal memory 506, external databases, etc.). Any type of database organization can be utilized, including a flat file system, hierarchical database, relational database, distributed database, etc.

In the illustrated example, the process module 518 can generate control variables based on sensor readings 526 from sensors (e.g., end effector sensors of the surgical robot 440, patient monitoring equipment, etc.), operator input 524 (e.g., input from the surgeon console 420 and/or other data sources), and the output module 520 can communicate operator input to external computing devices and control variables to controllers. The display module 522 can be configured to convert and transmit processing parameters, sensor readings 526, output signals 528, input data, treatment profiles and prescribed operational parameters through one or more connected display devices, such as a display screen, touch screen, printer, speaker system, etc.

In various embodiments, the processor 504 can be a standard central processing unit or a secure processor. Secure processors can be special-purpose processors (e.g., reduced instruction set processor) that can withstand sophisticated attacks that attempt to extract data or programming logic. The secure processors cannot have debugging pins that enable an external debugger to monitor the secure processor's execution or registers. In other embodiments, the system can employ a secure field-programmable gate array, a smartcard, or other secure devices.

The memory 506 can be standard memory, secure memory, or a combination of both memory types. By employing a secure processor and/or secure memory, the system can ensure that data and instructions are both highly secure and sensitive operations such as decryption are shielded from observation. In various embodiments, the memory 506 can be flash memory, secure serial EEPROM, secure field-programmable gate array, or secure application-specific integrated circuit. The memory 506 can store instructions for causing the surgical robot 440 to perform acts disclosed herein.

The input/output device 508 can include, without limitation, a touch screen, a keyboard, a mouse, a stylus, a push button, a switch, a potentiometer, a scanner, an audio component such as a microphone, or any other device suitable for accepting user input and can also include one or more video monitors, a medium reader, an audio device such as a speaker, any combination thereof, and any other device or devices suitable for providing user feedback. For example, if an applicator moves an undesirable amount during a treatment session, the input/output device 508 can alert the subject and/or operator via an audible alarm. The input/output device 508 can be a touch screen that functions as both an input device and an output device.

The data system 450 can output instructions to command the surgical robot 440 and communicate with one or more databases 2600. The surgical robot 440 or other components disclosed herein can communicate to send collected data (e.g., sensor readings, instrument data, surgical robot data, etc.) to the database 500. This information can be used to, for example, create new training data sets, generate plans, perform future simulations, post-operatively analyze surgical procedures, or the like. The data system 450 can be incorporated, used with, or otherwise interact with other databases, systems, and components disclosed herein. In some embodiments, the data system 450 can be incorporated into the surgical robot 440 or other systems disclosed herein.

In some embodiments, the data system 450 can be located at a remote location and can communicate with a surgical robot via one or more networks. For example, the data system 450 can communicate with a hospital via a network, such as a wide area network, a cellular network, etc. One or more local networks at the hospital can establish communication channels between surgical equipment within the surgical room.

A surgical program or plan ("surgical plan") can include, without limitation, patient data (e.g., pre-operative images, medical history, physician notes, etc.), imaging programs, surgical steps, mode switching programs, criteria, goals, or the like. The imaging programs can include, without limitation, AR/VR programs, identification programs (e.g., fiducial identification programs, tissue identification programs, target tissue identification programs, etc.), image analysis programs, or the like. Surgical programs can define surgical procedures or a portion thereof. For example, surgical programs can include end effector information, positional information, surgical procedure protocols, safety settings, surgical robot information (e.g., specifications, usage history, maintenance records, performance ratings, etc.), order of surgical steps, acts for a surgical step, feedback (e.g., haptic feedback, audible feedback, etc.), or the like. The mode switching programs can be used to determine when to switch the mode of operation of the surgical robot 440. For example, mode switching programs can include threshold or configuration settings for determining when to switch the mode of operation of the surgical robot 440. Example criteria can include, without limitation, thresholds for identifying events, data for evaluating surgical steps, monitoring criteria, patient health criteria, physician preference, or the like. The goals can include intraoperative goals, post-operative goals (e.g., target outcomes, metrics, etc.), goal rankings, etc. Monitoring equipment or the surgical team can determine goal progress, whether a goal has been achieved, etc. If an intraoperative goal is not met, the surgical plan can be modified in real-time so that, for example, the post-operative goal is achieved. The post-operative goal can be redefined intraoperatively in response to events, such as surgical complications, unplanned changes to patient's vitals, etc.

The surgical plan can also include healthcare information, surgical team information, assignments for surgical team members, or the like. The healthcare information can include surgical room resources, hospital resources (e.g., blood banks, standby services, available specialists, etc.), local or remote consultant availability, insurance information, cost information (e.g., surgical room costs, surgical team costs, etc.).

The systems disclosed herein can generate pre-operative plans and simulation plans. Pre-operative plans can include scheduling of equipment, surgical room, staff, surgical teams, and resources for surgery. The systems can retrieve information from one or more databases to generate the pre-operative plan based on physician input, insurance information, regulatory information, reimbursements, patient medical history, patient data, or the like. Pre-operative plans can be used to generate surgical plans, cost estimates, scheduling of consultants and remote resources, or the like. For example, a surgical plan can be generated based on available resources scheduled by the pre-operative plans. If a resource becomes unavailable, the surgical plan can be adjusted for the change in resources. The healthcare provider can be alerted if additional resources are recommended. The systems disclosed herein can generate simulation plans for practicing surgical procedures. On approval, a surgeon can virtually simulate a procedure using a console or another simulation device. Plans (e.g., surgical plans, implantation plans, etc.) can be generated and modified based on the surgeon's performance and simulated outcome.

The systems disclosed herein can generate post-operative plans for evaluating surgical outcomes, developing physical therapy and/or rehab programs and plans, etc. The post-operative plans can be modified by the surgical team, primary care provider, and others based on the recovery of the patient. In some embodiments, systems generate pre-operative plans, surgical plans, and post-operative plans prior to beginning a surgical procedure. The system then modifies one or more or the plans as additional information is provided. For example, one or more steps of the methods discussed herein can generate data that is incorporated into the plan. ML data sets to be incorporated into the plan generate a wide range of variables to be considered when generating plans. Plans can be generated to optimize patient outcome, reduce or limit the risk of surgical complications, mitigate adverse events, manage costs for surgical procedures, reduce recovery time, or the like. The healthcare provider can modify how plans are generated over time to further optimize based on one or more criteria.

FIG. 6 is a block diagram illustrating an example robotic surgical system, in accordance with one or more embodiments. The system can be incorporated into or used with technology discussed in connection with FIGS. 1-5. For example, one or more components of the system 600 can be incorporated into the operating room 102 discussed in connection with FIG. 1. By way of another example, a user interface 610 and/or imaging device 618 of the system 600 can be part of the console 420 discussed in connection with FIG. 4B. Output from the system 600 can be transmitted to the controller 604 and/or various other components disclosed herein. Accordingly, the system can be incorporated into robotic surgery systems, or utilized to perform manual surgical procedures or to perform other procedures disclosed herein. Portions of the system 600 are implemented using the components of the example computer system 300 illustrated and described in more detail with reference to FIG. 3. Likewise, embodiments of the system 600 can include different and/or additional components or can be connected in different ways.

This system includes a surgical robot 602, which is a robotic system designed to perform a surgical operation or assist a surgeon in performing a surgical operation on a patient. The surgical robot can perform digital image analysis for robotic installation of surgical implants. An example surgical robot 440 is illustrated and described in more detail with reference to FIG. 4A. The surgical robot 602 can include a controller 604, a memory 606, and at least one robotic arm 612 having an end effector 614. The surgical robot 602 can further include a user interface 610 for accepting control inputs from a user, such as a surgeon or other medical professional. The surgical robot 602 can further include a communications interface 608 for transmitting and receiving data to and from a cloud 624 for the purpose of training an artificial intelligence (AI) implemented within the surgical robot 602, or receiving commands from a remote user or another AI implemented external to the surgical robot 602. An example AI (machine learning system 200) is illustrated and described in more detail with reference to FIG. 2. The surgical robot 602 can additionally include multiple sensors 616 for providing feedback to the user or an AI.

The controller 604 shown by FIG. 6 is a computing device including a computer processor for performing computations. The controller 604 communicates with a memory 606 for storing data. The controller 604 is in communication with a communications interface 608 and can further control the at least one robotic arm 612 and end effector 614 of the surgical robot 602. In embodiments, the controller is a commercially available central processing unit (CPU) or graphical processing unit (GPU), or a proprietary, purpose-built design. Multiple controllers 604 can operate in tandem. The multiple controllers 604 can be of different types, such as a CPU and a GPU. A GPU is not restricted to only processing graphics or image data and can be used for other computations.

The memory 606 includes electronic circuitry within a computing device of the surgical robot 602 that temporarily stores data for usage by the controller 604. Examples of a main memory 306, non-volatile memory 310, and storage medium 326 are illustrated and described in more detail with reference to FIG. 3. The memory 606 can additionally include persistent data storage for storing data used by the controller 604. The memory 606 can be integrated into the controller 604 or can be a discrete component. The memory 606 can be integrated into a circuit, such as a soldered-on component of a single-board computer (SBC), or can be a removable component such as a discrete dynamic random-access memory (DRAM) stick, a secure digital (SD) card, a flash drive, a solid state drive (SSD), a magnetic hard disk drive (SSD), etc. In embodiments, the memory 606 is part of a controller 604. Multiple types of memory can be used by the surgical robot 602.

The communications interface 608 enables the surgical robot 602 to communicate with external devices and can include a wireless antenna and transceiver, or a port for receiving a cable to facilitate a wired connection. Examples of a wired connection include Ethernet, universal serial bus (USB), and proprietary connections. The communications interface 608 can be wireless, including a combination of Wi-Fi, Bluetooth, near field communication (NFC), or a cellular communications interface such as 3G, 4G, LTE, or 5G. The communications interface 608 can connect the user interface 610 to the surgical robot 602 or can facilitate access to a local network or a cloud 624 network to access a remote server and/or a database (see FIG. 7).

The user interface 610 is a means of interacting with the surgical robot 602 and can include a combination of a keyboard, computer mouse, trackball, joystick, wireless or wired gamepad, sliders, scroll wheels, touch screen, or microphone for receiving voice commands. The user interface 610 can additionally include different methods of interaction for a user (e.g., surgeon) with the surgical robot 602. The user interface 610 can accept direct inputs, such as from a joystick controlling the movement of a robotic arm. The user interface 610 can accept indirect inputs, such as commands entered on a keyboard or touch screen, e.g., adjusting the sensitivity of a joystick control or the speed of movement of the robotic arm 612 in response to joystick input. The user interface 610 can also include a screen for presenting information to a user such as patient status, imaging data, or navigation data, and speakers for providing auditory feedback. The user interface 610 can also use haptics to provide feedback to the user.

The robotic arm 612 is a mechanically actuated arm or lever with at least two degrees of freedom. The robotic arm 612 will typically include at least one end effector 614 or an imaging device 618, and can include both an end effector 614 and an imaging device 618. The robotic arm 612 can additionally be implemented to replace the end effector 614 to facilitate multiple functions and operation of a variety of surgical tools. Example surgical tools 154 are illustrated and described in more detail with reference to FIG. 1. The robotic arm 612 can be manually controlled or operated in an autonomous or semi-autonomous mode. The surgical robot 602 can have one robotic arm 612 or multiple robotic arms 612, each of which can be operated independently by one or more users or autonomous systems (e.g., an AI) or a combination of users and autonomous systems.

The end effector 614 is a tool or device located at or attached to an end of the robotic arm 612 for interacting with the patient's body or a physical object. The end effector 614 can be a surgical tool intended for acting upon or within the patient's body, or can be a gripping device for securing a separate surgical tool to the robotic arm 612. The end effector 614 can be permanently affixed to the end of the robotic arm 612 or can be detachable to allow for a system of interchangeable end effectors 614, which can alternatively be selected and swapped by a single robotic arm 612 or multiple robotic arms 612.

The sensor 616 is a measurement tool for monitoring a characteristic or metric associated with the surgical robot 602, the end effector 614, or the patient. The sensor 616 can be discrete or part of an array or assembly, such as an array of force transducers integrated into the end effector 614 to monitor the forces applied to the patient's body. One or more of the sensors 616 can include an electrophysiologic sensor, a temperature sensor, a thermal gradient sensor, a barometer, an altimeter, an accelerometer, a gyroscope, a humidity sensor, a magnetometer, an inclinometer, an oximeter, a colorimetric monitor, a sweat analyte sensor, a galvanic skin response sensor, an interfacial pressure sensor, a flow sensor, a stretch sensor, a microphone, or a combination thereof. The sensors 616 can be integrated into the operation of the surgical robot 602 or can monitor the status of the patient's body.

Data acquired by the sensors 616 can be used to train a machine learning (ML) model used by the surgical robot 602 or an AI to control the surgical robot 602. An example ML model 216 is illustrated and described in more detail with reference to FIG. 2. In some embodiments, ML model 216 is trained using reference patient data. In embodiments, the surgical robot 602 capture one or more images of an anatomy of a patient using one or more imaging devices 618. The imaging devices 618 refer to any device capable of collecting data that can be used to create an image, or a representation of a physical structure or phenomena. In embodiments, a computer system (e.g., computer system 300) causes the capture of one or more images of an anatomy of a patient using the imaging devices 618.

An imaging device 618 can include any device capable of detecting sound or electromagnetic waves and assembling a visual representation of the detected waves. Imaging devices 618 can collect waves from any part of the electromagnetic spectrum or sounds at any range of frequencies, often as a matrix of independently acquired measurements that each represent a pixel of a two- or three-dimensional image. These measurements can be taken simultaneously or in series via a scanning process or a combination of methods. Some pixels of an image produced by an imaging device 618 can be interpolated from direct measurements representing adjacent pixels in order to increase the resolution of a generated image. Example imaging devices (e.g., monitors 112, imaging system 136) are illustrated and described in more detail with reference to FIG. 1.

The imaging devices 618 can receive or generate imaging data from a plurality of imaging devices 618. The plurality of imaging devices 618 can include, for example, cameras attached to the robotic arm 612, cameras mounted to the ceiling or other structure above the surgical theater, cameras mounted on a tripod or other independent mounting device, body cameras worn by the surgeon or other surgical staff, cameras incorporated into a wearable device, such as an augmented reality device like Google Glass, Microsoft HoloLens, etc., cameras integrated into an endoscopic, microscopic, laparoscopic, or any other camera or imaging devices 618 (e.g. ultrasound) present in the surgical theater. The imaging device 618 can include any algorithm or software module capable of determining qualitative or quantitative data from medical images, which can be, for example, a deep learning algorithm that has been trained on a data set of medical images. An imaging device 618 can further refer to a device used to acquire medical imagery by any means including magnetic resonance imaging (MRI), computed tomography (CT), X-ray, positron emission tomography (PET), ultrasound, arthrography, angiography, myelography, etc.

The implant 620 is a structure embedded within the body of a patient. The implant 620 can consist of one piece, or can include multiple implant components 622. Surgical implantation is described in more detail with reference to FIGS. 4A-4B. The implant can be rigid, flexible, or combine both rigid and flexible components. The implant 620 can be made of synthetic materials such as biocompatible metals, metal alloys, plastics, resins, ceramics, etc., or can alternatively be made of organic components such as tissues harvested or derived from humans or animals. In embodiments, an implant 620 can include both organic and inorganic implant components 622. Implants 620 can be customized to fit a patient's unique physiology or to perform a specific function. Implants 620 can provide reinforcement to a patient's physiology or can replace, repair, or improve the function or performance of a part of the patient's body, such as replacing a knee joint or inserting a stent to open a vein or block off an aneurism. An implant 620 can also be a prosthetic or therapeutic device that is attached to the patient's body. An implant 620 is characterized by being surgically attached to the patient, however, the entirety of the implant 620 need not be fully embedded within the patient, and part or all of the implant 620 can be exposed even after patient recovery. In such cases, implant 620 and implant components 622 will relate to parts of such implants 620 that are in contact with the patient.

An implant component 622 is a discrete part or subassembly of an implant 620. An implant component 622 can be made of any biocompatible material that will not illicit an immune response from the patient. Biocompatible materials can be organic or inorganic. Examples of inorganic biocompatible materials include metals such as titanium, metal alloys such as titanium alloys, stainless steel, and cobalt-chromium alloy, ceramics such as zirconia and bioglass, thermoplastics such as polyvinylchloride (PVC), polyethylene (PE), polypropylene (PP), polytetrafluoroethylene (PTFE), and polymethylmethacrylate (PMMA), and other resins and materials including alumina, hydroxyapatite, medical-grade silicone, trimethyl carbonate, TMC NAD-lactide, etc. Implant components 622 can additionally include organic structures such as organs harvested from human or animal donors or tissues and compounds that can be grown or otherwise synthesized in a lab. An implant 620 can consist of a single implant component 622. Implant components 622 can be customizable.

The cloud 624 is a distributed network of computers including servers and databases. The cloud 624 is implemented using components of the example computer system 300 illustrated and described in more detail with reference to FIG. 3. The cloud 624 facilitates communication links among the components of the system 600. The cloud 624 can be a wired and/or a wireless network. The cloud 624, if wireless, can be implemented using communication techniques such as Visible Light Communication (VLC), Worldwide Interoperability for Microwave Access (WiMAX), Long Term Evolution (LTE), Wireless Local Area Network (WLAN), infrared (IR) communication, Public Switched Telephone Network (PSTN), radio waves, and other communication techniques known in the art (see FIG. 3). The cloud 624 can be a private cloud 624, where access is restricted by isolating the network such as preventing external access, or by using encryption to limit access to only authorized users. Alternatively, a cloud 624 can be a public cloud 624, where access is widely available via the internet. A public cloud 624 may not be secured or may include limited security features.

A patient database 626 stores patient data including electronic medical records, diagnosed conditions, patient-specific baseline values such as heart rate, blood pressure, etc., and medical imaging data. The patient database 626 can additionally include personal identifiable information, insurance and billing information, personal contact information, and emergency contact information. The patient database 626 can also contain legal documentation such as consent to perform a procedure. The patient database 626 can further include familial relationships and genetic data to facilitate a comprehensive family history. In some aspects of the present invention, patient database 626 stores medical images that can be used by the implant module 634, route planning module 636, simulation module 638, and/or procedure module 640 to determine aspects of the patient's anatomy that can affect the procedure, implant 620, or implant components 622. The medical images can additionally include annotations from a practitioner and/or algorithm that can indicate tissue types, structures, and/or other anatomical features which can be used by the implant module 634, route planning module 636, simulation module 638, and/or procedure module 640 to modify the procedure, implant 620, or implant components 622.

A procedure database 628 can store data related to surgical or therapeutic procedures including the type of procedure, actions taken during the procedure, what is treated by the procedure, possible contraindications or complications, and resources required such as personnel, hard goods, and consumables. The procedures can include the installation of one or more implants 620 and can include data such as the type of implant 620, number of implant components 622, and manner in which the implant 620 and implant components 622 were installed. The procedure database 628 can additionally store route data, which can include at least one incision site, at least one implant site, and one or more routes through the patient from the one or more incision sites to the one or more implant sites. The data can additionally include parameters of each path, such as the maximum dimensions of implants 620 or implant components 622 that can be accommodated. When multiple routes exist, a score or rank can be assigned to prioritize preferred routes. Preferred routes will generally accommodate implants 620 or implant components 622 with larger dimensions, or alternatively provide greater margins. Similarly, preferred routes will avoid sensitive tissues, such as blood vessels, nervous tissues, organs, etc.

An implant database 630 stores data related to one or more implants 620. The implant 620 data can include the type of implant 620, the location where the implant 620 is installed, the number and type of implant components 622, and specific properties of the implant components 622 including dimensions, materials, and manufacturing methods. The implant 620 data can additionally include physical characteristics such as hardness, flexibility, etc. The implant database 630 can additionally include data related to the procedures used to install the implants 620, patient information about the patients in whom the implants 620 are installed, and patient outcomes. The implant database 630 can be populated by a separate system that customizes the implant 620 or implant components 622, or by a database such as a third-party source that can include the manufacturer of an implant 620 or implant components 622.

The base module 632 uses at least one imaging device 618 to acquire one or more images of a patient, specifically the surgical site encompassing the location where the implant 620 is to be installed. The base module 632 is implemented using computer hardware, computer software, computer firmware, or a combination thereof, e.g., as illustrated and described in more detail with reference to FIG. 3. The implant module 634 is triggered, receives the image data, and queries the implant database 630. The implant module 634 is implemented using computer hardware, computer software, computer firmware, or a combination thereof, e.g., as illustrated and described in more detail with reference to FIG. 3. In some embodiments, the system 600 generates a virtual anatomy of the patient based on the one or more images. For example, the virtual anatomy may comprise a virtual incision site and a virtual implant site corresponding to the incision site and the implant site, respectively.

In embodiments, the system 600 segments the surgical implant 620 into multiple implant components 622 based on one or more images of the patient's anatomy. Each implant component 622 has a size and a shape compatible with the implant site. The surgical implant design is selected and is segmented into one or more implant components 622. In some embodiments, the system 600 segments a surgical implant design or a three-dimensional virtual implant model (e.g., a computer-aid design (CAD) model, virtual solid models, surface models, etc.) of the surgical implant into multiple virtual implant components based on one or more images of the patient's anatomy. in some embodiments, the system 600 segments the surgical implant based on a segmentation plan. The segmentation plan can be generated based on the design of the implant, features at the implantation site, size of the implantation site, etc. The segmentation plan can be implemented to segment the implant into a target number of sub components (e.g., two, three, four, five separate virtual implant components) capable of being at least partially assembled within the body. For example, the segmentation can include partitioning or cutting an implant or virtual model of the implant into individual components. The locations and geometry of the segmentation (e.g., segmentation along a plane or datum) can be selected based on user input, selected delivery paths, etc. For example, an implant can be segmented into components that are smaller than the size (e.g., cross-sectional size) of a delivery path. The segmented components can include connectors, such as threaded members, threaded holes, pins, or couplers, used to couple together the components. Multiple simulations can be performed each having different segmented implants. Postoperative loading can be analyzed to determine the segmentation locations such that the assembled implant is configured to withstanding planned loading.

Each virtual component of a virtual implant model has a virtual size and a virtual shape compatible with a virtual implant site corresponding to the implant site. In some embodiments, a machine learning model (e.g., ML model 216, as illustrated in FIG. 2) may be used to perform segmentation of the surgical implant 620, the surgical implant design, or the three-dimensional virtual implant model of the surgical implant. In some embodiments, the system 600 designs virtual implant components based on the images or virtual anatomy of the patient. For example, the virtual implant components may be designed to form a three-dimensional virtual implant model representing the surgical implant.

Each physical implant component 622 or virtual implant component is then assessed for whether it needs to be modified. Physical implant components 622 or virtual implant components are modified as necessary, and then the customized implant components 622 are saved to the implant database 630. The customized implant components 622 are received by the base module 632, and the route planning module 636 is triggered. The route planning module 636 receives image data and data from the procedure database 628, identifies at least one implant site and at least one incision site. In some embodiments, a machine learning model (e.g., ML model 216, as illustrated in FIG. 2) may be used to perform identification of the at least one implant site and the at least one incision site.

The route planning module 636 generates possible routes or delivery paths through which implant components 622 can be moved from the incision site to the implant site. In some embodiments, the route planning module 636 identifies at least one virtual implant site and at least one virtual incision site, and generates possible routes through which the virtual implant components can be moved from the virtual incision site to the virtual implant site. In some embodiments, a machine learning model (e.g., ML model 216, as illustrated in FIG. 2) may be used to perform identification of the at least one virtual implant site and the at least one virtual incision site. The route planning module 636 is implemented using computer hardware, computer software, computer firmware, or a combination thereof, e.g., as illustrated and described in more detail with reference to FIG. 3.

Constraints or other selection criteria are determined based upon parameters of the implant components 622 including the dimensions of the largest implant components 622, dimensions, curvature, or other features of the patient's anatomy, dimensions, curvature, or other features of the available routes, capabilities of the robotic surgical system or other delivery instruments, maneuverability of the robotic surgical system or other delivery instruments, availability of surgical tools, time constraints of the patient or physician, or other factors. Constraints for virtual implant components may be determined based upon parameters of the virtual implant components including the dimensions of the largest virtual implant components, dimensions, curvature, or other features of the patient's virtual anatomy, dimensions, curvature, or other features of the available routes, capabilities of the robotic surgical system or other delivery instruments, maneuverability of the robotic surgical system or other delivery instruments, availability of surgical tools, time constraints of the patient or physician, or other factors. A route is selected and is evaluated for compliance with the identified constraints. Compliant routes are added to a list of valid routes, and the list of valid routes is saved to the procedure database 628 and received by the base module 632.

In embodiments, the system 600 simulates the passage of multiple virtual implant components via one or more routes by the surgical robot 602. For example, the simulation module 638 is triggered, receiving route planning data and the customized implant components 622. For each route, simulations are performed such that each implant component 622 is inserted through the identified route and then installed at the implant site. If the implant component 622 is able to navigate from the incision site to the implant site and can be assembled into the implant 620, the route is added to a list of verified routes. In an example, the human organs are observed from the inside of the abdominal cavity, and the use of various instruments to grasp, cut or clip the organs is simulated. In an example, a simulator uses a computer screen displaying a three-dimensional graphic of the organs being operated on. Surgical tools can be connected to motion sensors and haptic or tactile feedback mechanisms in the simulation.

For each route, virtual simulations may be performed such that each virtual implant component is inserted into the anatomy through the virtual incision site and passed along the identified route. The virtual implant components may then be assembled into the surgical implant design or three-dimensional virtual implant model and virtually installed at the virtual implant site. If the virtual implant component is able to navigate from the virtual incision site to the virtual implant site and can be assembled into the surgical implant design or three-dimensional virtual implant model, system 600 may manufacture the surgical implant according to the segmented surgical implant design or segmented three-dimensional virtual implant model. In some embodiments, virtual simulations may be performed for assembly of the virtual implant components into the surgical implant design or the three-dimensional virtual implant model. Virtual simulations may be performed for the surgical implant design or the three-dimensional virtual implant model positioned at the virtual implant site. For example, the system 600 can virtually simulate delivery of virtual components of the virtual implant model along corresponding ones of multiple delivery paths in the digital anatomical model within the XR surgical simulation environment. The system 600 or user can select a set of the delivery paths for delivery of physical components of the surgical implant to the implant site based on simulating the delivery of the virtual components. The physical components correspond to the virtual components. In some embodiments, the physical components are modified during or after manufacturing based on the virtual components. Any number of simulations can be performed using different multi-component implant models, delivery paths, etc. The system 600 can then robotically move the physical components of the surgical implant using the set of delivery paths. The system 600 can also robotically assemble the surgical implant within the patient.

In some embodiments, the system 600 may determine a predicted patient outcome based on the virtual simulations. For example, the system 600 may determine a score for the predicted patient outcome for each delivery path. In some embodiments, the score may reflect a success rate, a risk of damage to the patient, a healing outcome, or other metric. In some embodiments, the route or delivery path may be selected based on the virtual simulation or the score for the predicted patient outcome. In some embodiments, the system 600 may rank the scores for the predicted patient outcomes and may use the ranking to select the routes or delivery paths.

The simulation results including the verified routes or the scores are received by the base module 632 and can additionally include data describing failures that occurred during simulation of routes not included in the list of verified routes. In some embodiments, the system 600 may select at least one of the routes or delivery paths based on the virtual simulation or the simulation results, including the verified routes or the scores. In some embodiments, a machine learning model (e.g., ML model 216, as illustrated in FIG. 2) may be used to perform the selection of the routes or delivery paths. If there are no verified routes, the simulation results can be sent to the implant module 634 for further modification of the implant components 622, otherwise the procedure module 640 is triggered. The procedure module 640 receives the implant components 622 and verified routes and selects a verified route through which each implant component 622 is inserted. The procedure module 640 is implemented using computer hardware, computer software, computer firmware, or a combination thereof, e.g., as illustrated and described in more detail with reference to FIG. 3. The system 600 can generate an assembly plan for assembling the implant. The assembly plan can include, for example, order to assembling components, assembly parameters (e.g., minimum forces, minimum torques maximum forces, maximum torques, tool speeds, etc.), tools, and other data generated based on, for example, routes or delivery paths, configuration of the implantation site and surrounding features, the configuration and capabilities of the surgical robot, user input, etc.

If the implant component 622 cannot be successfully inserted via the selected route, an alternate route can be selected if available. A procedure status is generated and is received by the base module 632. The procedure status can indicate whether one or more routes require modification, thus triggering the route planning module 636, or the procedure status can indicate whether the procedure is complete. If the procedure is complete, then the patient's procedure ends, otherwise the procedure module 640 will be triggered until the procedure is completed.

The implant module 634 receives image data from the base module 632. The implant module 634 additionally queries the implant database 630 for implant 620 designs and selects at least one implant 620 design. Alternatively, a unique or customized implant 620 design can be generated that is not based upon the designs from the implant database 630. The implant 620 is then segmented into at least one implant component 622. The size and shape of the implant components 622 can be based upon the patient's anatomy as represented by the image data.

If the implant component 622 cannot be successfully inserted via the selected route, or if all routes or delivery paths fail to meet a selection criterion such as a route constraint, the system may make certain modifications. For example, the system 600 may modify a particular route such that the implant component 622 can be passed form the incision site to the implant site along a route. The route modifications may comprise routing around locations through which the implant component 622 is not able to pass. In embodiments, the system 600 modifies an implant component or causes the implant component to be modified such that the implant component can be passed from an incision site to an implant site along a route. For example, each implant component 622 is selected and evaluated for whether additional modification is required, and the implant components 622 are modified when necessary. In embodiments, modifying an implant component includes adding a flexible portion to the implant component. For example, modifications can include adding flexible materials or features, such as to a rod, to allow the rod to articulate to navigate through a narrow, curving installation route. Modifications can include replacing a solid structure with a mechanical structure such that the implant component 622 can begin the procedure with a collapsed profile to allow navigating along the selected installation route and then can be expanded when the implant component 622 arrives at the implant site. When all implant components 622 have been modified as necessary, the customized implant 620 and implant component 622 designs are saved to the implant database 630 and the implant components 622 are sent to the base module 632. The implant module 634 can additionally receive data from the simulation module 638 if no valid routes can be identified to navigate one or more implant components 622 from the incision sites to the implant site.

If a virtual implant component cannot be successfully inserted into the virtual anatomy via the selected route, an alternative route can be selected if available, or system 600 may modify the route, the virtual implant component, the virtual segmentation of the surgical implant design, or the incision site and the implant site. The system 600 may modify a particular route such that the virtual implant component can be passed form the virtual incision site to the virtual implant site along a route. The route modifications may comprise routing around or otherwise excluding locations through which the virtual implant component is not able to pass. The virtual implant component may be modified, for example, by replacing a solid structure with a mechanical structure within the surgical implant design. In some embodiments, modifications can include adding flexible materials or features, such as to a rod, to the surgical implant design. In some embodiments, the segmentation of the virtual implant component may be modified. For example, system 600 may modify the number of segments making up the surgical implant design, the shape of the segments, the positioning of the segments, or other features of the segmentation. In some embodiments, the incision site and the implant site may be modified based on the virtual simulation.

In embodiments, the system 600 determines one or more routes from an incision site to an implant site based on route constraints. For example, the route planning module 636 receives image data acquired from at least one imaging device 618 and the implant components 622 from the base module 632. The route planning module 636 additionally queries the procedure database 628 for data on medical or surgical procedures including the installation of one or more implants 620. At least one implant site and at least one incision site are identified, and possible routes through which the implant components 622 can be navigated are generated. Constraints are identified for the one or more implant components 622 such as their maximum physical dimensions and can additionally include safety margins. A route is selected from the generated routes and is evaluated for compliance with the identified constraints. A route may be noncompliant if it cannot accommodate the largest implant components 622 or the route does not provide adequate safety margins, which could result in harm to sensitive tissues during installation of implant components 622. If the route is compliant it is added to a list of valid routes and the remaining routes are assessed. When all routes have been assessed, the valid routes are saved to the procedure database 628 and are sent to the base module 632.

The simulation module 638 receives route data generated by the route planning module 636 and implant components 622 customized by the implant module 634 from the base module 632. For each route, simulations are performed for the insertion of each implant component 622. In embodiments, a route is identified via which an implant component can be passed from the incision site to the implant site by the surgical robot 602 based on simulations. If all of the implant components 622 are able to navigate from the incision site to the implant site without encountering an issue, such as being physically unable to fit through the space or by encroaching on clearances required for sensitive tissues, and the implant components 622 can be assembled into an implant 620, the route is added to a list of verified routes. The process is repeated for all routes and the verified routes are saved to the procedure database 628 and sent to the base module 632. In addition to the verified routes, data from the failed routes, such as the implant components 622 that were unable to navigate via each route and the manner in which they failed, can be sent to the base module 632.

The procedure module 640 receives implant components 622 and verified routes from the base module 632. A route is selected from the list of verified routes and an implant component 622 is inserted via the route. If the insertion is successful, the process is repeated for all remaining implant components 622. If the insertion of an implant component 622 is unsuccessful, another route is selected from the list of verified routes. When all implant components 622 have been inserted, the implant components 622 are assembled to form the implant 620. A procedure status is generated and sent to the base module 632. The procedure status can include the stage of the procedure, such as whether the procedure has been completed or is in progress, and can also include information such as whether all verified routes have been attempted unsuccessfully. In such cases, data relevant to the failures can be provided to the base module 632, such as data about the implant component 622 that was unsuccessfully inserted, and details of the attempt, such as where the implant exceeded allowable margins or contacted surrounding tissues.

The system 600 can perform simulations using virtual models that can include two or three-dimensional models to evaluate, for example, implant assembly, implant design, one or more steps of a surgical procedure (or an entire procedure), predicted events, outcomes, etc. The simulations can be used to identify and assess implantation parameters (e.g., implantation time, implantation complexity, etc.), access paths or routes, stresses (e.g., stresses in implant components, stresses in anatomical features, etc.), strains, deformation characteristics (e.g., load deformation characteristics in implants/anatomy, load distributions in implants/anatomy, etc.), fracture characteristics (e.g., fracture toughness), fatigue life, etc. The virtual model can include exemplary implant components, exemplary assembled implants, portions of a patient's anatomy, exemplary end effectors, exemplary instruments, exemplary access tools, or the like.

The simulations can be generated using three-dimensional models, surfaces, and virtual representations. The simulations can be generated by CAD software, finite element analysis (FEA) software (e.g., analyze stress in components), and robotic control software/programs based on patient data (e.g., images, scans, etc.), implant design data, or the like. A user can view, manipulate (e.g., rotate, move, etc.), modify, set parameters (e.g., boundary conditions, properties, etc.), and interact with the models. The control parameters, robotic kinematics, and functionality can be used to generate the simulations. In some embodiments, models of implants, installation tool, insertion instruments, end effectors of a robotic system, etc. are used to perform virtual procedures on virtual anatomical models. Virtual simulations of surgical procedures can be performed in which-user selected robotic surgical steps and physician steps are used to generate, modify, and select surgical plans, surgical robot configurations, or the like.

Pre-operative simulations can be performed for different surgical robots using pre-operative patient data (e.g., pre-operative scans, images, etc.). A surgical robot for performing a surgical procedure or portion thereof can be selected based on the simulation(s). This allows a healthcare provider to select a surgical robot suitable for a particular procedure for assembling implants. Additionally, the simulations can be used to generate, modify, and/or verify surgical plans. In some embodiments, a configuration of the surgical robot is selected based on the simulations. For example, multiple simulations can be performed for a surgical robot in different configurations (e.g., the surgical robot having different end effectors) and using different surgical techniques for assembling implants. The healthcare provider can select the surgical robot configuration and surgical plan based, at least in part, on the simulations. End effectors and tools of the surgical robot, imaging equipment, and manual equipment can be selected based on the simulations.

FIG. 7 illustrates a structure of an example database for performing route planning for robotic surgical implant installation, in accordance with one or more embodiments. FIG. 7 shows the patient database 626. The patient database 626 includes data about one or more patients and can include electronic medical records. Likewise, embodiments of the patient database 626 can include different and/or additional components or can be connected in different ways.

The patient database 626 can include personally identifiable information such as name, date of birth, address, insurance information, etc. A patient database 626 can additionally include information about a patient's health or medical history such as diagnosed conditions, allergies, medications, normal baseline vital sign ranges for the patient, etc. The patient database 626 can be populated by medical professionals such as a patient's physician, specialists such as surgeons, therapists, or any other medical professionals including nurses, emergency medical technicians, paramedics, etc. The patient database 626 additionally stores images acquired by the base module 632 using at least one imaging device 618 and can also store data related to the patient from the implant module 634, route planning module 636, simulation module 638, and procedure module 640.

The patient database 626 is used by the implant module 634, route planning module 636, simulation module 638, and procedure module 640. The patient database 626 can include, for example, medical images produced by imaging device 618, which can be, for example, X-rays, CT (computed tomography) scan, positron emission tomography (PET) scan, MRI (magnetic resonance imaging), ultrasound, or nuclear medicine imaging. Medical images can further include still images or videos from a camera either external or internal to the patient, such as an endoscope, laparoscope, etc. Medical image data can include metadata from the images, such as the specific model of equipment used to generate the image, the date and time the image was taken, the geographic location of the image, the anatomical location of the image, and the practitioner(s) who performed the imaging.

Additionally, the medical image data can include annotations from a practitioner and/or algorithm that indicate tissue types, structures, and/or other anatomical features. The patient database 626 can contain 3D anatomical representations of the user generated by medical images, such as, for example, using the cross-sectional imaging data provided by an MRI device to convert pixels from individual cross-sections into voxels defining a 3D volume by extrapolating the volume between at least two pixels of at least two medical images, wherein the volume can be determined by the distance between cross-sections that the MRI machine generated.

The 3D anatomical representation can further be generated by combining cross-sectional images from two or more axial planes of an imaging modality, such as MRI. In one example, the patient database includes an MRI scan of a male patient, age 46. The MRI can show portions of the hip joint that need to be replaced with prosthetic implants. The patient data can also include a prescription for the removal and replacement of portions of the pelvis and femur that form the patient's hip joint. The patient database 626 can include a 3D model of the patient's hip joint and the prosthetic that needs to be implanted.

In embodiments, a visible light imaging modality is used, such as encapsulating color images, e.g., in JPEG format, where the images captured include specialty-specific acquisition context metadata. The visible-light imaging modality can be used by a surgical robot (see FIGS. 4A-4B) for performing endoscopy (including fiberoptic endoscopy or rigid scope endoscopy), angioscopy, arthroscopy, bronchoscopy, colposcopy, etc. The visible-light imaging modality can be used by a surgical robot for performing light microscopy for anatomic pathology (e.g., transmission light microscopy and reflection light microscopy for cytology or histology), surgical microscopy (e.g., images produced by an operating microscope used in cardiothoracic surgery, neurologic surgery, ophthalmic surgery, etc.), anatomic pathology, dermatology, aesthetic (cosmetic) or reconstructive plastic surgery, etc.

In embodiments, the imaging devices use a computer tomography (CT) modality to generate a two-dimensional (2D) or three-dimensional (3D) image of the scanned region of interest. The CT images are a compilation of computer-processed X-ray images taken at a range of angles around the region to produce a single cross-sectional image. The region can be moved forward within the imaging device to scan a next cross-section similarly. The cross-sectional images can be viewed side by side or stacked on top of one another to create a 3D scan of the region. In embodiments, an imaging device uses an MRI imaging modality to provide highly detailed images of tissue structures. The imaging device detects and processes the signals generated when hydrogen atoms, which are abundant in tissue, are placed in a strong magnetic field and excited by a resonant magnetic excitation pulse.

FIG. 8 illustrates a structure of an example database 628 for performing route planning for robotic surgical implant installation, in accordance with one or more embodiments. FIG. 8 shows the procedure database 628. The procedure database 628 includes data about one or more procedures. Likewise, embodiments of the procedure database 628 can include different and/or additional components or can be connected in different ways.

The data in the procedure database 628 can include the steps of the procedure and can also include a plurality of alternative steps or responses to issues or complications. The data can additionally include one or more parameters or conditions by which the procedure can be halted or aborted. The data can additionally include actions taken, measurements taken such as vital signs, and personnel involved, including the patient, the surgeon, and any other personnel and equipment used. The procedure database 628 can be populated by surgeons, nurses, or any other medical professionals or technicians and can include relevant portions of patients' electronic medical records pertaining to a procedure.

In embodiments, the procedure database 628 can additionally include patient data such as the data in patient database 626 that may be relevant to one or more procedures. Procedures can include implant procedures or therapies that involve segmentation and customization of an implant 620. The procedure database 628 can also include procedures that are not relevant to implant procedures. The procedure database 628 is used by the route planning module 636, simulation module 638, and procedure module 640. In one example, the procedure database 628 contains data on a hip joint replacement surgery. The procedure database 628 indicates a procedure for a minimally invasive robotic surgery wherein portions of the pelvis and femur that form the patient's hip joint are removed and replaced with a prosthetic implant. In such examples, the procedure data can also include instructions for a customized implant 620 and implant components 622 and can additionally include installation route data.

The procedure database 628 can additionally include one or more incision sites, one or more implant sites, and a plurality of routes between one or more incision sites and one or more implant sites. The routes can be further qualified as valid routes capable of accommodating implant components 622 for the installation of an implant 620 and can be further verified by the simulation module 638. Routes that have been verified can additionally be scored, ranked, or otherwise identified by preference based upon the routes' ability to accommodate implant components 622, which can include physical clearances or the proximity of sensitive tissues such as nervous tissues, blood vessels, organs, etc., to the route.

FIG. 9 illustrates a structure of an example database for performing route planning for robotic surgical implant installation, in accordance with one or more embodiments. FIG. 9 shows the implant database 630. The implant database 630 stores data about implants 620 and implant components 622. Likewise, embodiments of the implant database 630 can include different and/or additional components or can be connected in different ways.

The data can include the type of implant 620, the location of the implant 620, one or more implant components 622 that make up the implant 620, the materials of each implant component 622, and the properties of those materials. For example, the implant 620 materials can include one or more of any biocompatible material including alumina, bioglass, cobalt-chromium alloy, hydroxyapatite, medical-grade silicone, polyvinylchloride (PVC), polyethylene (PE), polypropylene (PP), polytetrafluoroethylene (PTFE), polymethylmethacrylate (PMMA), stainless steel, trimethyl carbonate, TMC NAD-lactide, titanium and titanium alloys, zirconia, etc. The implant 620 data can further include installation data and patient outcomes.

Figure 10:
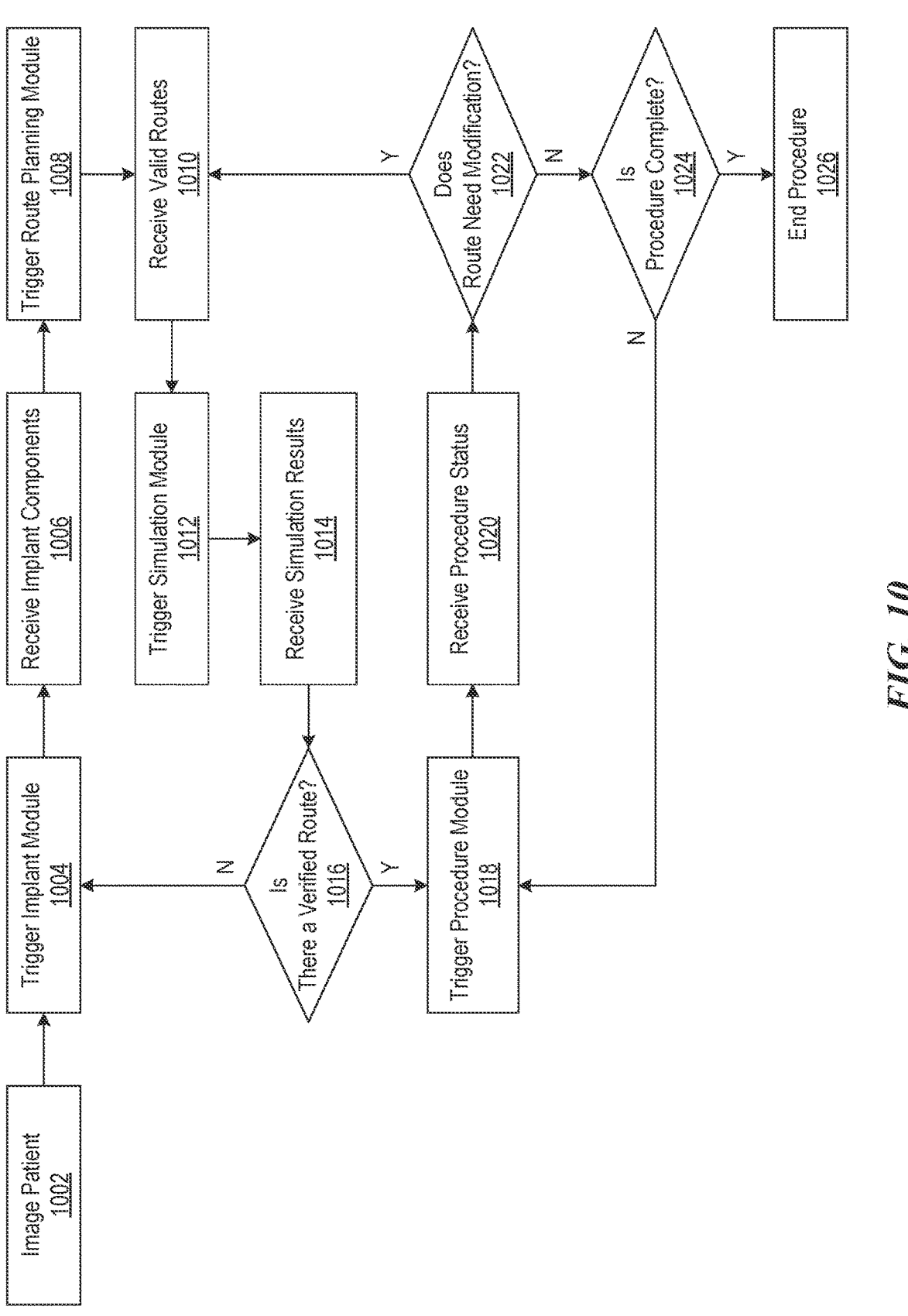
FIG. 10 is a flow diagram illustrating an example process for performing route planning for robotic surgical implant installation, in accordance with one or more embodiments.

FIG. 10 is a flow diagram illustrating an example process for performing route planning for robotic surgical implant installation, in accordance with one or more embodiments. An example operating room 102 is illustrated and described in more detail with reference to FIG. 1. In embodiments, the process of FIG. 10 is performed by the operating room system base module 632. The operating room system base module 632 is illustrated and described in more detail with reference to FIG. 6. In other embodiments, the process of FIG. 10 is performed by a computer system, e.g., the example computer system 300 illustrated and described in more detail with reference to FIG. 3. Particular entities, for example, the console 108 or the robotic surgical system 160, perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In step 1002, the base module 632 images the patient, including the location where an implant 620 is to be installed, using an imaging device 618. The imaging can be performed using at least one of any imaging methods, including both visual light and radiologic modalities. In preferred embodiments, however, at least one imaging modality is a radiologic modality such as CT, MRI, PET, etc. In some embodiments, a single imaging modality can be used, such as MRI. In other embodiments, multiple imaging modalities can be used, such as MRI, CT, and ultrasound. In some embodiments, a single image frame can be used. In other embodiments, multiple image frames can be used. When multiple image frames are used, multiple images can be used to create a higher resolution two-dimensional image. The same method can be applied in slices of varying depths, or from varying orientations, to create a three-dimensional representation of the implant site. In embodiments, imaging is performed on the right hip of a patient named John Smith using MRI. The image data can be further saved to the patient database 626.

In embodiments, the system 600 uses sound waves or acoustic energy (ultrasound imaging modality) in a frequency above human hearing (20,000 Hertz (Hz) or 20 kHz). A diagnostic sonographic scanner can be used in a frequency range of 2 to 18 MHz, hundreds of times greater than the limit of human hearing. In embodiments, X-ray imaging is performed using electromagnetic radiation of extremely short wavelength and high frequency, with wavelengths ranging from about $10^{-8}$ to $10^{-12}$ meters (m) and corresponding frequencies from about $10^{16}$ to $10^{20}$ Hz.

In embodiments, the system 600 performs one or more multi-modality analyses in which one or more multi-sensing devices (e.g., multi-modality imagers, multiple imaging machines, etc.) perform (sequentially or concurrently) multiple scans/tests, such as CT scans, radiation tests, sound tests, optical tests, acoustic tests, photoacoustic tests, combinations thereof, or the like. In embodiments, a multi-modality image can simultaneously image a target region to capture images with matching perspectives relative to the target region such that features from one image can be overlayed onto another, features from multiple images can be stitched together to form a composite image, and/or cross-image features identification can be performed. In embodiments, tests are performed during one or more scans of the target region. In a single scan test, the system 600 can concurrently perform multiple tests while moving along the tissue sample. In multiple scan tests, the system 600 sequentially performs tests during corresponding scans and/or concurrently performs multiple tests during each scan. The system 600 can perform different testing, imaging, and/or scanning protocols based on the analysis to be performed.

The system 600 can facilitate communication with another robotic surgical system, doctor, surgeon, or other medical professional by providing results (e.g., multi-modality data, raw data, visualizations of the data, and the like) from the test(s) in real time. Further, the system 600 can combine the results from imaging device(s) to provide a diagnosis of a tissue sample, target region, surgical site, or combinations thereof. In surgical procedures, the results can be automatically transmitted to a surgical robot that analyzes the results to perform one or more surgical steps. The surgical robot can request additional information from the system 600 to, for example, complete a surgical step, confirm completion of a surgical step, plan a surgical step, plan a series of surgical steps, or the like. For example, the surgical system 400 at FIG. 4A can receive multi-modality results from the system 600 to perform a multi-modality-guided robotic surgical step. In embodiments, the results are displayed via display 422 for viewing by the surgical team, as shown in FIG. 4A. Features of exemplary viewable multi-modality results are discussed in connection with FIG. 15. Additionally, or alternatively, the results can be viewable via console 420 by a user 421 of FIG. 4A while, for example, monitoring or performing one or more surgical steps.

In embodiments, the system 600 captures images of a region of interest of a patient's anatomy using a first imaging device and a second imaging device. The first imaging device uses a first imaging modality and the second imaging device uses a second imaging modality. The system 600 uses the different types of detected wavelengths individually or in combination for a variety of medical and non-medical applications. In embodiments, multi-modal image fusion is performed. A first set of (X,Y) data points and a second set of (X,Y) data points are fused by amalgamating two or more images from single or multiple imaging modalities, such as positron emission tomography, single photon emission computed tomography, computed tomography, or magnetic resonance imaging, into a single distinct image having more-detailed anatomical and spectral information. The benefits of the embodiments are to improve the quality of an image while preserving the most desirable and relevant characteristics of each in order to make the image more usable for clinical diagnosis and treatment procedures. In embodiments, feature processing, machine learning, and sparse representation are used to learn informative characteristics that portray the patterns and regularities in each set of data points.

In step 1004, the base module 632 triggers the implant module 634, which receives the image data acquired from at least one imaging device 618. In embodiments, the ML system 200 illustrated and described in more detail with reference to FIG. 2 extracts features from the images and uses a combination of digital image processing, computer vision, and image segmentation to partition an image into multiple image segments, also known as image regions or image objects (sets of pixels). The embodiments simplify and/or change the representation of the image into segments that are more meaningful and easier to analyze. The methods disclosed herein can be used to locate objects and boundaries (lines, curves, etc.) in images. The methods can assign a label to each pixel in an image such that pixels with the same label share certain characteristics. In embodiments, the set of segments generated cover the entire image, or at least a set of contours extracted from the image. Each of the pixels in a segment can be similar with respect to some characteristic or computed property, such as color, intensity, or texture. Adjacent segments are different with respect to the same characteristic(s). When applied to a stack of images in medical imaging, the resulting contours after the image segmentation can be used to create two-dimensional (2D) or three-dimensional (3D) reconstructions with the help of interpolation algorithms, such as marching cubes.

In embodiments, the implant module 634 improves in identification of the image segments over time. The implant module 634 can detect edges of the sample from the reference segment. For example, the implant module 634 identifies edges from a captured image, Picture 1, defining bone tissue, as the reference segments using the ML system 200. In embodiments, edges can even be manually identified by a doctor over the user interface. For example, the implant module 634 identifies edges defined by a contrast in the magnitude of light of gray-scale images. Successively, the implant module 634 can label a segment enclosed by the identified edges by comparing the detected images to similar previously acquired images. For example, the implant module 634 labels a segment bound by the detected edges by comparing the image with a database of similar images, and determining the segment that constitutes bone tissue. The segment can further be identified as a specific structure, such as the femur of a patient's right leg.

The implant module 634 further queries the implant database 630 for implant designs and selects an implant design. The implant design is optionally virtually segmented into a plurality of implant components 622. Each implant component 622 is evaluated for further customization and the implant components 622 are modified if necessary. When all implant components 622 have been modified, the customized implant 620 and implant components 622 are saved to the implant database 630.

In step 1006, the base module 632 receives the customized implant components 622 from the implant module 634. In embodiments, at least one implant component 622 is customized to be expandable. This customization changes the implant component 622 from a solid volume measuring 3 cm×3 cm×5 cm such that in its collapsed form the implant component 622 has a volume of 1 cm×1 cm×5 cm. In other embodiments, an implant component 622 material is changed from a titanium metal alloy to a more flexible polypropylene. In further embodiments, an implant component 622 is further segmented into two segments to accommodate installation via the route parameters.

In step 1008, the base module 632 triggers the route planning module 636, which receives from the implant module 634 the image data acquired from the at least one imaging device 618 and the implant components 622. In embodiments, the image data is MRI imagery of the abdomen and proximal legs of patient John Smith to encompass the hips, where an implant will be installed, and probable incision sites. Alternatively, the route planning module 636 receives a reference to a location in the patient database 626 where the image data is stored. In embodiments, a series of MRI images of John Smith's right hip is sent to the route planning module 636. Additionally, the route planning module 636 receives information about the implant components 622 that, when assembled, will form the implant 620 to be installed to reconstruct John Smith's right hip joint.

The route planning module 636 further queries the procedure database 628 and uses the data to identify an implant site and at least one incision site. The route planning module 636 generates routes between the at least one incision site and the at least one implant site, identifying constraints for the implant components 622 such as identifying the maximum dimensions of the largest implant components 622. Similarly, the route planning module 636 identifies the clearance or margins required to navigate the implant components 622 safely through the patient's body. Each route is evaluated for compliance with the constraints, and those that are compliant are added to a list of valid routes. When all routes have been assessed, the list of valid routes is saved to the procedure database 628. In embodiments, detailed data can be saved for each of the analyzed routes, such as the minimum clearances for compliant routes, which routes were noncompliant, and the reason the routes were noncompliant.

In embodiments, the system 600 (see FIG. 6) determines the route constraints or performs route planning based on a clearance at an implant site required for assembly of the surgical implant 620 from the implant components 622. For example, in step 1010, the base module 632 receives the valid routes from the route planning module 636. The routes include at least one path between an incision site and the implant site. The routes are capable of accommodating the implant component 622 constraints, such as maximum dimensions, which can represent the maximum height or width of implant components 622. The routes can additionally accommodate varying clearance margins depending on the type of tissues along the selected route and can further identify tissue sensitivities and required clearances to avoid possible injury of sensitive tissues during installation of implant components 622. In embodiments, five valid routes are received, each capable of accommodating all of the implant components 622.

In step 1012, the base module 632 triggers the simulation module 638, which receives the valid route data and the implant components 622. For each route and each implant component 622, simulations are performed that include navigating each implant component 622 from the incision site to the implant site via the route selected by the route planning module 636. For each implant component 622, the simulation module 638 determines whether the implant component 622 can be successfully navigated to the implant site without becoming stuck or without encroaching on clearances of anatomical structures such as sensitive tissues, including blood vessels and nerve tissue. When simulations have been completed for the navigation of all implant components 622 to the implant site via the selected route, the simulation module 638 simulates the assembly of the implant components 622 within the patient to form a completed implant 620. Routes capable of facilitating the movement and assembly of all implant components 622 are added to a list of verified routes.

In step 1014, the base module 632 receives the simulation results from the simulation module 638. The simulation results can include a list of verified routes. The simulation results can additionally include data such as errors or other issues identified during the simulations. In embodiments, the simulation results include three verified routes. In further embodiments, the simulation results include issues encountered during insertion and assembly of the implant components 622, such as an implant component 622 trespassing within the 0.5 cm margin of a nerve and therefore being unable to safely navigate to the implant site, thus resulting in a failed simulation.

In step 1016, the base module 632 determines whether there is at least one verified route that can accommodate the insertion, navigation, and assembly of all implant components 622. If no routes could be verified by the simulation module 638, the base module 632 determines that there are no verified routes and sends received simulation results, including detailed data on the errors encountered, to the implant module 634 for further modification of the implant components 622.

In embodiments, the system 600 (see FIG. 6) inserts each implant component 622 into a patient's anatomy via a route by the surgical robot 602. For example, in step 1018, the base module 632 triggers the procedure module 640, which receives the implant components 622 and verified routes. The procedure module 640 selects a route from the verified routes and selects and inserts an implant component 622. If insertion of the implant component 622 is unsuccessful, the procedure module 640 selects a different verified route, if available. The procedure module 640 repeats the insertion process until all implant components 622 have been successfully inserted into the patient and then assembles the implant components 622 into an implant 620.

If an implant component 622 could not be inserted via any of the verified routes or the implant components 622 could not be assembled, the procedure module 640 generates a procedure status indicating that the procedure is still in progress and that an issue has been encountered preventing the insertion of an implant component 622. The procedure status can additionally include detailed information about the failed insertion of the implant component 622 such as identification of the implant component 622, dimensions of the implant component 622, the locations where the implant component 622 was unable to pass through the patient, and structures that the implant component 622 was unable to navigate around. Alternatively, if the implant components 622 were successfully inserted and assembled into an implant 620 and the procedure is complete, the procedure module 640 generates a procedure status indicating that the implant 620 has been successfully installed and the installation procedure is complete.

In embodiments, the system 600 (see FIG. 6) determines that a particular implant component is unable to be passed from the incision site to the implant site via any of the routes. The system 600 determines one or more locations along the routes through which the particular implant component is unable to be passed. For example, in step 1020, the base module 632 receives a procedure status from the procedure module 640. The procedure status can indicate that the procedure is still in progress and that an implant component 622 was unable to navigate any of the available verified routes. The procedure status can additionally include details about the failed insertion of the implant component 622 such as identification of the implant component 622, dimensions of the implant component 622, the locations where the implant component 622 was unable to pass through the patient, and structures that the implant component 622 was unable to navigate around. Alternatively, the procedure status can include a success message indicating that the procedure has been successfully completed.

In embodiments, the system 600 (see FIG. 6) modifies a particular route such that a particular implant component can be passed from the incision site to the implant site along the particular route. The particular route excludes the one or more locations that the particular implant component is unable to navigate. For example, in step 1022, the base module 632 determines whether modification of one or more routes is necessary. Modification of a route can be required if one or more implant components 622 are unable to be navigated through any of the available verified routes or if the implant components 622 cannot be assembled within the patient. If a route requires modification, the base module 632 triggers the route planning module 636 and sends any available information included in the procedure status received from the procedure module 640. In embodiments, minor modifications can be required and made to an implant component 622 to facilitate successful insertion, navigation, and assembly during a procedure. Such modifications can be assumed to have been attempted during the installation attempt.

In step 1024, the base module 632 determines whether the procedure is complete based upon the procedure status received from the procedure module 640, if the route does not required modification. The procedure is complete if the procedure status received from the procedure module 640 indicates that the implant components 622 have been successfully inserted into the patient and assembled into an implant 620 at the implant site. If the procedure is not complete, the base module 632 triggers the procedure module 640 to continue the procedure.

In step 1026, the implant 620 installation procedure ends if the procedure is complete. Ending the procedure can include any processes or procedures required to terminate the procedure, such as removing tools and materials from the patient, closing any incisions made in the patient, monitoring the condition of the patient, and further providing post-operative treatment and therapy to the patient.

Figure 11:
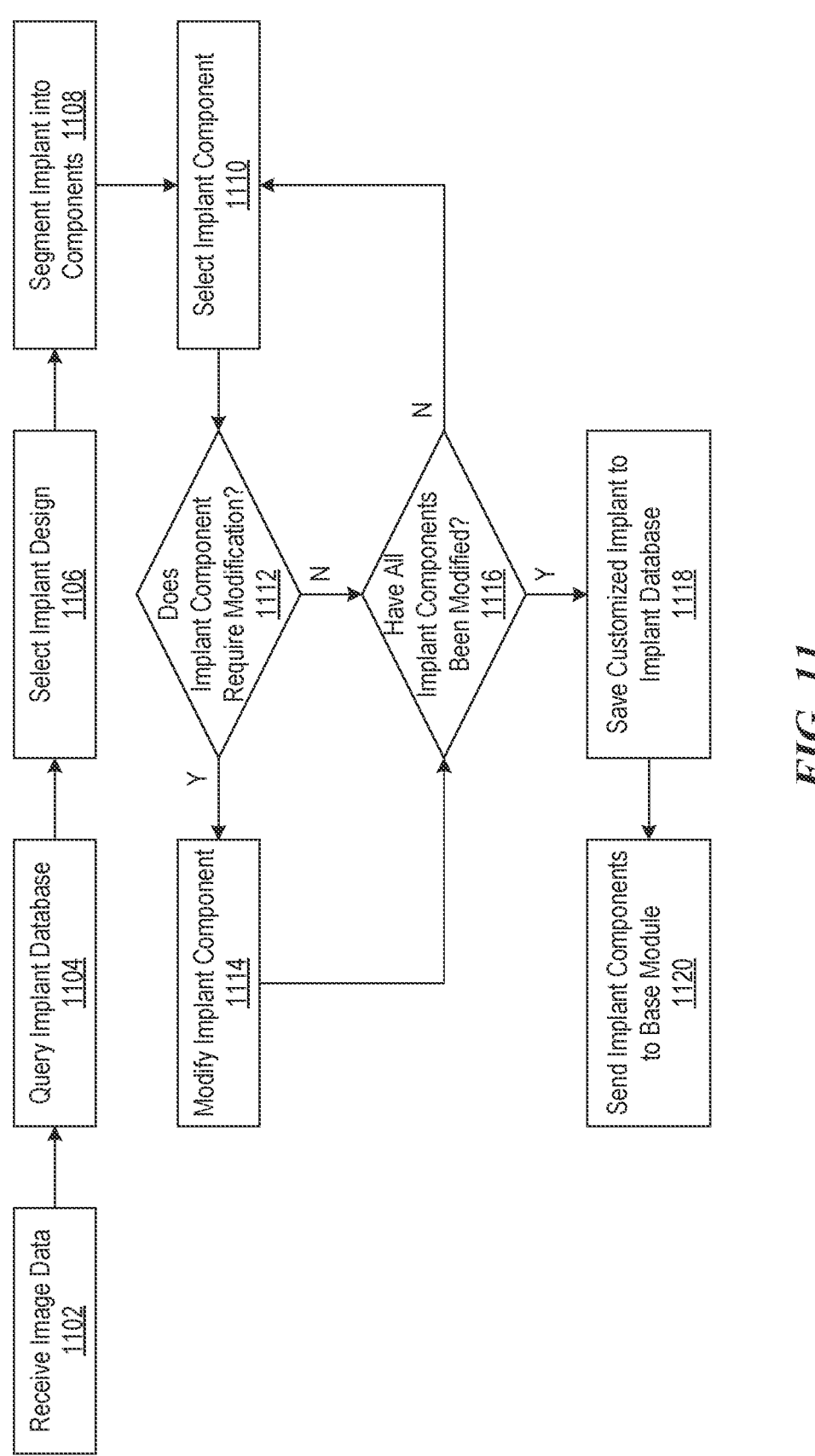
FIG. 11 is a flow diagram illustrating an example process for performing route planning for robotic surgical implant installation, in accordance with one or more embodiments.

FIG. 11 is a flow diagram illustrating an example process for performing route planning for robotic surgical implant installation, in accordance with one or more embodiments. An example operating room 102 is illustrated and described in more detail with reference to FIG. 1. In embodiments, the process of FIG. 11 is performed by the operating room system base module 632. The operating room system base module 632 is illustrated and described in more detail with reference to FIG. 6. In other embodiments, the process of FIG. 11 is performed by a computer system, e.g., the example computer system 300 illustrated and described in more detail with reference to FIG. 3. Particular entities, for example, the console 108 or the robotic surgical system 160, perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

FIG. 11 displays the implant module 634. In step 1102, the implant module 634 receives the image data from the base module 632. Alternatively, the implant module 634 receives a reference location or other identifying information to facilitate retrieval of the image data from the patient database 626. In embodiments, the image data can include a series of MRI images compiled into a 3D model of patient John Smith's pelvis, specifically the right-side socket of the ball joint where the femur meets the pelvis.

In step 1104, the implant module 634 queries the implant database 630 for implant 620 designs. The implant 620 designs can be specific to the type of implant 620 to be installed, such as a hip joint, or can be a category of implants 620 such as ball and socket joints. Similarly, the implant designs 620 can perform a specific structural task, such as reinforcing or fusing part of the spine. Additionally, the implant module 634 retrieves from the implant database 630 biocompatible materials that can be used in an implant 620 and their physical and chemical properties. The implant 620 may be a physical implant or a virtual implant.

In step 1106, the implant module 634 selects an implant 620 design from the designs retrieved from the implant database 630. Alternatively, an implant 620 can be completely customized to meet the physiology or needs of the patient. Such implants 620 may not be stored in the implant database 630 or may have been populated by a separate source, such as a third-party database or process accessible via the cloud, which may or may not have been saved to the implant database 630. In embodiments, the implant module 634 can select an artificial ball and socket joint that has been previously modified to fit the physiology of patient John Smith's right hip joint.

In step 1108, the implant module 634 segments the implant 620 into a plurality of implant components 622. The segmentation can be guided by data received from the simulation module 638 or the procedure module 640, which can include route parameters such that the maximum size of the implant components 622 does not exceed the smallest dimensions provided in the route parameters or other dimensions based on anatomical features. In some embodiments, the segmentation may be based upon one or more images of the patient's anatomy using image processing and edge detection techniques. In embodiments, the implant components 622 can be arbitrarily segmented, or can be segmented based upon previously delineated break points that may have been provided when the implant 620 was designed. The implant components 622 may not necessarily fit the strict definition provided by the route parameters. For example, if the minimum clearance provided by the route parameters is 1 cm×1 cm×5 cm, but an implant component 622 is 2 cm×2 cm×5 cm, the implant component 622 would require additional modifications.

In step 1110, the implant module 634 selects an implant component 622 from the plurality of implant components 622. In embodiments, the implant module 634 can select an implant component 622 that forms a quarter of the ring of the socket for the ball and socket joint intended to replace John Smith's right hip joint.

In step 1112, the implant module 634 determines whether the implant component 622 requires modification. The implant component 622 may require modification if the physical attributes of the implant component 622 exceed the route parameters received from the simulation module 638 or procedure module 640, or exceed the dimensions of spaces between anatomical structures identified using the image data. For example, an implant component 622 with dimensions of 2 cm×2 cm×5 cm would be too large to navigate the route based upon a minimum clearance of 1 cm×1 cm×5 cm. Such an implant would require modification to allow it to fit through such a space. Likewise, the space between a bone and a blood vessel may be 2 cm, requiring the implant component 622 to have a width no larger than 1 cm to allow for a clearance margin of 0.5 cm surrounding the implant component 622 while navigating through the patient's body.

In step 1114, the implant module 634 modifies the implant component 622 to achieve the necessary physical characteristics to allow compliance with the route parameters received from the simulation module 638 or the procedure module 640, or alternatively to comply with the identified dimensions of spaces between anatomical structures identified from image data. In embodiments, modifying an implant component includes replacing a solid portion of the implant component with a collapsible portion. For example, an implant component 622 with a solid volume of 2 cm×2 cm×5 cm can be changed to a collapsible structure such that in its collapsed form, the implant component 622 measures no more than 1 cm×1 cm×5 cm. Once at the implant site, however, the implant component 622 can be expanded to its original dimensions. In alternate embodiments, an implant component 622 can require modification to achieve desired physical characteristics, such as changing materials from a titanium alloy to a medical grade silicone to add more flexibility to an implant component 622. The modifications can facilitate navigation through the patient's body. In embodiments, the implant component 622 can be modified by further segmenting the implant component 622 into additional, smaller implant components 622.

In step 1116, the implant module 634 determines whether all of the implant components 622 have been modified or assessed for whether modifications are necessary. Similarly, the implant module 634 determines whether any implant components 622 remain unmodified. If more implant components 622 remain, the implant module 634 returns to step 1110 and selects an implant component 622.

In step 1118, the implant module 634 saves the customized implant 620 and implant components 622 to the implant database 630 when all of the implant components 622 have been modified or assessed for whether modifications are necessary. In step 1120, the implant module 634 sends the implant components 622 to the base module 632. The implant components 622 can include both modified and unmodified implant components 622. The implant components 622 can be modified to meet the patient's physiology, or to enable the implant component 622 to be compliant with the route parameters such that the implant components 622 can be navigated through the patient's body via the selected route.

Figure 12:
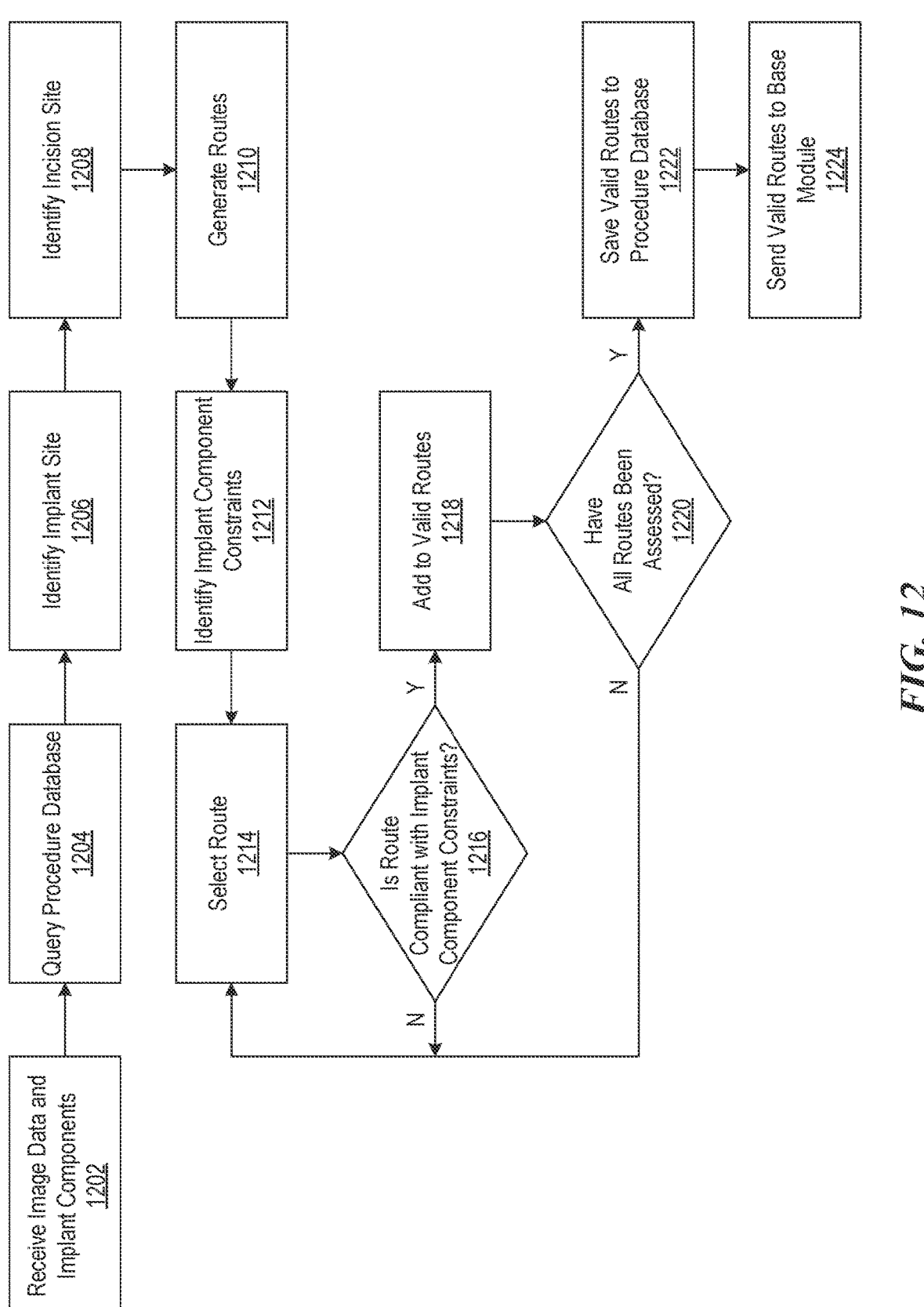
FIG. 12 is a flow diagram illustrating an example process for performing route planning for robotic surgical implant installation, in accordance with one or more embodiments.

FIG. 12 is a flow diagram illustrating an example process for performing route planning for robotic surgical implant installation, in accordance with one or more embodiments. An example operating room 102 is illustrated and described in more detail with reference to FIG. 1. In embodiments, the process of FIG. 12 is performed by the operating room system base module 624. The operating room system base module 624 is illustrated and described in more detail with reference to FIG. 6. In other embodiments, the process of FIG. 12 is performed by a computer system, e.g., the example computer system 300 illustrated and described in more detail with reference to FIG. 3. Particular entities, for example, the console 108 or the robotic surgical system 160, perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

FIG. 12 displays the route planning module 636. In step 1202, the route planning module 636 receives the image data and implant components 622 from the base module 632. Alternatively, the route planning module 636 receives a reference location or other identifying information to facilitate retrieval of the image data from the patient database 626 and the implant components 622 from the implant database 630. In embodiments, the image data can include a series of MRI images compiled into a 3D model of patient John Smith's pelvis, specifically the right-side socket of the ball joint where the femur meets the pelvis, and the implant components 622 can include 12 discrete implant components 622 that, when assembled, form an implant 620.

In step 1204, the route planning module 636 queries the procedure database 628 for procedures involved in the installation of an implant. The procedures can include at least an incision site and an implant site, and can further include a route from the incision site and the implant site through which tools and implant components 622 pass during the installation of an implant 620. In embodiments, the procedures can include hip replacement procedures where a hip joint is replaced by an implant.

In step 1206, the route planning module 636 identifies an implant site where an implant 620 will be installed in a patient. The implant site can be a bone, a joint, or other anatomical structure to be removed and replaced. Alternatively, the implant site can be a void space to be occupied by an installed implant 620. The implant site can additionally include the space immediately surrounding the location where an implant 620 is to be installed. The implant site includes both the location of the implant 620 once installed and the space surrounding the implant 620, which will be used to stage and assemble the implant components 622 as well as any other tools or equipment necessary to complete the procedure. In embodiments, the implant site is John Smith's right hip and the surrounding void spaces.

In embodiments, the system 600 (see FIG. 6) identifies an incision site and an implant site within an anatomy of a patient for implant installation based on one or more images of the anatomy. For example, in step 1208, the route planning module 636 identifies incision sites. An incision site is a location through which at least some tools, equipment, implant components 622, etc., will enter the patient's body. In an ideal embodiment, the incision site refers to the point at which an implant component 622 is to enter the patient's body. For example, the system 600 uses non-invasive digital image processing for automated detection of incision sites and implant sites before or during surgery. A combination of digital image segmentation, representation, and numerical description can be employed and validated on 2-D X-ray images of the anatomy. The ML model 216 (see FIG. 2) can be used for exploration of 3D image datasets of the anatomy, e.g., obtained from a Computed Tomography (CT) or Magnetic Resonance Imaging (MRI) scanner to identify an incision site and an implant site for surgical planning. Though the examples provided may refer to and utilize a single incision site, such reference should not be construed as a limitation, as multiple incision sites can be used. Similarly, implant components 622 can be inserted through any number of incision sites in any combination. In embodiments, the route planning module 636 can select an incision site at the side of the right lower abdomen.

In step 1210, the route planning module 636 generates at least one route between the one or more incision sites and the implant site. The routes are possible paths along which a tool or implant component 622 can be navigated through the patient's body. Multiple routes can exist from the same incision site to the implant site. The routes can direct tools and implant components 622 along different paths around anatomical structures.

In embodiments, the system 600 determines route constraints for the passage of an implant component 622 from an incision site to an implant site based on the size and shape of the implant component 622. For example, in step 1212, the route planning module 636 identifies constraints on the implant components 622 such as the physical dimensions of the implant components 622 and the margins required to safely install the implant components 622, which can include varying margins depending on the type of tissues in proximity to the implant components 622. For example, an implant component can be allowed to be within 0.1 cm of a bone, but no less than 0.5 cm from nerves or blood vessels. The constraints can additionally include deployment of collapsed implant components 622 and the space required for expansion and activation of expansion. The constraints can also include the flexibility of the implant components 622 including the location and amount of flex.

In step 1214, the route planning module 636 selects a route from the generated routes that has not been assessed for compliance with the implant component 622 constraints. In step 1216, the route planning module 636 determines whether the route is compliant with implant component 622 constraints. The route is compliant if it is able to accommodate the implant components 622 including their physical dimensions, flexibility or rigidity, and the location of anatomical structures. The compliance with the implant component 622 constraints is primarily determined by analysis of and comparison with the imaging data received from the base module 632. In an ideal embodiment, the imaging data is in the form of a three-dimensional model of the patient's anatomy. The route consists of a path through the model between an incision site and an implant site, and the route is compliant if the implant component 622 constraints can be accommodated based on the imaging data. If the route is not compliant, data can be saved to the procedure database 628 with details of the route, the non-compatible implant components 622, and the constraints that the route could not accommodate. In embodiments, the route must accommodate all implant components 622. In alternate embodiments, the route must accommodate at least one implant component 622.

In step 1218, the route planning module 636 adds the selected route to a list of valid routes if the route is compliant with the implant component 622 constraints. Valid routes can accommodate the implant component 622 constraints including maintenance of safe margins in proximity to sensitive tissues such as nerves, blood vessels, organs, etc. In embodiments, a valid route can be specific to an implant component 622. The route data can additionally include a list of implant components 622 with which it is compliant, if not required to accommodate all implant components 622 to be considered a valid route. The valid routes can additionally include a score, a rank, or other form of prioritization such that the higher-scoring or higher-ranking routes indicate an increased preference, representing a higher level of accommodation for the implant components. Such scores can be applied to all implant components 622 generally or can be determined separately for each implant component 622.

In step 1220, the route planning module 636 determines whether all routes have been assessed. If all routes have not been assessed for compliance with the implant component 622 constraints, the route planning module 636 returns to step 1214 and selects another route.

In step 1222, the route planning module 636 saves the list of valid routes to the procedure database 628. The valid routes can include at least one incision site, at least one implant site, and at least one path through the patient's body from the incision site to the implant site. In embodiments, the valid routes can additionally include a list of implant components 622 for which the routes are compliant.

In step 1224, the route planning module 636 sends the list of valid routes to the base module 632. In embodiments, one of the valid routes can form a path between an incision site at the side of the right lower abdomen and an implant site at the right hip, and a path between the incision site and the right hip following just beneath the skin. The route can additionally include a list of ten implant components 622 that it is capable of accommodating.

Figure 13:
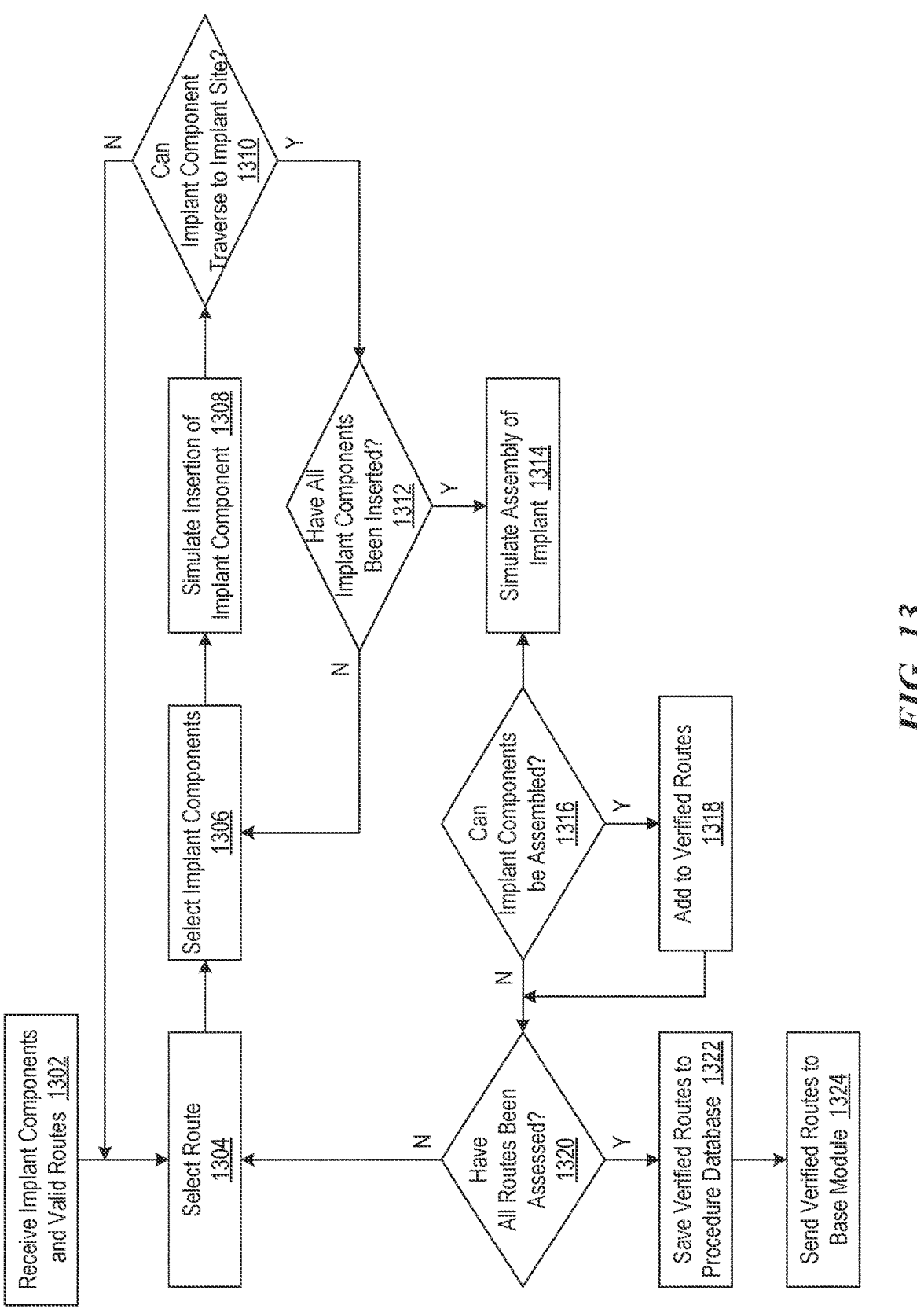
FIG. 13 is a flow diagram illustrating an example process for performing route planning for robotic surgical implant installation, in accordance with one or more embodiments.

FIG. 13 is a flow diagram illustrating an example process for performing route planning for robotic surgical implant installation, in accordance with one or more embodiments. An example operating room 102 is illustrated and described in more detail with reference to FIG. 1. In embodiments, the process of FIG. 13 is performed by the operating room system base module 632. The operating room system base module 632 is illustrated and described in more detail with reference to FIG. 6. In other embodiments, the process of FIG. 13 is performed by a computer system, e.g., the example computer system 300 illustrated and described in more detail with reference to FIG. 3. Particular entities, for example, the console 108 or the robotic surgical system 160, perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

FIG. 13 displays the simulation module 638. In step 1302, the simulation module 638 receives the implant components 622 and valid routes from the base module 632. The implant components 622 are segmented and modified such that they can be navigated along a selected route from an incision site to an implant site through the patient's body where the implant components 622 can be assembled into an implant 620. The valid routes can form a path from an incision site to an implant site through the patient's body able to accommodate at least one implant component 622.

In step 1304, the simulation module 638 selects a route from the valid routes for insertion of an implant component 622. In embodiments, a route is selected that is valid for all implant components 622. In alternate embodiments, an implant component 622 is selected prior to the selection of a route such that the route is selected which is valid for the selected implant component 622. The route can be selected based on a score, a rank, or other form of prioritization such that the most suitable route is selected. Alternatively, the route can be selected arbitrarily. In embodiments, all routes, whether valid or otherwise, can be selected in turn for simulation by the simulation module 638.

In step 1306, the simulation module 638 selects an implant component 622 from the plurality of implant components 622. In embodiments, an implant component 622 is selected that forms a quarter of the ring of the socket for the ball and socket joint intended to replace John Smith's right hip joint.

In step 1308, the simulation module 638 simulates the insertion of the implant component 622 by simulating the movement of the implant component 622 from the incision site through the patient to the implant site following the selected route. The simulation can include multiple evolutions, which can include different orientations of the implant components 622 as well as variations of other insertion parameters. For example, in a second evolution, the orientation of the implant component 622 can be rotated 90 degrees relative to the orientation of the implant component 622 during the first evolution.

In step 1310, the simulation module 638 determines whether the implant component 622 can safely traverse the selected route from the incision site to the implant site. The implant component 622 is found to be unable to traverse to the implant site if it is physically unable to navigate through the body via the selected route. In embodiments, the implant component 622 has no valid paths through the body regardless of orientation. In alternate embodiments, the implant component 622 can navigate through the body, however, encroaches on the required clearances of sensitive tissues. For example, an implant component 622 may pass within 0.3 cm of a nerve, while the required clearance is no less than 0.5 cm. If the implant component 622 can successfully traverse via the selected route, the simulation module 638 checks whether all implant components 622 have been inserted. If the implant component 622 cannot be inserted, the simulation module 638 can save data related to the attempt and failure to the procedure database 628 prior to returning to step 1304 and selecting an alternate route.

In step 1312, the simulation module 638 determines whether all implant components 622 have been inserted into the patient. If simulations have not been completed for all of the implant components 622, the simulation module 638 returns to step 1306 and selects another implant component 622.

In step 1314, the simulation module 638 simulates the assembly of the implant components 622 into the final implant 620 within the patient at the implant site. The assembly is spatially constrained by the space within the patient as determined by data from the procedure database 628 and images of the patient acquired from one or more imaging devices 618.

In step 1316, the simulation module 638 determines whether the implant components 622 can be successfully assembled into the final implant 620 within the patient. The implant components 622 cannot be assembled if, similar to simulating the movement of the implant components 622 to the implant site, the implant components 622 cannot be manipulated within the implant site sufficiently to assemble the implant 620. Likewise, the implant components must maintain safe clearances from sensitive tissues such as blood vessels and nerves, unless the implant 620 is supposed to be located in close proximity to such sensitive tissues, in which case an exception can be made.

In step 1318, the simulation module 638 adds the selected route to a list of verified routes if the route could be used to insert and navigate the implant components 622 to the implant site and successfully assemble the implant components 622 into an implant. In embodiments, a verified route can be specified for each implant component 622 instead of for all implant components 622. Verified routes allow for the implant components 622 and surgical tools to maintain safe margins in proximity to sensitive tissues such as nerves, blood vessels, organs, etc. The route data can additionally include a list of implant components 622 with which the verified route is compliant if not required to accommodate all implant components 622. The verified routes can additionally include a score, a rank, or other form of prioritization such that the higher-scoring or higher-ranking routes indicate an increased preference representing a higher level of accommodation for the implant components. Such scores can be applied to all implant components 622 generally or can be determined separately for each implant component 622.

In step 1320, the simulation module 638 determines whether all routes have been simulated. If all routes have not been simulated with each of the implant component 622 constraints, the simulation module 638 returns to step 1304 and selects another route.

In step 1322, the simulation module 638 saves the list of verified routes to the procedure database 628. The verified routes include at least one incision site, at least one implant site, and at least one path through the patient's body from the incision site to the implant site. In embodiments, the verified routes can additionally include a list of implant components 622 with which the routes are compliant.

In step 1324, the simulation module 638 sends the list of verified routes to the base module 632. In embodiments, one of the verified routes consists of a path between an incision site at the side of the right lower abdomen, an implant site at the right hip, and a path between the incision site and right hip following just beneath the skin. The route can additionally include a list of ten implant components that it is capable of accommodating.

Figure 14:
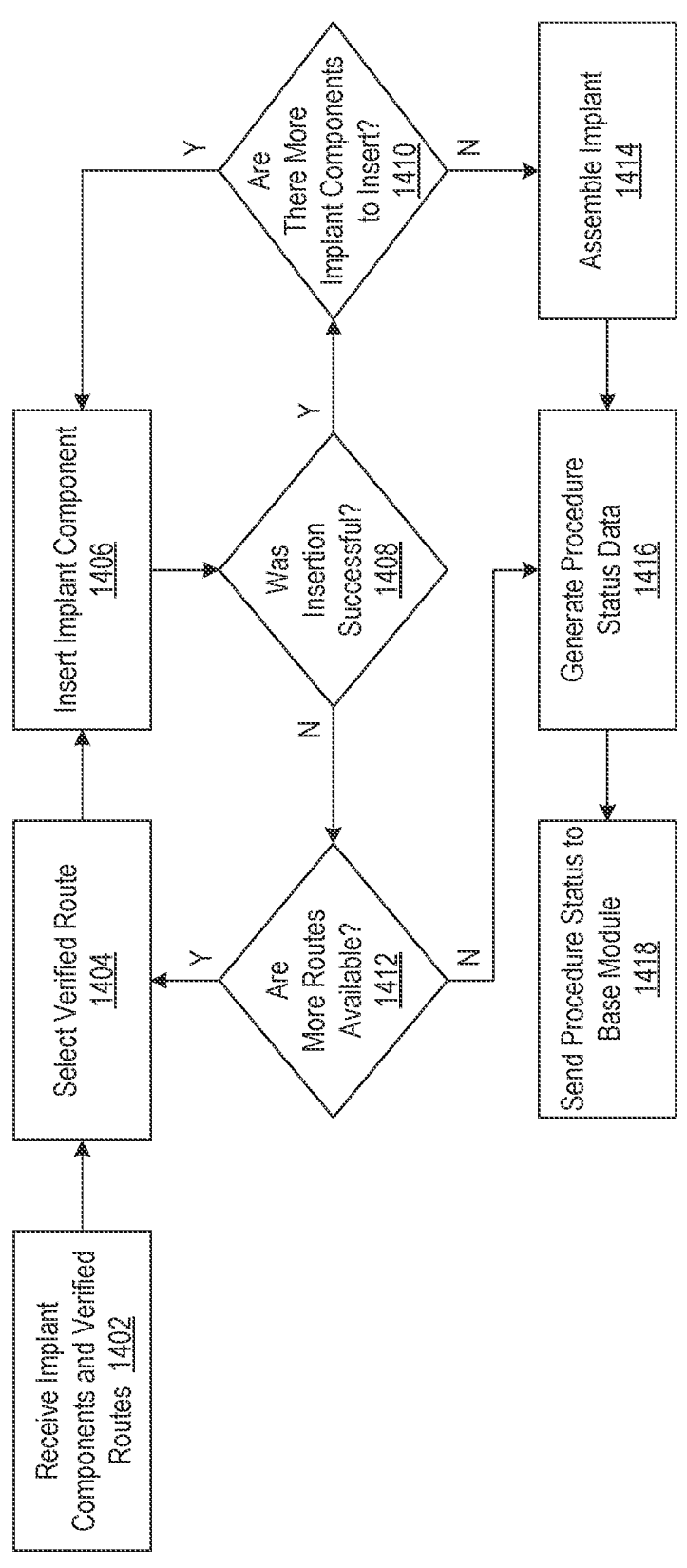
FIG. 14 is a flow diagram illustrating an example process for performing route planning for robotic surgical implant installation, in accordance with one or more embodiments.

FIG. 14 is a flow diagram illustrating an example process for performing route planning for robotic surgical implant installation, in accordance with one or more embodiments. An example operating room 102 is illustrated and described in more detail with reference to FIG. 1. In embodiments, the process 1400 of FIG. 14 is performed by the procedure module 640. The procedure module 640 is illustrated and described in more detail with reference to FIG. 6. In other embodiments, the process 1400 of FIG. 14 is performed by a computer system, e.g., the example computer system 300 illustrated and described in more detail with reference to FIG. 3. Particular entities, for example, the console 108 or the robotic surgical system 160, perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In step 1402, the procedure module 640 receives the implant components 622 and verified routes from the base module 632. The implant components 622 are segmented and modified such that they can be navigated along a selected route from an incision site to an implant site through the patient's body where the implant components 622 can be assembled into an implant 620. The verified routes consist of a path from an incision site to an implant site through the patient's body able to accommodate at least one implant component 622 that has been confirmed via simulations.

In step 1404, the procedure module 640 selects a route from the valid routes for insertion of an implant component 622. In embodiments, a route is selected that is valid for all implant components 622. In alternate embodiments, an implant component 622 is selected prior to the selection of a route such that the route is selected which has been verified for the selected implant component 622. The route can be selected based on a score, a rank, or other form of prioritization such that the most suitable route is selected. Alternatively, the route can be selected arbitrarily.

In step 1406, the procedure module 640 selects and inserts an implant component 622 from the plurality of implant components 622. In embodiments, an implant component 622 is selected that forms a quarter of the ring of the socket for the ball and socket joint intended to replace John Smith's right hip joint.

In step 1408, the procedure module 640 determines whether the implant component 622 was able to be safely maneuvered via the selected route from the incision site to the implant site. The implant component 622 is found to be unable to traverse to the implant site if it is physically unable to navigate through the body via the selected route. In embodiments, the implant component 622 has no valid paths through the body regardless of orientation. In alternate embodiments, the implant component 622 can navigate through the body but encroaches on the required clearances of sensitive tissues. For example, an implant component 622 may pass within 0.3 cm of a nerve, while the required clearance is no less than 0.5 cm. The assessment of whether the insertion of an implant component 622 was successful may be at the discretion of a surgeon, as the surgeon can use their clinical judgment to determine whether attempting to maneuver the implant component 622 may cause harm to the patient. If insertion was not successful, the procedure module 640 checks whether there are more routes available, otherwise it checks whether there are more implant components 622 to be inserted. In embodiments, minor modifications to the implant components 622 can be required. Such modifications may or may not constitute a failure of the implant component 622 depending upon whether the implant component 622 can be maneuvered to the implant site and additionally whether the implant component 622 can perform its original function upon arrival at the implant site.

In step 1410, the procedure module 640 determines whether there are more implant components 622 remaining to be inserted into the patient. If there are more implant components 622, the procedure module 640 proceeds to assemble the implant 620, otherwise, returns to step 1406 and selects and inserts the next implant component 622.

In step 1412, the procedure module 640 determines whether there are more routes available that can be used to insert the implant component 622. If another route is available, the procedure module 640 returns to step 1404 and selects another route. If no other routes are available, the procedure module 640 proceeds to step 1416 to generate procedure status data. The procedure status data indicates that the procedure is in progress and there are no remaining routes available. The procedure status can reference the specific implant component 622 that could not be successfully inserted and can additionally include data relevant to the failure, such as anatomical structures past which the implant component 622 could not be navigated. Such data can be automatically collected from at least one imaging device 618 or sensors 616, or can be provided manually by a surgeon or other medical staff.

In step 1414, the procedure module 640 assembles the implant components 622 into an implant 620 at the implant site. Should the assembly fail, the procedure module 640 generates procedure status data indicating the failure, which can be used to determine a method of assembly. In embodiments, minor modifications of the implant components 622 can be required during assembly.

In step 1416, the procedure module 640 generates procedure status data indicating the current status of the procedure. If the implant 620 is successfully assembled, a success message is generated indicating that the procedure has been successfully completed. If an implant component 622 could not be navigated to the implant site via a verified route and no routes remain to attempt, the procedure module 640 generates status data including at least the implant component, routes attempted, and any other data relevant to solving the pathfinding issue, such as the anatomical structures that prevented passage of the implant component 622, dimensions of the implant component that made it difficult to clear said anatomical structures, and any other sensitive tissues, structures, or concerns of the surgeon or other medical professionals preventing the successful insertion of the implant component 622 via one of the verified routes. Similarly, the generated procedure status data can indicate that the procedure is in progress and that a failure was encountered if the implant components 622 could not be successfully assembled, and can provide similar data indicating the components that could not be assembled and any data indicative of the issues preventing successful assembly.

In step 1418, the procedure module 640 sends the procedure status to the base module 632. The procedure status indicates that the implant components 622 have been successfully inserted and the implant 620 has been assembled and installed at the implant site. Alternatively, the procedure status can indicate that the procedure is still in progress. If the procedure is still in progress, the procedure module 640 additionally provides data indicating whether modification is required to the route of the implant components 622 or the assembly procedure for assembling the implant components 622. In embodiments, minor modifications to the implant components 622 can additionally be required.

Figure 15:
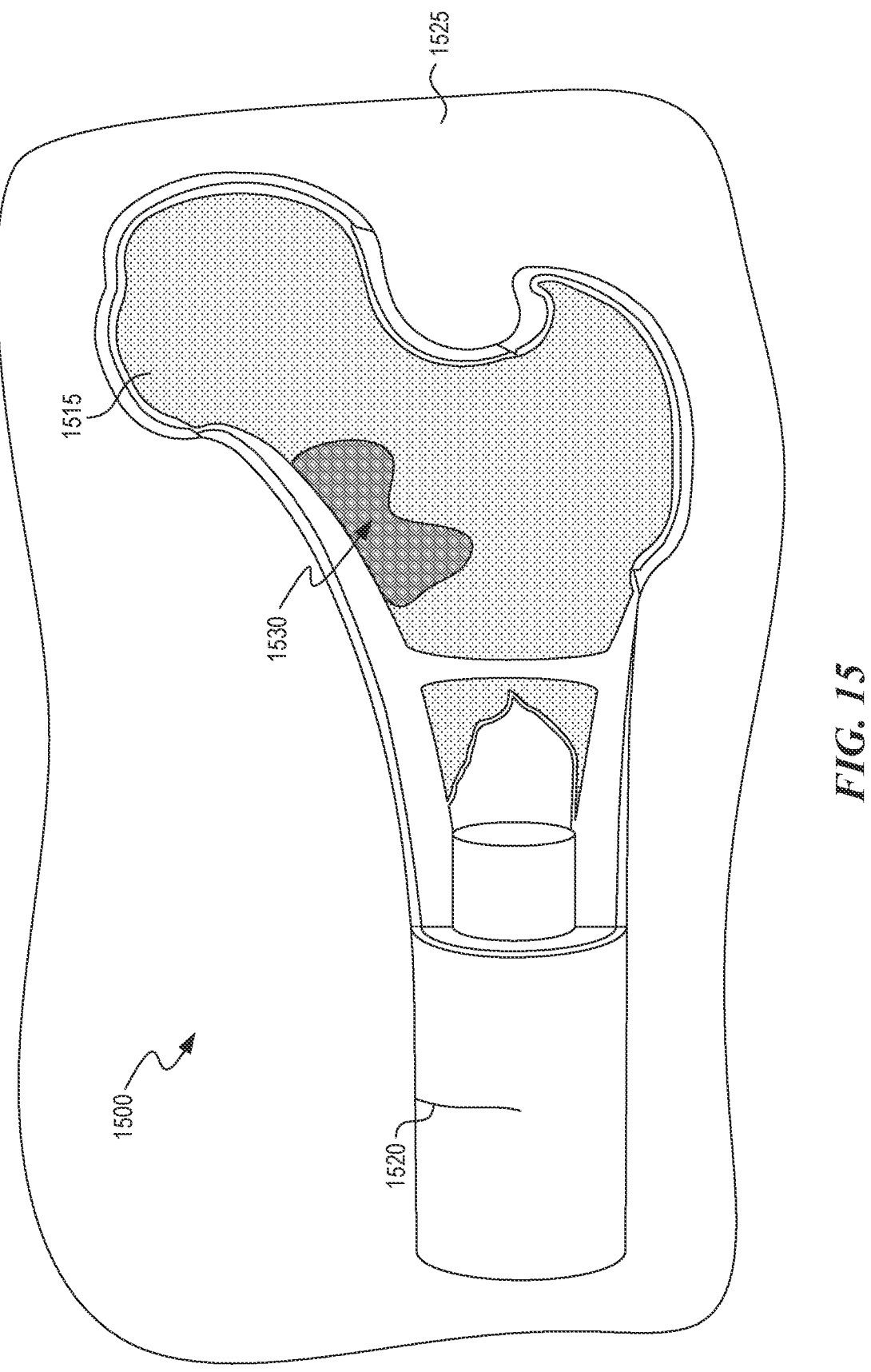
FIG. 15 illustrates an example image of a target region, in accordance with one or more embodiments.
Figure 16:
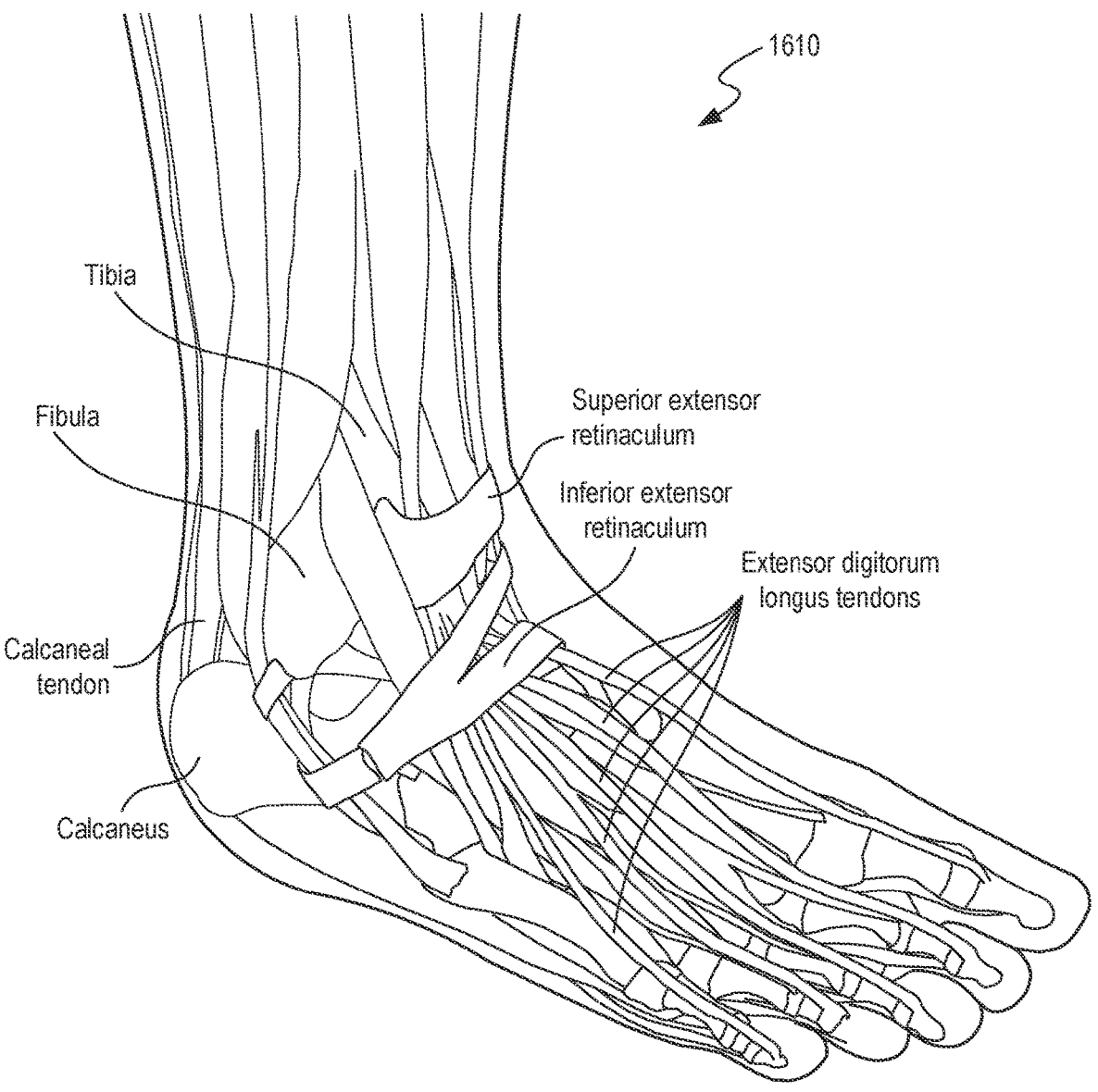
FIG. 16 illustrates an example image of another target region, in accordance with one or more embodiments.

FIG. 15 illustrates an example of an image 1500 of a target region, in accordance with embodiments. FIG. 16 illustrates an example of another image 1610, in accordance with one or more embodiments. The images 1500 and 1610 can allow a healthcare worker to view a target region 1525 to analyze an automated diagnosis, identify anatomical features and tissues of interest, etc. Systems disclosed herein can analyze a surgical plan to identify potential one or more anatomical features of interest. The system can select imaging modalities based on the potential one or more anatomical features of interest and available imaging modalities. The system can obtain at least one image for each imaging modality and generate a multi-modality image based on each of the obtained images. The system can determine one or more imaging characteristics for each potential anatomical feature of interest and correlate imaging characteristics to identify the available imaging modalities used to select the image modalities. The system can identify anatomical features in the image 1500 (e.g., a pre-operative image, real-time intra-operative image, etc.). The multi-modality images 1500 and 1610 can be generated based on a surgical plan, physician input, or other input data, and can indicate features (e.g., anatomical elements), margins, tissue type, etc.

Referring to FIG. 15, to generate the image 1500, systems disclosed herein can receive a tissue density image from an MRI device, a bone fracture image from a CT scanner, a bone degeneration or cancerous tissue image from an ultrasound machine, or images from other imagers disclosed herein. In embodiments, the image 1500 is generated for a surgical plan for treating a damaged bone and can include, for example, tissue density data 1515 (e.g., healthy tissue data from an MRI device), a bone fracture 1520 (e.g., identified using a CT scan), diseased tissue 1530 (e.g., low-density tissue, cancerous tissue, etc., from ultrasound images), or the like. The system can combine the data to generate the image 1500 with features and/or information of interest. In embodiments, the image 1500 highlights regions 1525 of a tissue sample according to the diagnoses and/or the values from a multi-modality device or multiple imaging devices. For example, the image 1500 can annotate, highlight, and/or otherwise identify/emphasize features of interest. The emphasis can help direct the doctor's review of the target region 1525 and/or further analysis of the patient. In embodiments, images are generated that include raw data and multi-modality images (e.g., composite images, a multi-layer overlaid image, etc.) to allow a physician to perform an independent diagnosis. In embodiments, the raw data is indicated via differences in shading, color, fill patterns, express indications, display tables, selectable displays, and/or in any other suitable manner.

The multi-modality images 1500, 1610 of FIGS. 15 and 16 can include selectable layers. For example, the multi-modality images can include a first layer created using a first modality, a second layer created using a second modality, and a third layer created using a third modality. A composite layer can include selected data from one or more of the three layers. The number of layers, number of imaging modalities, types of imaging modalities, data sets, fused data sets, and/or image processing (e.g., scaling of images, filtering of images, etc.) can be selected based on target characteristics of the composite layer and surgical plan (e.g., features of interest, anatomical elements, etc.). For example, the image 1500 of FIG. 15 can include selectable layers, each with one or more anatomical features identified (e.g., via annotation, false colors, etc.).

Figure 17:
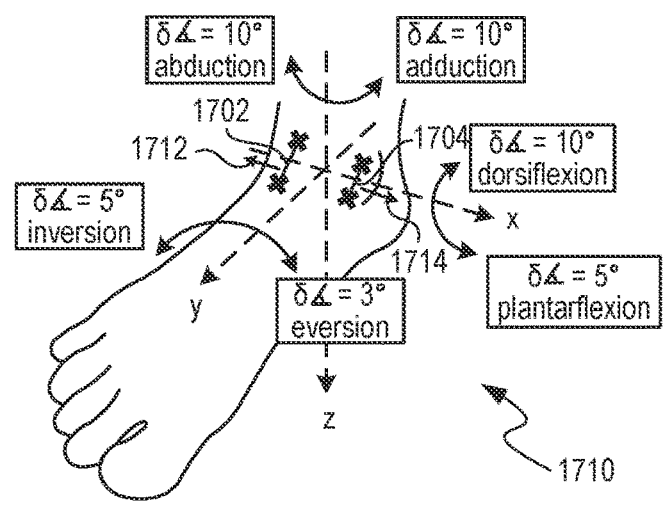
FIG. 17 shows movement of the human ankle, in accordance with one or more embodiments.
Figure 18A:
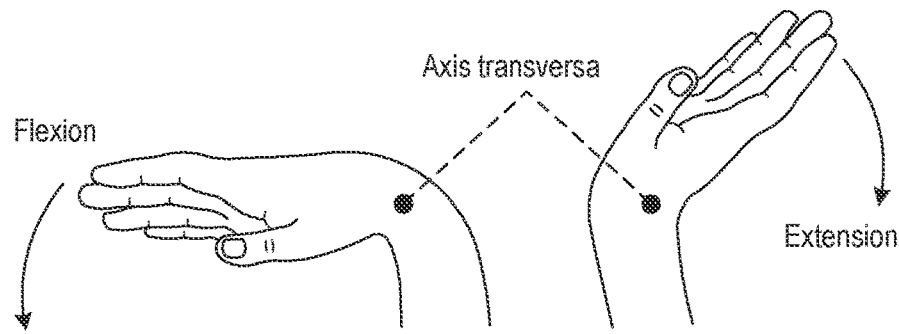
FIGS. 18A and 18B show movement of the human wrist, in accordance with one or more embodiments.
Figure 18B:
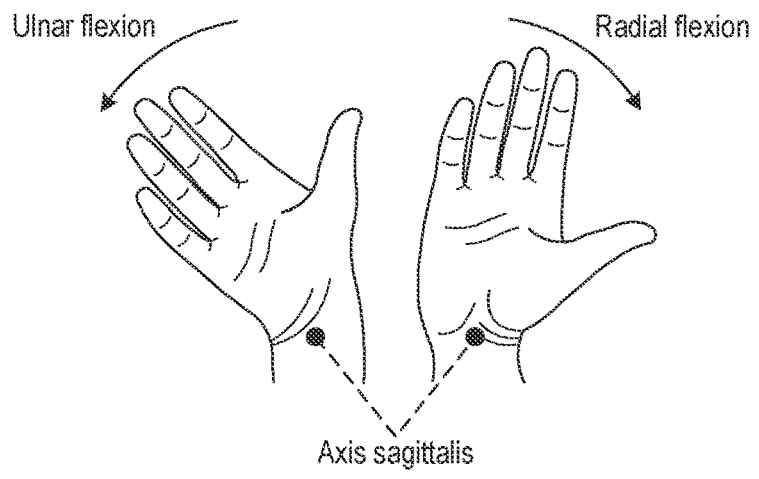

FIG. 17 shows movement of the human ankle, in accordance with one or more embodiments. FIGS. 18A and 18B show movement of the human wrist, in accordance with one or more embodiments. The systems disclosed herein can develop surgical plans to achieve the targeted motion and can simultaneously display pre-operative biomechanics and intraoperative biomechanics, pre-operative renderings of the surgical site and captured images of the surgical site, captured images of the surgical site and metrics, or combinations thereof. This allows a user to evaluate the accuracy of pre-operative predictions, progress of the surgical procedure, and/or real-time monitoring of metrics. The user is typically a medical professional, e.g., a surgeon, a nurse, a surgeon's assistant, or doctor. For example, a user can input one or more target outcome values, such as the number of degrees of freedom, range of motion, maximum/minimum motion/joint angles, or the like. The system can then perform any number of simulations using one or more virtual models to generate a surgical plan that meets the user inputted target outcome values.

Advantageously, surgical steps can be generated and provided to a surgical system to perform the procedure to meet the predicted outcomes based on soft tissue compliance, joint mechanics, loading, activities performed by patient, etc. The system can then update surgical plans to achieve the target outcome values and/or other user input. The number and position of anchor points, connections, and other features of the tethering can be selected to achieve the outcome criteria. For example, prior to conducting a surgery, the systems disclosed herein can simulate the mobility (e.g., sit, stand, walk, etc.) of the patient after the surgery.

FIG. 17 shows tethering 1702, 1704 (via anchors and sutures) that can stabilize the joint 1710. Virtual connections 1702, 1704 can be used in simulations to generate values or metrics for the ankle. For example, the values can include, for example, angles of abduction, dorsiflexion, plantarflexion, eversion, inversion, and/or other metrics, which can be displayed for evaluating predicted outcomes. The system can move tethering in a virtual model to perform additional simulations. For example, the tethering 1702, 1704 can be moved to another location, as illustrated by arrows 1712, 1714, respectively. The change in biomechanics based on a modification can be illustrated for viewing. For example, the change in the abduction, adduction dorsiflexion, plantarflexion, eversion, and/or inversion can be calculated and displayed.

By way of example, the pre-operative range of motion of the ankle can be, for example, dorsiflexion of 20°-30°, plantarflexion of 40°-50°, inversion/eversion of 30°, supination of 5°, or other ranges of motion. The change in tethering positions can result in an angle change of abduction of about 10° in either direction, angle of dorsiflexion of 10°, plantarflexion angle of 5°, eversion angle of 3°, and/or inversion angle of 5°. Bone-ligament tethering of ankle structures can be selected to achieve one or more of target outcome values. A user can move the location of the tethering to see the effects with joint movement in real-time.

Referring to FIGS. 18A and 18B, bone-ligament tethering, or other surgical steps, can be generated to modify the wrist to achieve one or more of target outcome values. A user can input target outcome values, such as a flexion of 80°-90°, extension of 75°-85°, radial flexion of 20°-22°, ulnar flexion of 35°, or other ranges of motion or values.

Virtual models and simulations disclosed herein can be performed to generate the surgical plans for the Figures herein. 3D images generated can be of the virtual model, simulated virtual steps of the procedure, and other images associated with the model/simulation. In some procedures, a CAD GUI receives images of the patient's anatomy and generates virtual two-dimensional or three-dimensional models with surface topologies, tissue properties, boundary conditions, etc. The models can represent anatomical features of interest, including skin, bones, soft tissue, fluids, connective tissue, and ligaments using the embodiments, methods, and features disclosed herein. The embodiments, methods, and features disclosed herein can be used to implement the examples discussed below.

In some virtually simulated leg procedures, an incision is made from a tip of the fibula to the extensor retinaculum of the virtual model. Virtual holes can be drilled in structures, such as the fibula, to place virtual drill guides, anchors, and other features along the anatomy. Multiple positions of fibula anchors can be analyzed to select a target fibula anchor position. One or more sutures can pass through the fibula anchor and be connected to another structure, such as ligaments (e.g., extensor retinaculum). The suture can then be routed back and returned to the anchor. In this manner, the fibula anchor can be used to limit motion of another structure. The system can analyze the characteristics and properties of the extensor retinaculum based on, for example, X-ray images, MRIs, and other patient images. Ankle simulations can be performed to, for example, select the number and locations of the anchors and sutures extending through, under, and/or above the extensor retinaculum.

Anchoring of the extensor retinaculum can cause tendons of the extensor muscles to be pulled inwardly toward the fibula. This can cause tensioning of the tendons of the peroneus tertius and the EDL. The alterations to the tendons can be virtually simulated based on the virtual tensioning of the sutures. This allows for virtual simulations of movement of a joint under loading, performing predefined determined tasks, etc. The tensioning of the extensor retinaculum can be increased or decreased to increase or decrease, respectively, the tensioning of the underlying tendons. Three-dimensional modeling analyses can be performed to accurately determine procedures to be performed based on the tensioning. In some procedures, additional or ancillary procedures can be performed to further adjust the procedure.

Additional anchors can be positioned along the leg. By way of example, a calcaneus anchor can be attached to the calcaneus bone. One or more sutures can be connected to the calcaneus anchor and connected to the extensor retinaculum (e.g., superior extensor retinaculum, inferior extensor retinaculum, etc.) one or more times in, for example, a weaving fashion, an overlapping fashion, or the like. The suture can then be attached to the fibula anchor, the calcaneus anchor, or another anchor. Tensioning of the extensor retinaculum can alter underlying tissue by, for example, tensioning one or more of the longus tendons. The number of anchors, number of times the suture passes through or is connected to the ligament, and other parameters can be selected based on the targeted outcome. Advantageously, overall motion of the joint can be analyzed based on multiple connections between multiple anatomical structures of the joint or structures surrounding the joint. The output from the simulations can be displayed for movements of the anatomy as illustrated in FIGS. 17-18B. A user can modify, adjust, and/or input values for the patient databases to perform additional simulations to generate predicted outcomes and confidence scores.

Inter-operative data can be compared to the predicted data in the patient databases. If differences between the predicted data and the actual data exceed a threshold, one or more warnings can be sent to the user or the robotic system. The surgical procedure can be adjusted to compensate for the changes. In some embodiments, the user can stop the procedure to perform alternative steps or evaluation based on the alert. The thresholds for alerts can be selected using ML models trained based on previous procedures. This allows alerts to be accurately generated.

The virtual robotic surgical procedures disclosed herein can be performed using simulation and CAD. For example, the virtual robotic surgical procedure is performed using the one or more processors to aid in the creation, modification, analysis, or optimization of implants and tools, and to create a database for manufacturing. Further, the virtual robotic surgical procedure can use vector-based graphics to depict the surgical implants, and can also produce raster graphics showing the overall appearance and path of the surgical implant in the virtual robotic surgical procedure. Moreover, the output of the virtual robotic surgical procedure can convey information, such as processes, dimensions, and tolerances, according to application-specific conventions. The virtual robotic surgical procedure can be used to design curves and figures in two-dimensional space or curves, surfaces, and solids in three-dimensional space, and to rotate and move a virtual model of the surgical implant for viewing. For example, virtual joints can be generated for 2D or 3D spaces.

Simulations for the virtual robotic surgical procedure can be performed using virtual models that can include two- or three-dimensional models to evaluate, for example, one or more steps of a surgical procedure (or entire procedure), predicted events, outcomes, etc. The simulations can be used to identify and assess biomechanics, access paths, stresses, strains, deformation characteristics (e.g., load deformation characteristics, load distributions, etc.), fracture characteristics (e.g., fracture toughness), fatigue life, etc. The virtual model can include a model of the patient's anatomy, implant(s), end effectors, instruments, access tools, or the like. The one or more processors can generate a three-dimensional mesh to analyze models. ML techniques can be used to create an optimized mesh based on a dataset of joints, anatomical features, and implants, or other devices. The three-dimensional models, surfaces, and virtual representations can be generated by CAD software, FEA software, and robotic control software/programs based on patient data (e.g., images, scans, etc.), implant design data, or the like. A user can view, manipulate (e.g., rotate, move, etc.), modify, set parameters (e.g., boundary conditions, properties, etc.), and interact with the models. The control parameters, robotic kinematics, and functionality can be used to generate the simulations. In some embodiments, models of end effectors of a robotic system are generated to perform virtual procedures on virtual anatomical models. Virtual simulations of surgical procedures in which a user selected robotic surgical steps and physician steps can be used to generate, modify, and select surgical plans, surgical robot configurations, or the like.

Pre-operative simulations can be performed for different surgical robots using pre-operative patient data (e.g., pre-operative scans, images, etc.). A surgical robot for performing a surgical procedure or portion thereof can be selected based on the simulation(s). This allows a healthcare provider to select a surgical robot suitable for a particular procedure. Additionally, the simulations can be used to generate, modify, and/or verify surgical plans. In some embodiments, a configuration of the surgical robot is selected based on the simulations. For example, multiple simulations can be performed for a surgical robot in different configurations (e.g., the surgical robot having different end effectors) and using different surgical techniques. The healthcare provider can select the surgical robot configuration and surgical plan based, at least in part, on the simulations. End effectors and tools of the surgical robot, imaging equipment, and manual equipment can be selected based on the simulations.

In some embodiments, the surgical system can perform virtual simulations based on one more design parameters, including simulation time, resource usage, accuracy level, and/or data output. The simulation time can be selected so that the virtual simulation is completed within a time period (e.g., percentage of completion time for a surgical step, percentage of surgical procedure duration, user input time period, etc.). The complexity of the models can be increased or decreased to decrease or increase, respectively, the simulation time period. If the user requests a significant amount of data output (e.g., joint mechanics, loads applied to anatomical structures, multiple implants, fatigue life, etc.), high complexity models (e.g., FEA models with a large number of elements/nodes, optimization models, fluid flow models, etc.) can be generated. Resource usage parameters can be used to select features of three-dimensional models of the anatomy and implants based on available processing resources, including central processing unit (CPU) cycles, memory space, network bandwidth, or a combination thereof. For example, the resource usage parameters can be set to limit usage of such processing resource(s). The surgical system can perform one or more corrective measures to free up the amount of resources required to enable process resources to be available to the robotic apparatus to complete tasks. The corrective measures can include one or more of allocating memory space, prioritizing packets, limiting CPU usage, and/or throttling bandwidth (e.g., throttling network bandwidth). The complexity and features (e.g., surface contours, feature matching, etc.) can be selected based on the available computing resources.

The surgical system can determine the simulation time period based on an action schedule of the surgical plan, a time allocated for the at least one robotic surgical action to be planned and completed, etc. The virtual simulations can be performed while one or more instruments are at least partially positioned within a patient to complete a current surgical action. This allows simulations to be performed concurrently with surgical actions on the patient. Suturing tools, anchoring tools, bronchoscopes, endoscopes, and/or imaging equipment are at least partially positioned within the patient to obtain the intraoperative patient data.

Virtual surgical procedures can include one or more robotic assisted surgical steps, automated surgical steps, and/or physician-controlled surgical steps. Intraoperative virtual simulations can be performed at any time during a surgical procedure to plan future surgical steps or actions. The system can collect real-time surgical data, patient data, or other information continuously or periodically before, after, and/or during surgical steps. Surgical plans can be modified based on intraoperative planning, trained ML models, virtual simulations, etc., and obtained data, such as pre-operative data, intraoperative data (e.g., surgical robot data, patient data, etc.), and/or other data. In some embodiments, virtual simulations are performed based on intraoperative patient data. The virtual simulations can be used to generate one or more robotic surgical actions for an intraoperative surgical plan using a trained ML model. The surgical system can control a robotic surgical apparatus to perform the robotic surgical action according to the intraoperative surgical plan. Planned robotic surgical actions can be generated any number of times to dynamically modify the intraoperative surgical plan. The real-time planning enables one or more trained ML models to determine surgical steps based on the current status of the patient, functionality of the surgical robotic apparatus, etc. If the surgical robotic apparatus is not configured for performing surgical action(s), a user can be notified that the configuration of the surgical robotic apparatus should be modified by, for example, changing end effectors, installing new instruments, etc.

Once reconfigured, the surgical robotic apparatus can continue in autonomous mode, semi-autonomous mode, or another mode.

In some embodiments, the processes described herein are performed by the modules described. In other embodiments, the processes are performed by a computer system, e.g., the example computer system 300 illustrated and described in more detail with reference to FIG. 3. Particular entities, for example, the console 108 or the robotic surgical system 160, perform some or all of the steps of the process in other embodiments. The console 108 and the robotic surgical system 160 are illustrated and described in more detail with reference to FIG. 1. Likewise, embodiments can include different and/or additional steps or can perform the steps in different orders.

Figure 19:
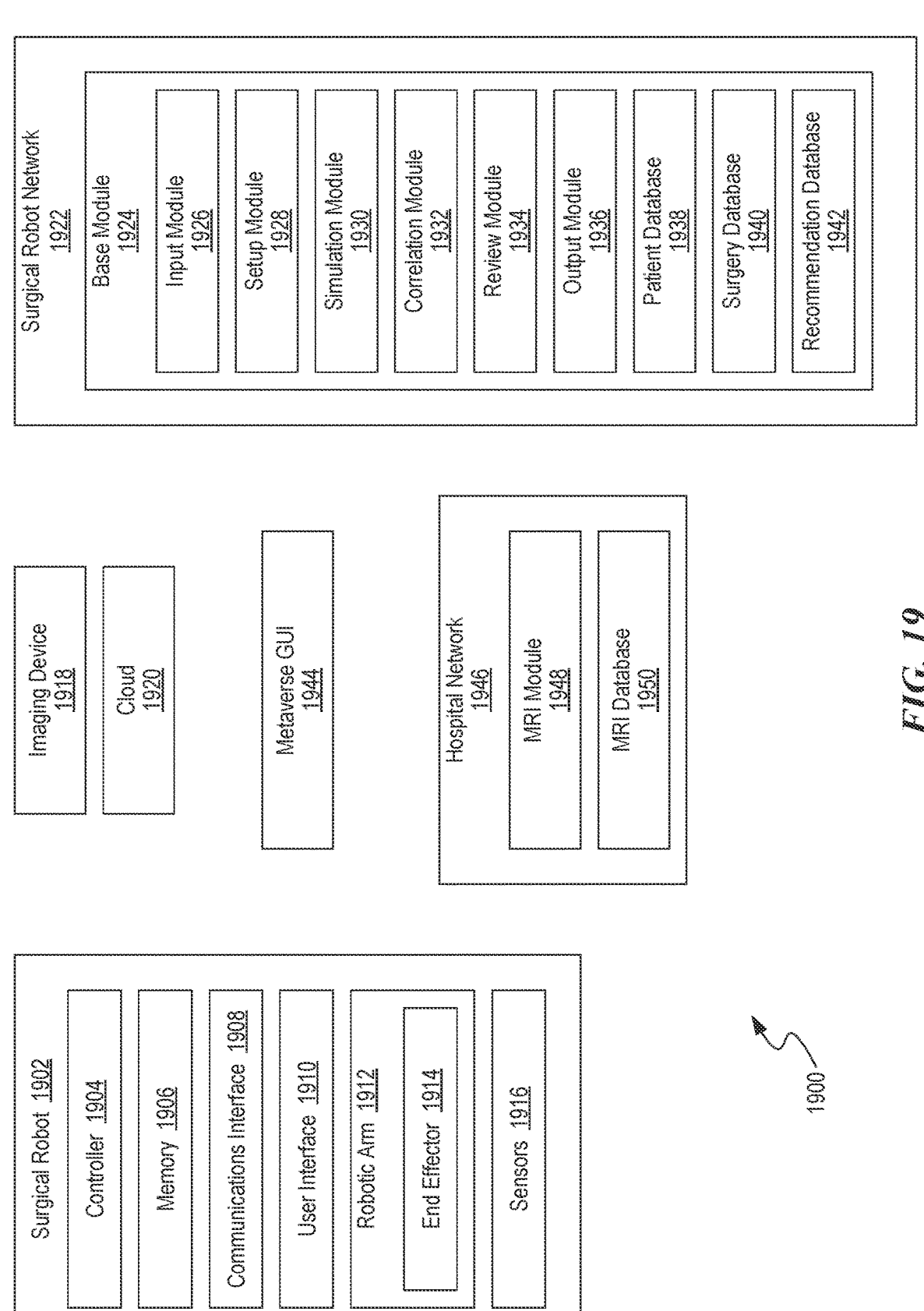
FIG. 19 illustrates a surgical metaverse system, according to an embodiment.

FIG. 19 illustrates a surgical metaverse system 1900, according to an embodiment. System 1900 includes a surgical robot 1902, which is a robotic system designed to assist a surgeon in performing a surgical operation on a patient. Surgical robot 1902 can include a controller 1904, memory 1906, and at least one robotic arm 1912 with an end effector 1914. The surgical robot 902 may further include a user interface 1910 for accepting control inputs from a user, such as a surgeon or other medical professional, and a communications interface 1908 for transmitting and receiving data to and from a cloud 1920 for the purpose of training an AI operating within the surgical robot or receiving remote commands from a remote user or an AI existing external to the surgical robot 1902.

The surgical robot 1902 may additionally comprise a plurality of sensors 1916 for providing feedback to the user or an AI. Controller 1904 is a computing device comprised of a processor for performing computations and communicates with a memory 1906 for storing data. The controller 1904 is in communication with a communications interface 1908 and may further be allowed to control the at least one robotic arm 1912 and end effector 1914 of a surgical robot 1902. The controller 1904 can be a commercially available CPU or graphical processing unit (GPU) or may be a proprietary, purpose-build design. More than one controller 1904 may operate in tandem and may be of different types, such as a CPU and a GPU. A GPU is not restricted to only processing graphics or image data and may be used for other computations.

Memory 1906 is the electronic circuitry within a computing device that temporarily stores data for usage by the controller 1904. The memory 1906 may additionally comprise persistent data storage for storing data used by the controller 1904. The memory 1906 may be integrated into a controller 1904 or may be a discrete component. The memory 1906 may be integrated into a circuit, such as soldered onto a component of a single board computer (SBC), or may be a removable component, such as a discrete dynamic random-access memory (DRAM) stick, secure digital (SD) card, flash drive, solid-state drive (SSD), magnetic hard disk drive, etc. In some embodiments, memory 906 may be part of a controller 904. Multiple types of memory 906 may be used by the surgical robot 902.

Communications interface 1908 allows the surgical robot 1902 to communicate with external devices and may comprise a wireless antenna and transceiver or a port for receiving a cable to facilitate a wired connection. Examples of a wired connection include ethernet, USB, or a proprietary connection. A wireless communications interface 1908 may include any of Wi-Fi, Bluetooth, NFC, or a cellular communications interface such as 3G, 4G, long-term evolution (LTE), or 5G. The communications interface 1908 may connect a user interface 1910 to the surgical robot 1902 or may facilitate access to a local network or a cloud 1920 network to access a remote server and/or database.

User interface 1910 is a means of interacting with a surgical robot 1902 and may include any of a keyboard, computer mouse, trackball, joystick, wireless or wired gamepad, sliders, scroll wheels, touch screen, or microphone for receiving voice commands. The user interface 1910 may additionally comprise any method of interaction of a user with a surgical robot 1902 not listed. The user interface 1910 may accept direct inputs, such as from a joystick controlling the movement of a robotic arm, or indirect inputs, such as commands entered on a keyboard or touch screen, such as adjusting the sensitivity of a joystick control or the speed of a robotic arm's movement in response to a joystick. The user interface 1910 may also comprise a screen for presenting information to the user, such as patient status, imaging data, and navigation data and speakers for providing auditory feedback. The user interface 1910 may also utilize haptics to provide feedback to the user. In additional embodiments, the user interface 1910 may comprise an augmented-reality (AR) or virtual-reality (VR) headset to enable a surgeon to view imagery from at least one imaging device 1918 in real-time and may additionally comprise an overlay, such as highlighting the blood vessels comprising a path which the catheter must be advanced to access the treatment site, such as a blood clot. The user interface 1910 may additionally comprise voice or eye-tracking controls. In embodiments, the controls are customized for the anatomy of the patient and the surgical procedure.

The robotic surgical embodiments herein use VR, AR, mixed reality (MR), or a combination thereof without limitation. Extended reality (XR) includes representative forms such as AR, MR, VR, and the areas interpolated among them. The levels of virtuality range from partially sensory inputs to immersive virtuality, also called VR. XR is a superset that includes the entire spectrum from "the complete real" to "the complete virtual" in the concept of reality—virtuality continuum. System 1900 can extend human experiences, especially relating to the senses of existence (represented by VR) and the acquisition of cognition (represented by AR). In embodiments, extended-reality learning (XRL) is used to generate a new immersive experiential learning model that places users into realistic intentional interactions. By leveraging AR, MR, VR, branching video (BV), and AI, system 1900 is able to go beyond simulation in a virtual metaverse. The user can control a virtual robotic surgical system, virtually perform surgical steps or manual surgical procedures, or the like while viewing avatars, interacting with virtual equipment, or the like.

Multisensory XR integrates the five traditional senses, including sight, hearing, smell, taste, and touch. Perception involves signals that go through the nervous system, as vision involves light striking the retina of the eye, smell is mediated by odor molecules, and hearing involves pressure waves. Sensory cues of multisensory XR include visual, auditory, olfactory, haptic, and environmental. Scent can be used in XR, as in biology, the olfactory system is integrated through the sensory nervous system. Multisensory experiences have elements of neuromorphic engineering, cognitive science, positive psychology, neuroenhancement, and nanoemulsion technology. In embodiments, system 900 uses OpenXR and WebXR standards. System 1900 can use perception, motor control, multisensory integration, vision systems, head-eye systems, and auditory processing.

System 1900 can simulate experiences that can be similar to or completely different from the real-world operating room. System 1900 can use either VR headsets or multi-projected environments to generate realistic images, sounds, and other sensations that simulate a user's physical presence in a virtual surgical simulation environment. In some embodiments, a surgeon performs manual surgical simulation that surgical robot 1902 later mimics. In some embodiments, a robotic surgical system performs virtual simulation in an XR surgical simulation environment.

A person using system 1900 is able to look around the artificial operating room, move around in it, and interact with virtual features or items. The effect can be generated by VR headsets consisting of a head-mounted display (HMD) having a small screen in front of the eyes but can also be created through specially designed rooms with multiple large screens. VR typically incorporates auditory and video feedback but may also allow other types of sensory and force feedback through haptic technology. The system 1900 uses either VR headsets or multi-projected surgical simulation environments to generate realistic images, sounds, and other sensations that simulate a user's physical presence in a virtual surgical simulation environment.

In embodiments, system 1900 uses AR. AR is an interactive experience of a real-world environment where the objects (e.g., surgical tools 154) that reside in the real operating room are enhanced by computer-generated perceptual information, sometimes across multiple sensory modalities, including visual, auditory, haptic, somatosensory, and olfactory. System 1900 can incorporate a combination of real and virtual operating rooms, real-time interaction, and accurate 3D registration of virtual and real objects. The overlaid sensory information can be constructive (i.e., additive to the natural environment) or destructive (i.e., masking of the natural environment). This experience is seamlessly interwoven with the physical operating room such that it is perceived as an immersive aspect of the real environment.

System 1900 blends components of the digital operating room into the users' perception of the real operating room, not as a simple display of data but through the integration of immersive sensations, which are perceived as natural parts of a surgical simulation environment. For example, system 1900 uses AR to enhance natural environments or situations and offer perceptually enriched experiences. With the help of advanced AR technologies (e.g., adding computer vision, incorporating AR cameras into smartphone applications, and object recognition), the information about the surrounding real operating room of the user becomes interactive and digitally manipulated. Information about the surgical simulation environment and its objects is overlaid on the real operating room. This information can be virtual. System 1900 can perform AR techniques in real-time and in semantic contexts with environmental elements. Immersive perceptual information is sometimes combined with supplemental information. This combines the benefits of both AR technology and heads-up display (HUD) technology. In embodiments, system 1900 uses MR, which is the merging of real and virtual operating rooms to produce new environments and visualizations, where physical and digital objects (e.g., patient anatomical features, surgical tools 154) co-exist and interact in real-time. MR is a hybrid of AR and VR.

System 1900 can receive user input from an interface, sensors of a headset (e.g., a VR headset), motion sensors, etc. System 1900 can control the movement of a virtual model of surgical robot 1902 according to the user input.

The degrees of freedom, accuracy, and operational parameters (e.g., speed of motion or range of motion) of the virtual model can match or be similar to the corresponding physical features of the robotic system. System 1900 can score one or more surgical steps performed in the XR surgical simulation environment. The scoring can be displayed in real-time or near real-time and used to determine the adjusted surgical workflow.

In some embodiments, system 1900 includes the system and components discussed in connection with FIGS. 4A-4C. To perform actions in the surgical metaverse, a user can operate hand-operated input devices (e.g., devices 424, 426, illustrated held by the user's left and right hands 427, 428, respectively in FIG. 4B). Referring to FIG. 4B, a viewer 430 can include left and right eye displays 434, 436 for metaverse viewing. Surgical team members can concurrently view the metaverse using viewers, VR headsets, etc. The user can view, for example, the surgical site, instruments 437, 438, or the like. The user's movements of the input devices 424, 426 can be translated in real-time to metaverse movements viewable via the viewer 430 and display (e.g., display 124 of FIG. 1) while the user can be provided with optional feedback, such as scoring of surgical steps, alerts (e.g., potential adverse events), notifications, and/or information. The information can include, without limitation, surgical or implantation plans, patient vitals, modification to surgical plans, values, scores, predictions, simulations, and other output, data, and information disclosed herein. The console 420 can be located in the surgical room or at a remote location. In some embodiments, the same console 420 is used to simulate surgical steps in the metaverse and to control the physical surgical robot.

The XR surgical simulation environment can include non-linear characteristics (e.g., micromechanics, mechanical behavior, etc.) of soft tissue and other mechanical properties applied to tissue to generate finite element models (e.g., non-linear finite element models), joint modeling (e.g., linear joint modeling, non-linear joint modeling, dynamic joint modeling, etc.), or the like. System 1900 can model and simulate the dynamic behavior of non-linear anatomical structures. The simulation can model the dynamic behavior of tissue interacting with instruments, implants, etc., and can include all or some pre-operative activities, intra-operative activities, and/or post-operative activities. This enables a user to select portions of a procedure to be analyzed.

Robotic arm 1912 is a mechanically actuated arm or lever with at least two degrees of freedom. Robotic arm 1912 will typically include at least one end effector 1914 or an imaging device 1918 and may include both an end effector 1914 and an imaging device 1918. In embodiments, system 900 obtains one or more images and sensor data for a patient using imaging device 1918 and sensors 1916. The robotic arm 1912 may additionally be capable of changing the end effector 1914 to facilitate multiple functions and operations of a variety of tools. The robotic arm 1912 may be manually controlled or operated in an autonomous or semi-autonomous mode. A surgical robot 1902 may have one robotic arm 1912 or multiple robotic arms 1912, each of which may be operated independently by one or more users or autonomous systems or a combination of users and autonomous systems.

An end effector 1914 is the end of a robotic arm 1912 which is conducting work. The end effector 1914 is typically a tool or device for interacting with a physical object and may be a surgical tool intended for acting upon or within a patient or may be a gripping device for securing a separate surgical tool to a robotic arm 1912. The end effector 1914 may be permanently affixed to the end of a robotic arm 1912 or may be detachable, allowing for a system of interchangeable end effectors 1914, which may alternatively be selected and swapped by a single robotic arm 1912 or multiple robotic arms 1912. The end effector 1914 may comprise a catheter or other tool for accessing a treatment site within a patient. Similarly, the end effector 1914 may relate to a deployable device, such as a stent, prior to deployment in a patient. The end effector 1914 may be constructed of materials that intentionally absorb, reflect, or are transparent to X-rays to facilitate the end effector's 1914 visibility when viewed using angiography, fluoroscopy, or other imaging modalities, or alternatively allow the X-rays to pass through to prevent their interference in images. In some embodiments, the end effector 1914 may be made to be selectively transparent to X-rays, such as by changing the profile of the end effector 1914 or X-ray absorbing or reflective components to increase or reduce their visibility to an imaging device 1918.

Sensor 1916 is a measurement tool for monitoring a characteristic or metric associated with a surgical robot 1902, end effector 1914, or patient. A sensor 1916 may be discrete or part of an array or assembly, such as integrated into a catheter. One or more of the sensors 1914 may include an electrophysiologic sensor, a temperature sensor, a thermal gradient sensor, a barometer, an altimeter, an accelerometer, a gyroscope, a humidity sensor, a magnetometer, an inclinometer, an oximeter, a colorimetric monitor, a sweat analyte sensor, a galvanic skin response sensor, an interfacial pressure sensor, a flow sensor, a stretch sensor, a microphone, any combination thereof, etc. The sensors 1916 may be integrated into the operation of the surgical robot 1902 or may monitor the status of a patient.

In embodiments, system 1900 extracts features from surgical actions performed by a user on a 3D digital twin. Generating a surgical workflow comprises generating workflow objects using a machine learning (ML) model based on the features. The ML model is trained to provide surgical workflows based on stored historical workflows. In embodiments, the ML model is trained using data obtained from the one or more sensors 1916. For example, data acquired by sensors 1916 is used to train a ML algorithm used by surgical robot 902 or AI to control surgical robot 1902.

Sensors 1916 may additionally comprise an X-ray dosimeter to monitor the intensity of X-rays being emitted toward the patient to prevent excessive doses of radiation. The sensors 1916 may be utilized to reduce the intensity of the X-rays or reduce the duration or increase the interval in which the X-rays are emitted toward the patient to control the dose throughout a procedure. An imaging device 1918 refers to any device capable of collecting data that can be used to create an image, or a representation of a physical structure or phenomenon. Imaging device 1918 is any device capable of detecting sound or electromagnetic waves and assembling a visual representation of the detected waves. Imaging devices 1918 can collect waves from any part of the electromagnetic spectrum or sounds at any range of frequencies, often as a matrix of independently acquired measurements, with each measurement representing a pixel of a two or three-dimensional image. These measurements may be taken simultaneously or in series via a scanning process or a combination of methods.

Some pixels of an image produced by an imaging device 1918 may be interpolated from direct measurements representing adjacent pixels in order to increase the resolution of a generated image. Imaging devices 1918 may receive or generate imaging data from a plurality of imagining devices 1918. The plurality of imaging devices 1918 may include, for example, cameras attached to the robotic arm 1912, cameras mounted to the ceiling or other structure above the surgical theater, cameras that may be mounted on a tripod or other independent mounting device, cameras that may be body worn by the surgeon or other surgical staff, cameras that may be incorporated into a wearable device, such as an AR device like Google Glass, Microsoft HoloLens, etc., cameras that may be integrated into an endoscopic, microscopic, laparoscopic, or any camera or other imaging device 918 (e.g., ultrasound) that may be present in the surgical theater.

Imaging device 1918 may include any algorithm or software module capable of determining qualitative or quantitative data from medical images, which may be, for example, a deep learning algorithm that has been trained on a data set of medical images. An imaging device 918 may further refer to a device used to acquire medical imagery by any means, including MRI, CT, X-ray, PET, ultrasound, arthrography, angiography, fluoroscopy, myelography, etc. An imaging device 1918 may acquire images in real-time or be used to create composite images or models in real-time.

Cloud 1920 is a distributed network of computers comprising servers and databases. Cloud 1920 may be a private cloud, where access is restricted by isolating the network, such as preventing external access, or by using encryption to limit access to only authorized users. Alternatively, a cloud 1920 may be a public cloud where access is widely available via the Internet. A public cloud may not be secured or may include limited security features.

In embodiments, system 1900 generates controls on a GUI for the user to perform actions on a 3D digital twin using an XR surgical simulation environment. In embodiments, the controls are customized for the anatomy of the patient and the surgical procedure. For example, surgical robot network 1922 is a network connected to surgical robot 1902 in which surgical robot 1902 receives and sends data, provides controls to a user for surgical robot 1902 through user interface 1910 and enables a user to use metaverse GUI 1944 to design, test, and create a surgical process for a patient. Base module 1924 initiates the input module 1926, the setup module 1928, the simulation module 1930, the correlation module 1932, the review module 1934, and the output module 1936 using a message, a software or hardware trigger, an interrupt, or another signal.

Input module 1926 begins by being initiated by the base module 1924. The input module 1926 connects to the MRI module 1948. The input module 1926 sends a request to the MRI module 1948 for the data stored in the MRI database 1950. Then, the input module 1926 is continuously polling to receive the data stored in the MRI database 1950. The input module 1926 receives the data stored in the MRI database 1950 from the MRI module 1948. Then the input module 1926 stores the received data in the patient database 1938. The input module 1926 returns to the base module 1924. Setup module 1928 begins operation by being initiated by the base module 1924. The setup module 1928 filters the patient database 1938 on the patient ID. The setup module 1928 extracts the patient's imaging data stored in the patient database 1938. The setup module 1928 creates the patient's 3D digital twin. The setup module 1928 stores the patient's digital twin in the surgery database 1940. Then the setup module 1928 displays the digital twin on the metaverse GUI 1944.

System 1900 generates a digital twin from patient images. The digital twin generated is a real-time virtual representation of the real-world operating room and surgical procedure (the physical twin) that serves as the indistinguishable digital counterpart of it for practical purposes, such as system simulation, integration, testing, monitoring, and maintenance. The operating room is outfitted with various sensors related to vital areas of functionality. These sensors produce data about different aspects of the patient and surgical performance, such as temperature, medical conditions, and more. The data from an operating room can be relayed to system 900 and applied to the digital copy.

In embodiments, the digital twin can include a digital twin prototype (DTP), a digital twin instance (DTI), or a digital twin aggregate (DTA). The DTP consists of the designs, analyses, and processes that realize the physical patient and procedures. The DTI is the digital twin of each individual instance of the patient's anatomy. The DTA is the aggregation of DTIs whose data and information can be used for virtual simulation of a surgical procedure, prognostics, and learning. In embodiments, Internet of Things (IoT) technology is used by system 1900 to enable connectivity between the physical operating room and its digital counterpart. The connectivity is generated by sensors on the physical patient or in the operating room that obtain data and integrate and communicate this data through various integration technologies.

In embodiments, system 1900 generates an XR surgical simulation environment by associating one or more virtual models of one or more surgical tools 154 and the surgical robot 1902 with one or more images of a patient and sensor data of the patient. The XR surgical simulation environment comprises a digital twin of the anatomy of the patient for performing a virtual simulation of a surgical procedure. In embodiments, system 1900 displays, via an electronic display, the 3D digital twin within the XR surgical simulation environment for viewing by a user. For example, a user can input setup options for metaverse GUI 1944 to generate the XR surgical simulation environment. The setup module 1928 returns to the base module 1924. A simulation module 1930 which begins by being initiated by the base module 1924. The simulation module 1930 filters the surgery database 1940 on the patient ID. The simulation module 1930 extracts the patient's digital twin. The simulation module 1930 displays the patient's digital twin on the metaverse GUI 1944. Then the simulation module 1930 displays the available tools for the surgery on the metaverse GUI 1944. Then the user selects a tool from the metaverse GUI 1944.

In embodiments, system 1900 identifies surgical actions performed by a user on a digital twin using an XR surgical simulation environment. For example, the user performs an action on the metaverse GUI 1944 using the selected tool. Simulation module 1930 determines if the user saved the tool and the action performed on the metaverse GUI 1944. If it is determined that the user did not save the tool and the action performed, the process returns to the user selecting a tool required for the surgery.

If it is determined that the user selected to save the tool and the action performed, the simulation module 1930 determines if another step is required in the surgery. If it is determined that another step is required for the surgery, then the user selects to add another step in the metaverse GUI 1944, and the process returns to the user selecting a tool required for the surgery. If it is determined that another step is not required for the surgery, the simulation module 1930 stores the tools and actions performed in the surgery database 940. Then the simulation module 1930 returns to the base module 1924.

Correlation module 1932 begins operation by being initiated by the base module 924. The correlation module 1932 filters the surgery database 1940 based on the surgery type.

For example, the correlation module 1932 filters the surgery database 1940 on the type of surgery that is needed by a patient, such as a Brostrom-Gould repair surgery. The Brostrom-Gould repair surgery is primarily used to repair the ATFL in the ankle. The recovery time for the procedure varies according to the patient but usually takes a minimum of 3-6 months. The surgery stabilizes the ankle, improves the ankle's mechanics, and restores function. The surgery helps a patient to experience less pain related to his or her injury and ankle sprains, as well as to avoid early arthrosis.

Correlation module 1932 selects the first parameter in the surgery database 1940. The correlation module 1932 performs correlations on the selected parameter and the remaining parameters to determine if the parameters are highly correlated. The correlation module 1932 determines if the correlation coefficient is over the predetermined threshold, for example, over a correlation coefficient of 0.75. If it is determined that the correlation coefficient is over the predetermined threshold, then the correlation module 1932 extracts the best match data point from the data set. The correlation module 1932 then stores the data entry for the best match data point in the recommendation database 1942. If it is determined that the correlation coefficient is not over the predetermined threshold, or after the data entry for the best match data point is stored in the recommendation database 1942, the correlation module 1932 determines if there are more parameters remaining in the surgery database 1940. If it is determined that there are more parameters remaining in the surgery database 1940, the correlation module 1932 selects the next parameter in the surgery database 1940, and the process returns to performing correlations on the parameters. If it is determined that there are no more parameters remaining in the surgery database 1940, the correlation module 1932 returns to the base module 1924.

Review module 1934 begins by being initiated by the base module 1924. The review module 1934 filters the surgery database 1940 based on the patient ID. The review module 1934 extracts the patient data from the surgery database 1940. The review module 1934 selects the first step in the patient's procedure from the extracted data from the surgery database 1940. The review module 1934 sorts the recommendation database 1942 by the highest correlated data entry. The review module 1934 selects the highest correlated data entry from the recommendation database 1942. The review module 1934 displays the patient data and the correlated data entry on the metaverse GUI 1944. The review module 1934 determines if the user selected the next data entry in the recommendation database 1942. In embodiments, system 1900 adjusts a surgical workflow based on a comparison of the surgical workflow to stored historical workflows. For example, if it is determined that the user did not select the next correlated data entry in the recommendation database 1942, the process continues to determine if the user made any adjustments to the step in the surgical workflow. In embodiments, system 1900 transmits the adjusted surgical workflow to surgical robot 1902 to configure the surgical robot 1902 with the adjusted surgical workflow. The adjusted surgical workflow comprises the workflow objects and information describing the surgical actions. Surgical robot 1902 is configured to perform surgical actions on the patient according to the adjusted surgical workflow.

If it is determined that the user selected the next data entry in the recommendation database 1942, the review module 1934 selects the next data entry in the recommendation database 1942, and the process returns to displaying the patient data and the correlated data entry on the metaverse GUI 1944. Then the review module 1934 determines if the user adjusted the step for the patient. If it is determined that the user did adjust the step for the patient, the review module 1934 stores the adjustment in the surgery database 1940. If it is determined that the user did not adjust the step for the patient or after the adjustment is stored in the surgery database 1940, the review module 1934 determines if there are more steps remaining for the procedure for the patient. If it is determined that there are more steps remaining for the patient's procedure, then the review module 1934 selects the next step for the patient's procedure, and the process continues to sort the recommendation database 1942 on the highest correlated data entry.

If it is determined that there are no more steps remaining for the patient's procedure, then the review module 1934 returns to the base module 1924. In embodiments, system 1900 configures surgical robot 1902 with an adjusted workflow comprising workflow objects and information describing surgical actions performed on a digital twin. For example, output module 1936 begins by being initiated by base module 1924. Output module 1936 connects to the surgical robot 1902. Then, the output module 1936 sends the data stored in the surgery database 1940 to the surgical robot 1902. The output module 1936 then returns to the base module 1924.

Patient database 1938 can include data describing a patient ID (e.g., JS123), a first name of a patient (e.g., John), or a last name of a patient (e.g., Smith). Patient database 938 can include data describing an area in which an MRI was taken (e.g., ankle) or data files (e.g., JS-Ankle #1.JPEG). Patient database 1938 can include data describing the MRI data of a patient. MRI is a medical imaging technique that uses a magnetic field and computer-generated radio waves to create detailed images of the organs and tissues in a body. Most MRI machines are large, tube-shaped magnets. When a patient lies inside an MRI machine, the magnetic field temporarily realigns water molecules in the body. Radio waves cause these aligned atoms to produce faint signals, which are used to create cross-sectional MRI images. In some embodiments, the MRI machine can also produce 3D images that can be viewed from different angles. In some embodiments, the database contains a series of cross-sectional MRI images and stores the data in the sequence in which they are captured by the imaging device. In some embodiments, the database may contain all of the historical medical images of a patient in order to create a virtual 3D representation of the patient's anatomy. In some embodiments, the database may contain all of the historical medical images of a patient in order to create a virtual 3D representation of the patient's anatomy.

In some embodiments, the patient's medical images used to create a 3D image or digital twin of the patient may be from a singular type of medical imaging, a plurality of different types of medical imaging, or any combination of types of medical imaging, including, MRI, CT, X-ray, PET, ultrasound, arthrography, angiography, fluoroscopy, myelography, etc.

Surgery database 1940 can include data describing a patient ID, a type of surgery, or a virtual 3D image of the patient. Surgery database 1940 can include data describing tools required for a surgery, a process required for a surgery, or data files for replays of a step as input into metaverse GUI 1944. Surgery database 1940 can include data describing (x, y, z) coordinates of a patient's body, tools used, or techniques used (e.g., a threading technique used in a surgery). The (x, y, z) coordinates of the anatomy specify the position of any anatomical structure in three-dimensional space using distances to three mutually perpendicular planes (or, equivalently, by a perpendicular projection onto three mutually perpendicular lines). In embodiments, n Cartesian coordinates (an element of real n-space) specify the structure in an n-dimensional Euclidean space for any dimension n.

Surgery database 1940 can include data describing calculations (e.g., forces required in certain steps or techniques), materials required for certain steps or techniques, or specialists required for specific steps or techniques. Surgery database 940 can include data describing patient data of historical patients that have had procedures performed.

Recommendation database 1942 contains the data entries that had highly correlated parameters that were over the predetermined threshold in the process described in the correlation module 1932. The recommendation database 1942 can include data describing a patient's ID, correlation coefficients, or a type of surgery. The recommendation database 1942 can include data describing a sex of a patient, an age of a patient, or a location of a patient. The recommendation database 1942 can include data describing a recovery time of a patient, a virtual 3D image of the patient, or tools required for a surgery. The recommendation database 1942 can include data describing a process required for a surgery, data files for replays of a step as input into metaverse GUI 1944, or (x, y, z) coordinates of a patient's body. The recommendation database 1942 can include data describing tools used, techniques used (e.g., a threading technique used in the surgery,) or calculations (e.g., forces required in certain steps or techniques). The recommendation database 1942 can include data describing materials required for certain steps or techniques or specialists required for the specific steps or techniques.

The recommendation database 1942 can include data describing a hospital in which a procedure takes place, a patient's primary care physician, or a surgeon or specialist performing a procedure. In embodiments, system 1900 extracts a success rate of a surgical procedure from stored historical workflows. A current surgical workflow is adjusted based on the success rate. For example, recommendation database 1942 includes data describing a success rate of a type of procedure, etc. In embodiments, data entries describe a patient's entire surgical procedure to be used during the review module 1934. In some embodiments, the data entries may store the individual steps of the patient's surgical procedure that are highly correlated with the current patient's planned surgical procedure.

Metaverse GUI 1944 is an XR-space in which users can interact with a computer-generated surgical simulation environment and other users. Metaverse GUI 1944 allows a user, such as a surgeon, doctor, medical professional, etc., to view an area of a patient's body that requires surgery in a VR space. The metaverse GUI 1944 allows the user to view a virtual 3D model of the operating room in order to input the movements necessary for the surgical robot 1902. The metaverse GUI 1944 also allows the user to select various tools, materials, and techniques that are required for the surgery and allows the user to manipulate the tools, materials, and techniques rendered over the patient's virtual 3D image to perform the processes and steps needed for the surgery in a virtual space. The user's movements and actions are saved and stored in the surgery database 1940 to assist the surgeon in performing the surgery or to provide the surgical robot 1902 with the approximate (x, y, z) coordinates to perform the surgery.

Metaverse GUI 1944 enables users to view or replay the surgery in the virtual 3D space to alter or adjust movements or actions to perform the surgery. The metaverse GUI 944 also allows other users to join in the same virtual 3D space to allow multiple users to collaborate on the surgical process for a patient, such as to select various tools, materials, and techniques that are required for the surgery and allows the user to manipulate the tools, materials, and techniques rendered over the patient's virtual 3D image to perform the processes and steps needed for the surgery in a virtual space. In some embodiments, the metaverse GUI 1944 may provide the user or surgical robot 1902 with a list of materials needed, a list of tools required, a workflow process of the surgical procedure, a virtual 3D visual replay of the surgical procedure, etc.

In embodiments, system 1900 generates a surgical workflow for the surgical robot 1902. The surgical workflow comprises workflow objects for the surgical procedure based on surgical actions performed on a digital twin. A workflow defines an orchestrated and repeatable pattern of activity (e.g., surgical steps) enabled by the systematic organization of medical resources into processes that transform materials, provide services, or process information. System 1900 defines a workflow as a sequence of operations, the work of surgical robot 1902, or one or more simple or complex mechanisms. A workflow can be a building block to be combined with other surgical steps or procedures. System 1900 establishes, performs, and monitors a defined sequence of processes and tasks in accordance with the workflow. A workflow can be represented as a graphical map. System 1900 also includes an extensible interface so that external software applications can be integrated and provide support for workflows that provide faster response times.

A workflow can be a description of a logically necessary, partially ordered set of actions to accomplish a specific goal (e.g., the surgical procedure) given certain starting conditions. A surgical plan, when augmented with a schedule and resource allocation calculations, defines a particular instance of systematic processing in pursuit of a goal (workflow). A workflow may be viewed as an often optimal or near-optimal realization of the mechanisms required to execute the surgical plan repeatedly.

A workflow object refers to an event, task, gateway, etc., associated with the workflow. Events define the start and the end of a surgical step that the workflow specifies. Each workflow has a Start event and an End event. Optionally, a workflow can include one or more Terminate events. A task (also referred to as a workflow action) runs a single unit of work in the workflow, such as a portion of a surgical step. An action represents something that is performed during the workflow. Examples of actions are provided throughout this specification in the context of arthroscopic surgery.

In some embodiments, the user may customize the virtual surgical simulation environment to match the operating room the surgeon will perform the surgery in, allowing the user to structure or design an operating room to determine the location of certain items for when the surgery is performed, or allow the user to create a unique operating room that is personalized by the user. In some embodiments, the patient's medical images used to create a 3D image or digital twin of the patient may be from a singular type of medical imaging, a plurality of different types of medical imaging, or any combination of types of medical imaging, including MRI, CT, X-ray, PET, ultrasound, arthrography, angiography, fluoroscopy, myelography, etc.

Hospital network 1946 provides medical information of a patient to the surgical robot network 1922, such as electronic health records, medical images, such as MRI, CT, X-ray, PET, ultrasound, arthrography, angiography, fluoroscopy, myelography, etc., lists patient doctors and health care professionals, provides patient's current medications and prescriptions, provides patient's medical history, and provides patient's specialists, etc. MRI module 1948 connects to the input module 1926. MRI module 1948 is continuously polling to receive a request for the data stored in the MRI database 1950 from the input module 1926. The MRI module 1948 receives a request for the data stored in the MRI database 950 from the input module 1926. Then, the MRI module 1948 sends the data stored in the MRI database 1950 to the input module 1926 and returns to continuously poll for a request from the input module 1926 for the data stored in the MRI database 1950. MRI database 1950 can store data describing a patient ID, a first name of a patient, a last name of a patient, an area in which an MRI was taken (e.g., ankle), or data files. MRI database 1950 can also store data describing the MRI data of a patient.

In some embodiments, the patient's medical images used to create a 3D image or digital twin of the patient may be from a singular type of medical imaging, a plurality of different types of medical imaging, or any combination of types of medical imaging, including MRI, CT, X-ray, PET, ultrasound, arthrography, angiography, fluoroscopy, myelography, etc.

In some embodiments, system 1900 generates an XR surgical simulation environment, including virtual models of one or more surgical tools 154, a virtual model of surgical robot 1902 configured to virtually operate the one or more surgical tools 154, and a 3D digital anatomical twin of a patient. System 1900 displays, via an electronic display, at least a portion of the 3D digital twin for viewing by a user controlling the virtual model of the surgical robot 1902 within the XR surgical simulation environment. System 1900 identifies surgical actions performed by the virtual model of the surgical robot 1902 using the virtual models of the surgical tools 154. System 1900 generates a surgical workflow for the surgical robot 1902. The surgical workflow comprises workflow objects for the surgical procedure based on the identified surgical actions. System 1900 adjusts the surgical workflow based on a comparison of the surgical workflow to one or more stored reference workflows. System 1900 transmits the adjusted surgical workflow to the surgical robot 1902 to perform the surgical procedure according to the adjusted surgical workflow.

In some embodiments, system 1900 compares the surgical workflow to the one or more stored reference workflows by scoring one or more steps of the surgical workflow. System 1900 compares the scored one or more steps of the surgical workflow with corresponding scores of reference steps in the reference workflows. System 1900 selects the reference steps with scores that are higher than the corresponding scored steps of the surgical workflow to modify the surgical workflow.

In some embodiments, the virtual model of the surgical robot 1902 is configured to simulate the functionality of the surgical robot 1902 to be used in the procedure. In some embodiments, system 1900 receives user input from the user. System 1900 controls the movement of the virtual model of the surgical robot 1902 based on the user input. System 1900 scores the surgical steps performed in the XR surgical simulation environment, wherein the scoring is used to determine the adjusted surgical workflow. System 1900 generates 3D movements of the surgical tools within the XR surgical simulation environment to simulate surgical steps performed by the one or more surgical tools 154.

Figure 20:
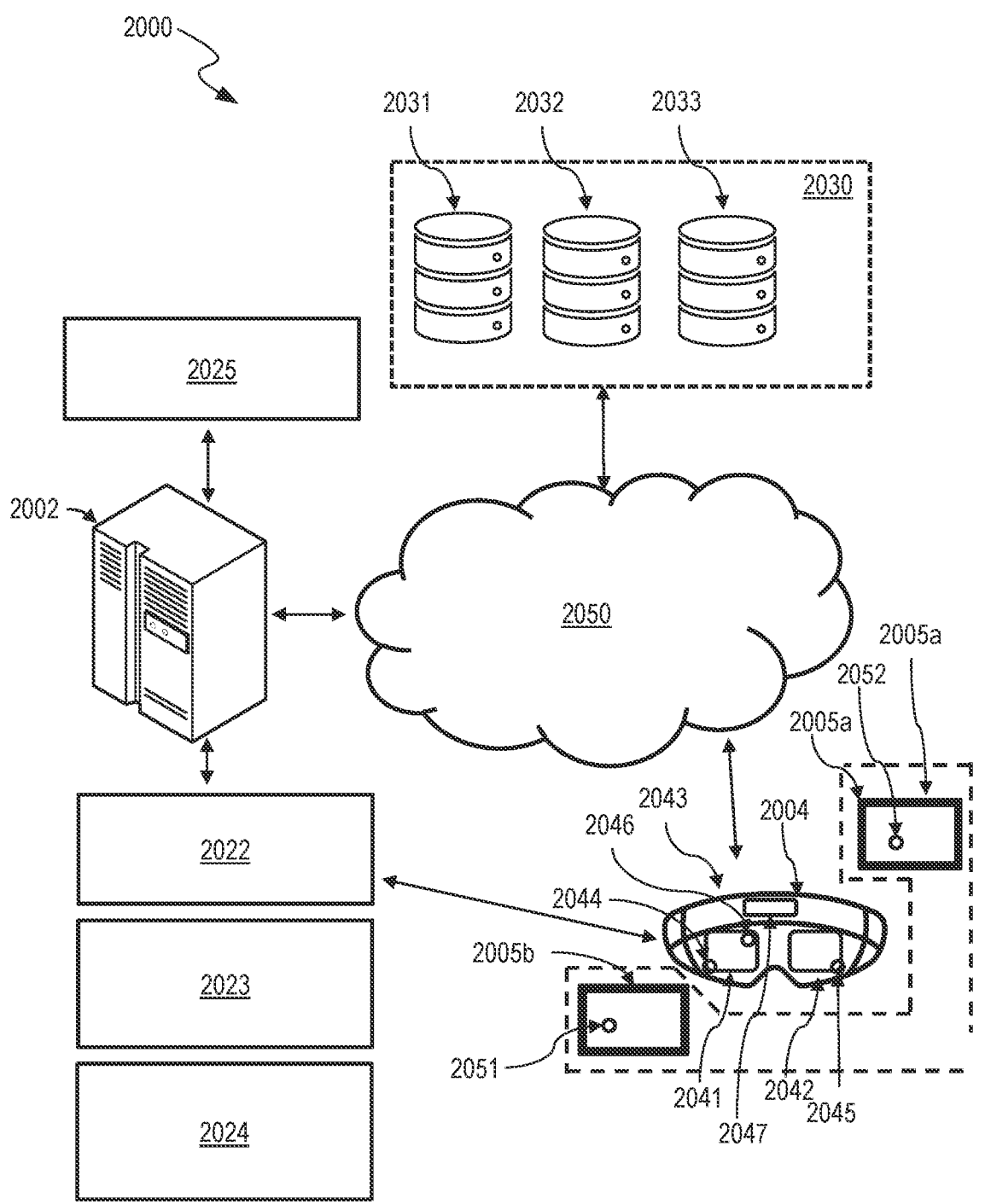
FIG. 20 illustrates an extended reality (XR) system for facilitating robotic medicine, in accordance with one or more embodiments.

FIG. 20 illustrates an XR system 2000, in accordance with one or more embodiments. System 2000 can be used to perform an XR computer-implemented method. For example, system 2000 can be used for pre-operative training, surgical planning, intra-operative assistance or monitoring, etc. For pre-operative training, system 2000 can be used to simulate surgical steps, train ML systems, and analyze or map anatomy (e.g., patient anatomy obtained via images, digital twin, etc.). An example ML system 200 is illustrated and described in more detail with reference to FIG. 2.

System 2000 can analyze user performance and then generate additional simulations based on the user performance to allow users to practice surgical procedures any number of times. For surgical planning, a user (e.g., a physician, surgeon, or other medical professional) or system 2000 can remove, add, or modify actions based on, for example, user performance, user input, predicted events, outcomes, or the like. For intra-operative assistance or monitoring, system 2000 can generate an XR environment (e.g., an AR environment or other environment) with displayed anatomical information (e.g., mappings of anatomical features), surgical plan mapping, instrument data (e.g., instrument instructions, operational parameters, etc.), sensor data, patient data (e.g., real-time vitals or patient records), and other information for assisting the user.

Mappings of anatomical features can include, without limitation, labeling that identifies anatomic elements (e.g., organs or tissues), positions of anatomical features (including underlying anatomical features not visible to the naked eye), target information (e.g., targeted tissue to be removed or target location for implanting devices), or the like. System 2000 can display, for example, mapping information in the multi-modality images 1500, 1610 of FIGS. 15, 16, respectively. For example, the anatomical features (e.g., tibia, fibula, etc.) of the joint in image 1610 can be labeled as shown in FIG. 16. The diseased tissue 1530 of FIG. 15 can be labeled and identified to assist with its removal. As the tissue 1530 is removed, the image can be updated to show margins to limit the removal of healthy tissue. The user can select layers of mappings (e.g., cardiovascular layers showing cardiovascular features, neurological layers showing nerve tissue, orthopedic layers identifying anatomy of joints, target layers showing targeted tissue(s) or implant sites, surgical step layers showing a post-surgical step outcome, simulation layers shown simulation outcomes, etc.) to control the displayed information.

In some embodiments, system 2000 obtains a digital anatomical model representing the anatomical features of a patient. The digital anatomical model is generated using the imaging methods described in more detail with reference to FIG. 1 and the methods described in more detail with reference to FIG. 19. System 2000 can include an AR device (e.g., wearable device 2004) that provides VR simulations for practicing surgical procedures and identifying anatomical features (e.g., tissue, organs, abnormal features, normal features, or non-targeted tissue).

In some embodiments, system 2000 generates an XR surgical simulation environment that includes the digital anatomical model. The digital anatomical model is viewable by at least one user using an AR device, such as the devices illustrated and described in more detail with reference to FIGS. 20-21. The XR surgical simulation environment is configured to enable the at least one user to virtually perform one or more surgical steps on the digital anatomical model. For example, the user can identify types of tissue (e.g., bony tissue, cartilage, skin, fat, nerve tissue), abnormal features (e.g., diseased tissue, malfunctioning organs, or normal features such as healthy tissue or organs), non-targeted tissue (e.g., nerves or healthy tissue) when viewing a digital twin or a virtual anatomical model of the patient.

A different XR platform is used, and a different XR surgical simulation environment is generated for different surgery types, e.g., cardiovascular, neurological, or orthopedic surgery. A different XR platform is used for each of the above because each platform has different modeling parameters. The modeling parameters can be retrieved from a modeling parameter library for generating a digital anatomical model based on one or more surgical steps of a surgical plan. For example, cardiovascular parameters used to generate a digital anatomical model include heart valve properties, tissue properties (e.g., elastic properties of vascular wall tissue), fluid pressures (e.g., aortic blood pressure), heart rate, dP/dt max, cardiac output, stroke volume, pulmonary artery blood pressure, pulmonary capillary wedge pressure, peripheral resistance, tension time index, left cardiac work, or renal blood flow and resistance. Neurological parameters can include parameters related to nerve tissue (e.g., signal transmission characteristics, size of nerves, etc.), mental status, cranial nerves, motor system, reflexes, sensory system, coordination, or station and gait.

Different ML models are used and trained differently for each XR surgical simulation environment generated for different surgery types. For example, ML models for orthopedic surgery are trained using training data describing joint and muscle forces, muscle and joint loads, activation patterns, muscle-tendon behavior, muscle excitations, or muscle fiber lengths. Different XR platforms are used because the error margins between anatomical features are different for different surgery types. For example, brain surgery offers less room for error than orthopedic surgery. The granularity of anatomical features is different. Therefore, different VR modeling is performed for each surgery type, and different software packages are designed.

VR training can also include identifying features (e.g., anatomical structures or delivery paths), surgical equipment, body part positions (e.g., a body part position of the patient, a body part position of the user or surgical team member positions), and other data to assist in surgical procedures. User input (e.g., labels, position notes, or the like) can be collected (e.g., voice, keyboard, XR device input, etc.) during the simulations and then used to modify planned surgical procedures, provide annotation during surgical procedures using XR environments, or the like.

In some embodiments, system 2000 receives anatomical mapping information from the at least one user via the XR device (e.g., VR device, AR device, etc.). In some embodiments, the same XR device is used to perform VR simulations to input anatomical mapping information and perform an AR-assisted surgery on the patient based on the anatomical mapping information. In other embodiments, different XR devices are used for training and performing the surgery. In some training procedures, multiple users input anatomical mapping information, which is aggregated to determine what information is correct. The aggregation can be used to determine confidence scoring for XR mapping. For example, a confidence score for AR mapping is based on a threshold percentage (e.g., at least 80%, 90%, 95%, or 99%) of the users providing the same mapping (e.g., mapping input using an XR environment).

In response to the confidence score reaching a threshold level for anatomical features associated with a procedure, the mapping can be deployed for performing the procedure on patients. Example anatomical mapping information is described in more detail with reference to FIG. 22. In AR/VR-assisted surgical procedures, the wearable device

2004 can display information to assist the user. The displayed information can include surgical plan information (e.g., instrument information, current surgical staff, progress in the surgical procedure, or potential adverse events), patient vitals, anatomical mappings, physician notes, and other information to assist the user. The user can move, add, or eliminate displayed information to enhance the experience. The configuration of the wearable device 2004, information displayed, and feedback provided to the user can be selected based on the procedures to be performed.

In some embodiments, system 2000 performs confidence-score AR mapping to meet a confidence threshold for the one or more surgical steps to be performed on the anatomy of the patient. Confidence-score AR mapping is described in more detail with reference to FIG. 22. The confidence-score AR mapping includes selecting at least a portion of the anatomical mapping information for the AR mapping to the anatomy of the patient. The selected anatomical mapping information is mapped to the anatomical features of the patient. Via the AR device, an AR environment is displayed to the at least one user. The AR environment includes the mapping of the selected anatomical mapping information to the anatomical features.

In some embodiments, the confidence threshold (e.g., 90%, 95%, or 99%) is selected based on a surgery type of the one or more surgical steps. Image data of the patient is segmented to identify digital anatomical features associated with the surgery type. For example, the identification is performed using the ML system 200 of FIG. 2. The digital anatomical features are part of the digital anatomical model. Via a VR device, one or more anatomical identification prompts are generated for receiving the anatomical mapping information from the at least one user to label one or more discrete anatomical features viewed by the user. The surgery type can be a cardiovascular surgery, an orthopedic surgery, brain surgery, a joint replacement surgery, or an anatomical features repair surgery. The discrete anatomical features associated with the surgery type can be identified using one or more ML algorithms.

The AR environment includes the mapping of the selected anatomical mapping information to the anatomical features. In some embodiments, the computer system maps at least some of the anatomical features of the patient using a ML platform. The ML platform includes a plurality of surgery-type-specific ML modules to be applied to the image data of the patient to provide the anatomical surgery-type mapping. The surgery-type-specific ML modules can be trained using surgery-type grouped data sets, including surgery-type mappings. Surgery-type mappings can include layers based on the surgery type. For example, a cardiovascular surgery mapping can include layers showing cardiovascular features (e.g., vessels, arteries, etc.), targeted features (e.g., heart valves to be modified or replaced, locations of atherosclerosis, etc.). A neurological surgery mapping can include layers showing nerve tissue (e.g., a layer with target nerve tissue, a layer with non-targeted nerve tissue). An orthopedic surgery mapping can include layers identifying the anatomy of joints. The user can select layers, data sets, and mapping information to be added or removed from the surgery-type data. For example, each platform includes a different feature extraction module, a different ML model, and different training methods.

System 2000 includes a server (or other computer system 2002), where such system 2002 includes one or more non-transitory storage media storing program instructions to perform one or more operations of a projection module 2022, a display module 2023, or a feedback module 2024. In some embodiments, system 2000 includes wearable device 2004, where the wearable device 2004 may include one or more non-transitory storage media storing program instructions to perform one or more operations of the projection module 2022, the display module 2023, or the feedback module 2024.

Wearable device 2004 can be a VR headset, such as a head-mounted device that provides VR for the wearer. Wearable device 2004 can be used in applications, including simulators and trainers for robotic medicine. Wearable device 2004 typically includes a stereoscopic display (providing separate images for each eye), stereo sound, and sensors like accelerometers and gyroscopes for tracking the pose of the user's head to match the orientation of the virtual camera with the user's eye positions in the real world. The user is typically a medical professional, e.g., a surgeon, a nurse, a surgeon's assistant, or a doctor. Wearable device 2004 can also have eye-tracking sensors and controllers. Wearable device 2004 can use head-tracking, which changes the field of vision as a surgeon turns their head.

Wearable device 2004 can include imagers, sensors, displays, feedback devices, controllers, or the like. The wearable device 2004 can capture data, locally analyze data, and provide output to the user based on the data. A controller of the wearable device 2004 can perform local computing (e.g., edge computing) with or without communicating with a remote server and can store edge computing ML libraries locally analyzing data to provide output. This allows onboard processing to be performed to avoid or limit the impact of, for example, network communications.

System 2000 can include one or more wearable devices configured to be worn on other parts of the body. The wearable devices can include, for example, gloves (e.g., haptic feedback gloves or motion-tracking gloves), wearable glasses, loops, heart monitors, heart rate monitors, or the like. These wearable devices can communicate with components of the system 2000 via wire connections, optical connections, wireless communications, etc. The wearable device 2004 can also communicate with external sensors and equipment. Example sensors and medical equipment is illustrated and described in more detail with reference to FIG. 1. The wearable device 2004 can receive data (sensor output, equipment output, operational information for instruments, etc.) and display the received information to the user. This allows the user to view sensor data without turning their attention away from a surgical site.

System 2000 can include a set of external displays 2005 (e.g., accessories of the wearable device 2004, desktop monitors, television screens, or other external displays), where the set of external displays 2005 may be provided instructions to display visual stimuli based on measurements or instructions provided by the wearable device 2004 or the server 2002. In some embodiments, the wearable device 2004 may communicate with various other electronic devices via a network 2050, where the network 2050 may include the Internet, a local area network, a peer-to-peer network, etc.

The wearable device 2004 may send and receive messages through the network 2050 to communicate with a server 2002, where the server 2002 may include one or more non-transitory storage media storing program instructions to perform one or more operations of a statistical predictor 2025. It should further be noted that while one or more operations are described herein as being performed by particular components of the system 2000, those operations may be performed by other components of the system 2000 in some embodiments. For example, operations described in this disclosure as being performed by the server 2002 may instead be performed by the wearable device 2004, where program code or data stored on the server 2002 may be stored on the wearable device 2004 or another client computer device instead. Similarly, in some embodiments, the server 2002 may store program code or perform operations described as being performed by the wearable device 2004. For example, the server may perform operations described as being performed by the projection module 2022, the display module 2023, or the feedback module 2024. Furthermore, although some embodiments are described herein with respect to ML models, other prediction models (e.g., a statistical model) may be used instead of or in addition to ML models. For example, a statistical model may be used to replace a neural network model in one or more embodiments. An example ML system 200 is illustrated and described in more detail with reference to FIG. 2.

In some embodiments, the system 2000 may present a set of stimuli (e.g., shapes, text, or images) on a display of the wearable device 2004. The wearable device 2004 may include a case 2043, a left transparent display 2041, and a right transparent display 2042, where light may be projected from emitters of the wearable device through waveguides of the transparent displays 2041-2042 to present stimuli viewable by an eye(s) of a user wearing the wearable device 2004. The wearable device 2004 also includes a set of outward-facing sensors 2047, where the set of outward-facing sensors 2047 may provide sensor data indicating the physical space around the wearable device 2004. In some embodiments, the set of outward-facing sensors 2047 may include cameras, infrared sensors, lidar sensors, radar sensors, etc. In some embodiments, the sensors 2047 can be inward-facing to monitor the user's state (e.g., level of stress, alertness level, etc.).

In some embodiments, the sensors 2047 can be cameras that capture images of the environment, patient, equipment, user, or the like. The captured images can be used to analyze steps being performed, a patient's state, and/or the surrounding environment. This allows the system 2000 to provide comprehensive analytics during procedures. For example, output from the sensors 2047 of the wearable device 2004 can be used to analyze the concentration/focus level of the user, alertness of the user, and stress level of the user (e.g., stress level calculated based on user metrics, such as heart rate, blood pressure, or breathing pattern), and other metrics. Surgical plans can be modified based on the collective metrics to enhance the performance of the user. In some embodiments, if the user becomes unable to maintain a threshold level of focus, the system 2000 can modify surgical plans such that critical steps are performed by another user, a robotic surgery system (such as the systems illustrated and described in more detail with reference to FIGS. 4A, 4B, 4C, 6, and 19), or using alternative techniques. This allows interoperative modification of surgical steps based on the user.

In some embodiments, sensors 2047 can track the wearer's eyes and provide feedback to the user to encourage the user to focus on targeted regions for visualization. This can help train the user to focus attention on regions or areas for each surgical step or action. The wearable device 2004 can receive and store operative plans, surgical data, and other information sufficient to allow one or more surgical steps to be performed with or without remote communications. This ensures that surgical steps can be completed if there is communication failure at the surgical suite.

In some procedures, the system 2000 can develop one or more training simulations for a user. The user can perform the simulations for manual procedures, robotically assisted procedures, or robotic procedures. The system 2000 can adaptively update the simulations based on desired procedure criteria, such as surgical time, predicted outcome, safety, outcome scores, or the like. This allows the system 2000 to develop surgical plans suitable for the procedures while training the user. In some embodiments, the wearable device 2004 can collect user input to synchronize the user's input with a surgical procedure. For example, the system 2000 can develop surgical plans with surgical steps for appropriate time periods based on threshold metrics. Example surgical plans are described in more detail with reference to FIG. 5. If the user becomes fatigued or tired, surgical steps can be shortened, reduced, or assigned to other users. Other users can use other wearable devices that are synchronized to communicate with the wearable device 1004 to provide coordinated operation between users.

In some embodiments, system 2000 receives a surgery type of the one or more surgical steps. A digital anatomical model is generated based on the surgery type. The digital anatomical model includes anatomical information associated with a portion of the anatomical features to be surgically altered during the one or more surgical steps. For example, system 2000 retrieves modeling parameters for generating the digital anatomical model based on the one or more surgical steps. The digital anatomical model is generated according to the modeling parameters. The modeling parameters can include, for example, one or more parametric modeling parameters, model properties (e.g., properties of tissue, fluids, thermal properties, etc.), fluid modeling parameters, mesh parameters (e.g., parameters for generating 3D meshes), kinematic parameters, boundary conditions, loading parameters, biomechanical parameters, fluid dynamic parameters, thermodynamic parameters, etc. The anatomical features are identified within the digital anatomical model. Anatomical characteristics are assigned to the identified anatomical features for viewing by the at least one user. The anatomical characteristics can include, for example, one or more anatomical feature statuses (e.g., unhealthy, normal, healthy), tissue properties, vitals for anatomical elements, sizes of anatomical features, etc.

In some embodiments, system 2000 retrieves modeling parameters for generating the digital anatomical model based on the one or more surgical steps. The digital anatomical model is generated according to the modeling parameters. The anatomical features are identified within the digital anatomical model. Anatomical characteristics are assigned to the identified anatomical features for viewing by the at least one user. For example, the modeling parameters define three-dimensional (3D) objects in an XR or AR environment that can be moved with a number of degrees of freedom (e.g., six degrees of freedom) using a controller (e.g., cursor). Modeling the identified anatomical features enables a user to experiment with perspective compared to traditional software or surgical practice.

The XR surgical simulation environment can include polygonal modeling, e.g., connecting points in 3D space (vertices) by line segments to form a polygonal mesh. For example, the XR surgical simulation environment includes textured polygonal meshes that are flexible and/or planar to approximate curved surfaces of simulation of surgical steps. In some embodiments, curve modeling (defining surfaces by curves that are influenced by weighted control points) is used. For example, performing the surgical steps virtually on the digital anatomical model uses digital sculpting (also known as sculpt modeling or 3D sculpting) to cut, push, pull, smooth, grab, pinch or otherwise manipulate virtual anatomical features as if they were made of real-life tissue or bone.

Generating the digital anatomical model is performed by developing a mathematical coordinate-based representation of different surfaces of the anatomical features in three dimensions by manipulating edges, vertices, and polygons in the simulated XR environment. The digital anatomical model represents the physical anatomy using a collection of points in 3D space, connected by different geometric entities such as lines and curved surfaces, etc. In embodiments, the digital anatomical model can be created by procedural modeling or scanning based on the imaging methods described in more detail with reference to FIG. 1. The digital anatomical model can also be represented as a 2D image using 3D rendering.

The AR mapping to the anatomy can include solid models that define a volume of the anatomical feature they represent, mapped using constructive solid geometry. In some embodiments, system 2000 receives information describing at least one surgical outcome for the one or more surgical steps. One or more correlations are determined between the anatomical mapping information and the at least one surgical outcome. A confidence-score AR mapping engine is updated based on the determination. The confidence-score AR mapping engine is configured to perform confidence-score AR mapping for other patients in new AR environments.

The anatomical mapping information can include shells or boundaries that represent surfaces of the anatomical features. The AR environment displayed to the at least one user can include polygonal meshes representing the physical anatomical features, subdivision surfaces, or level sets for deforming surfaces that can undergo topological changes. The AR mapping process can include transforming digital representations of the anatomical features into polygonal representations (polygon-based rendering) of the anatomical features overlaid on images of the physical anatomical features.

Furthermore, the system 2000 may present stimuli on the set of external displays 2005 during a visual testing operation. While the set of external displays 2005 is shown with two external displays, a set of external displays may include more or fewer external displays, such as only one external display or more than two external displays. For example, a set of external displays may include four external displays, eight external displays, nine external displays, or some other number of external displays. The external displays may include one or more types of electronic displays, such as computer monitors, smartphones, television screens, laptop devices, tablet devices, LED devices, LCD devices, and other types of electronic displays, etc. In some embodiments, the external display may include a projector, where the location of the external display may include a wall or screen onto which one or more stimuli is projected. In some embodiments, the external display may itself be transparent or partially transparent.

During or after a visual testing operation, the system 2000 may obtain feedback information related to the set of stimuli, where the feedback information may indicate whether or how an eye responds to one or more stimuli of the set of stimuli. For example, some embodiments may use the wearable device 2004 to collect feedback information that includes various eye-related characteristics. In some embodiments, the feedback information may include an indication of a response of an eye to the presentation of a dynamic stimulus at a first display location 2046 on a wearable device 2004. Alternatively, or in addition, the feedback information may include an indication of a lack of a response to such a stimulus. The response or lack of response may be determined based on one or more eye-related characteristics, such as an eye movement, a gaze direction, a distance in which an eye's gaze traveled in the gaze direction, a pupil size change, a user-specific input, etc. In some embodiments, the feedback information may include image data or results based on image data. For example, some embodiments may obtain an image or sequence of images (e.g., in the form of a video) of an eye captured during a testing operation as the eye responds to a stimulus.

In some embodiments, the system 2000 may track the ocular data of an eye and update associated ocular information based on feedback information indicating eye responses to stimuli. Some embodiments may use a prediction model to detect a non-responsive region of a visual field or another ocular issue of a visual field portion associated with the ocular data. In some embodiments, satisfying a set of vision criteria for a visual field location may include determining whether an eye responded to a stimulus presented at the display location mapped to the visual field location, where different presented stimuli may vary in brightness, color, shape, size, etc.

In some embodiments, the system 2000 can adjust viewing by the user based on the ocular information collected by the wearable device 2004. Any number of simulations can be performed to generate ocular information suitable for determining optimal settings for a user. The settings can change throughout the surgical procedure based on the surgical steps. For example, if the user becomes tired or fatigued, the system 2000 can adjust the visual field to stimulate the user, thereby increasing attentiveness. In some embodiments, the user can adjust the stimuli to his or her preferred preferences. Other responses can be collected and associated with the surgical procedure, specific surgical steps, or the like. Feedback scores can be generated to rank the collected set of stimuli. The score can be based on the time to complete action, biometric levels of the user (e.g., state of stress or heart rate), or other metrics.

In some embodiments, data used or updated by one or more operations described in this disclosure may be stored in a set of databases 2030. In some embodiments, the server 2002, the wearable device 2004, the set of external displays 2005, or other computer devices may access the set of databases to perform one or more operations described in this disclosure. For example, a prediction model used to determine ocular information may be obtained from a first database 2031, where the first database 2031 may be used to store prediction models or parameters of prediction models. Alternatively, or in addition, the set of databases 2030 may store feedback information collected by the wearable device 2004 or results determined from the feedback information. For example, a second database 2032 may be used to store a set of user profiles that include or link to feedback information corresponding with eye measurement data for the users identified by the set of user profiles. Alternatively, or in addition, the set of databases 2030 may store instructions indicating different types of testing procedures. For example, a third database 2033 may store a set of testing instructions that causes a first stimulus to be presented on the wearable device 2004, then causes a second stimulus to be presented on a first external display 2005*a*, and thereafter causes a third stimulus to be presented on a second external display 2005*b*.

In some embodiments, the projection module 2022 may generate a field-to-display map that maps a position or region of a visual field with a position or region of the set of external displays 2005 or of an AR interface displayed on the left transparent display 2041 or the right transparent display 2042. The field-to-display map may be stored in various forms, such as in the form of a set of multi-dimensional arrays, a function, a subroutine, etc. For example, the field-to-display map may include a first multi-dimensional array, where the first two dimensions of the first array may indicate a coordinate in a combined display space that maps 1:1 with a visual field. In some embodiments, a third dimension of the first array may identify which external display or wearable display to use when presenting a stimulus. Furthermore, a fourth and fifth dimension of the array may be used as coordinates relative to the origin of each respective external display. In some embodiments, an array or other set of numbers described in this disclosure may instead be divided into a plurality of arrays or other subsets of numbers. In some embodiments, the field-to-display map may be used in reverse, such that a display location may be mapped to a visual field location ("field location") using the field-to-display map. Some embodiments pre-generate a display-to-field map by inverting one or more of the arrays described above. Furthermore, some embodiments may use or update a map by using an array or other data structure of the map. Various other embodiments of the field-to-display map are possible, as described elsewhere in this disclosure.

In some embodiments, the projection module 2022 may obtain sensor information from the set of outward-facing sensors 2047, where the sensor information may include position measurements of the set of external displays 2005. For example, a user wearing the wearable device 2004 may rotate or translate their head, which may cause a corresponding rotation or translation of the wearable device 2004. Some embodiments may detect these changes in the physical orientation or position of the wearable device 2004 with respect to the set of external displays 2005. Some embodiments may then perform a mapping operation to determine the positions and orientations of the set of external displays based on the sensor information collected by the set of outward-facing sensors 2047.

In some embodiments, the projection module 2022 may update a field-to-display map that stores or otherwise indicates associations between field locations of a visual field and display locations of the left transparent display 2041, the right transparent display 2042, or the set of external displays 2005. For example, the set of outward-facing sensors 2047 may include one or more cameras to collect visual information from a surrounding area of the wearable device 2004, where the visual information may be used to determine a position or orientation of one or more devices of the set of external displays 2005. As the wearable device 2004 is moved, some embodiments may continuously obtain sensor information indicating changes to the external environment, including changes in the position or orientation of the set of external displays 2005 relative to the position or orientation of the wearable device 2004. For example, some embodiments may generate a point cloud representing the surfaces of objects around the wearable device 2004 and determine the positions and orientations of the set of external displays 2005 relative to the wearable device 2004 based on the point cloud. Furthermore, some embodiments may continuously update the field-to-display map as new sensor information is collected by the set of outward-facing sensors 2047.

In some embodiments, the display module 2023 may present a set of stimuli on the wearable device 2004 or the set of external displays 2005. In some embodiments, the left transparent display 2041 and right transparent display 2042 may be positioned with respect to the case 2043 to fit an orbital area on a user such that each display of the transparent displays 2041-2042 is able to collect data and present stimuli or other images to the user. The left transparent display 2041 and right transparent display 2042 may contain or be associated with an electronic display configured to present re-created images to an eye viewing the respective transparent display. In various embodiments, electronic display may include a projector, display screen, and/or hardware to present an image viewable by the eye. In some embodiments, a projector of an electronic monitor may be positioned to project images onto an eye of the subject or onto or through a screen, glass, waveguide, or other material. For example, the display module 2023 may cause a fixation point or another visual stimulus to be projected onto the first display location 2046, where the fixation point at the first display location 2046 may then be viewed by an eye of a user wearing the wearable device 2004.

In some embodiments, the display module 2023 may cause a set of stimuli to be displayed onto electronic displays other than the displays of the other external displays, such as an external display of the set of the external displays 2005. For example, after presenting a stimulus on a display of the wearable device 2004, the display module 2023 may cause a stimulus to be presented on the second external display 2005*b* at a second display location 2051. As used in this disclosure, an external display location may include a display location on an external display. The display module 2023 may then proceed to display additional stimuli on an additional location of the first external display 2005*a*, the wearable device 2004, or the second external display 2005*b*.

Some embodiments may determine the display location for a stimulus by first determining the location or region of a visual field. After determining the location or region of the visual field, some embodiments may then use a field-to-display map to determine which display location of the left transparent display 2041, the right transparent display 2042, or the set of external displays 2005 to use when displaying a stimulus. For example, some embodiments may determine that a previous sequence of sensor measurements indicated that a first region of a visual field has not yet been tested and select this first region for testing. Some embodiments may then use the field-to-display map to determine a third display location 2052 on the first external display 2005*a* and, in response to selecting the third display location 2052, display a stimulus at the third display location 2052. As described elsewhere in this disclosure, some embodiments may measure eye movements or otherwise measure responses of an eye to the stimuli presented on the set of external displays 2005 to measure a visual field of the eye. Furthermore, as described in this disclosure, a visual field location of a stimulus may include the field location mapped to or otherwise associated with the display location of the stimulus, where the mapping or association between the display and the field location is determined by a field-to-display map. Similarly, as used in this disclosure, a gaze location that is located at a field location may also be described as being located at a display location mapped to the field location.

In some embodiments, the feedback module 2024 may record feedback information indicating eye responses to the set of stimuli presented on the wearable device 2004 or the set of external displays 2005. In some embodiments, the transparent displays 2041-2042 may include a left inward-directed sensor 2044 and a right inward-directed sensor 2045, where the inward-directed sensors 2044-2045 may include eye-tracking sensors. The inward-directed sensors 2044-2045 may include cameras, infrared cameras, photodetectors, infrared sensors, etc. For example, the inward-directed sensors 2044-2045 may include cameras configured to track pupil movement and determine and track the visual axes of the subject. In some embodiments, the inward-directed sensors 2044-2045 may include infrared cameras and be positioned in lower portions relative to the transparent displays 2041-2042. The inward-directed sensors 2044-2045 may be directionally aligned to point toward a presumed pupil region for line-of-sight tracking or pupil tracking.

In some embodiments, the feedback module 2024 may use the inward-directed sensors 2044-2045 to collect feedback information indicating eye motion as an eye responds to different stimuli. For example, the feedback module 2024 may retrieve feedback information of an eye collected by the inward-directed sensors 2044-2045 as the eye responds to the presentation of a stimulus at the first display location 2046 and the second display location 2051. By collecting feedback information while stimuli are presented on both the wearable device 2004 and one or more devices of the set of external displays 2005, some embodiments may increase the boundaries of a visual field for which ocular data may be detected.

In some embodiments, the statistical predictor 2025 may retrieve stimuli information, such as stimuli locations and characteristics of the stimuli locations, where the stimuli locations may include locations on the set of external displays 2005. The statistical predictor 2025 may also retrieve training outputs indicative of the presence or absence of ocular responses or other outputs of a prediction model. The statistical predictor 2025 may then provide the set of stimuli information and training outputs to a ML model to update the parameters of the ML model to predict ocular responses based on new inputs. An example ML system 200 is illustrated and described in more detail with reference to FIG. 2. Alternatively, or in addition, the statistical predictor 2025 may use statistical models or rules to determine ocular responses and generate a visual field map representing a visual field of an eye, where one or more regions of the visual field map may be associated with a set of ocular responses or otherwise include ocular response information.

Figure 21:
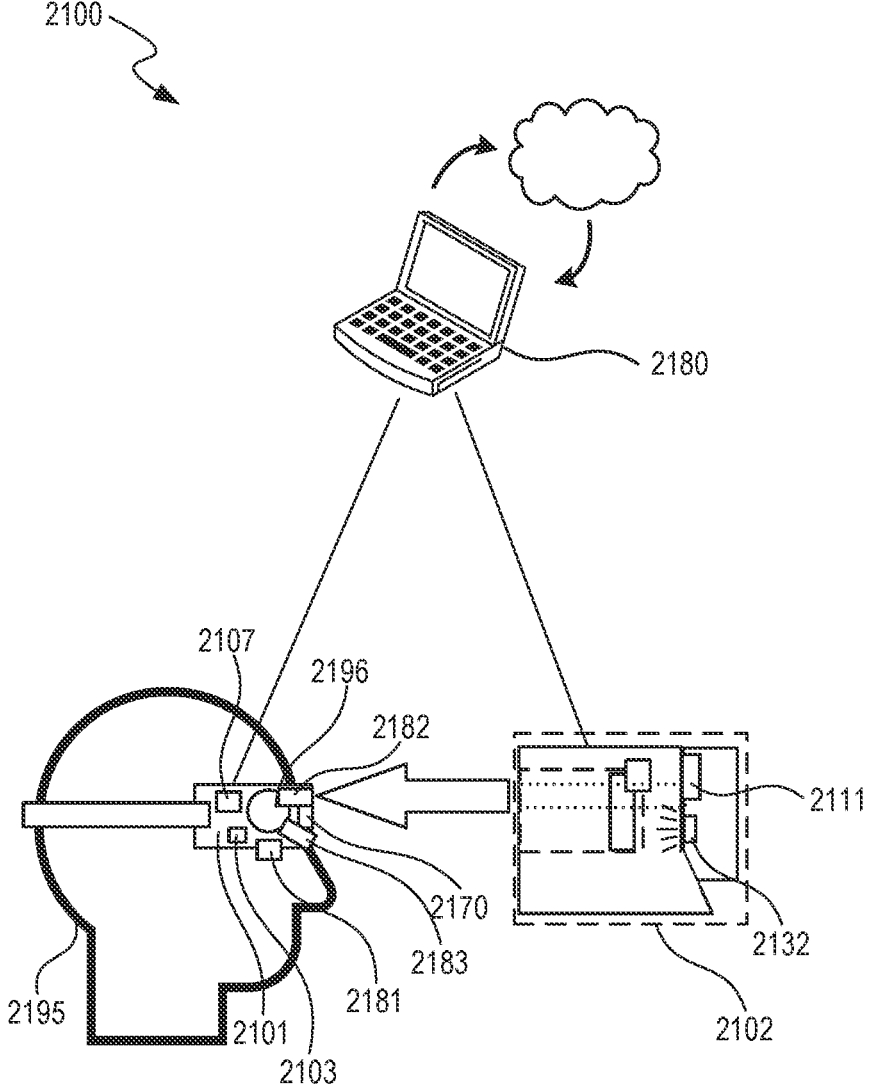
FIG. 21 illustrates an XR head mounted display (HMD) for facilitating robotic medicine, in accordance with one or more embodiments.

FIG. 21 illustrates an XR HMD 2101 for facilitating robotic medicine, in accordance with one or more embodiments. HMD 2101 can be, for example, an augmented reality device worn by a user while the user views a surgical environment. Information can be displayed at selected locations to avoid obstructing the viewing of targeted areas. Medical professional 2195 can wear HMD 2101, which can include a computing device 2107. Computing device 2107 can include a processor, microprocessor, controller, or other circuitry. In some embodiments, an eye 2196 of the medical professional may be capable of viewing images and video in XR from the operating room 2102 through lenses 2170 of the HMD 2101. The HMD 2101 may include an interior-facing camera to capture eye-related information and a set of exterior-facing cameras that include an exterior-facing camera 2182.

In some embodiments, a user initiates an XR session using computing system 2180 that is in communication with the HMD 2101. Computing system 2180 may include a stand-alone computer capable of operating without connecting to another computing device outside of a local network. Alternatively, or in addition, the computing system 2180 may include a computing system that receives program instructions or required data from an external data source not available through a local network.

In some embodiments, the computing system 2180 may initiate an XR session. Computing system 2180 may communicate with the HMD 2101 via a wireless connection or wired connection. For example, the computing system 2180 may send a wireless message to the computing device 2107 to initiate an XR session. For example, the computing system 2180 may send a command to the HMD 2101 via a Bluetooth® connection, where the command may cause the HMD 2101 to activate.

In some embodiments, the computing system 2180 may communicate with both the HMD 2101 to perform one or more operations. For example, the HMD 2101 may present an initial set of instructions to a medical professional 2195 and request a response from the medical professional 2195. After the medical professional 2195 provides a requested response (e.g., pressing a button, making a statement, etc.), the computing system 2180 may send a first set of instructions to the HMD 2101 to calibrate readings to more accurately measure eye-related data associated with the eye 2196. After the HMD 2101 sends a message to the computing system 2180 that calibration operations have been completed, the computing system 2180 may send further instructions to the HMD 2101. The computing system 2180 may determine the position of a fixation point based on eye-related readings and send a message to the HMD 2101 that causes the HMD 2101 to display a visual stimulus at the fixation point on the lenses 2170. After receiving a message from the HMD 2101 that the eye 2196 has set its gaze at the fixation point, the computing system 2180 may continue the XR session.

In some embodiments, an application executed by the computing device 2107 of the HMD 2101 may be used to control operations of components of the HMD 2101 or other electronic components. For example, the application executed by computing device 2107 may begin a visual test program and send a wireless message to a circuitry of the system 2180 using a wireless headset communication subsystem 2103. The wireless message may be based on one of various types of communication standards, such as a Bluetooth® standard, a Wi-Fi Direct standard, a NFC standard, a ZigBee® standard, a 6LoWPAN standard, etc.

In some embodiments, an application being executed by the computing device 2107 may retrieve data from the interior-facing camera 2183 and send instructions to control medical equipment based on this data. For example, the computing device 2107 may execute an application to perform a Viola-Jones object detection framework to detect an eye in a set of images using a boosted feature classifier based on video data provided by the interior-facing camera 2183. Furthermore, the application executed by the computing device 2107 may permit additional sensor data to trigger equipment in the operating room 2102, such as by receiving voice instructions captured from a microphone 2181, motion detected by the exterior-facing camera 2182, feeling a set of touches on the body of the HMD 2101, etc.

In some embodiments, a testing application executed by the computing device 2107 detects that a gaze location of medical professional 2195 is focused on a target user interface (UI) element or a target direction based on data collected by interior-facing camera 2183. For example, HMD 2101 displays a set of instructions that causes medical professional 2195 to look at a target UI location. In some embodiments, the target UI location is represented by a target region associated with the target UI location, such that a gaze location determined to be within the target region is considered to be focused on the target UI location. In response to a determination that the gaze location of eye 2196 is focused on the target UI location based on images provided by the interior-facing camera 2183, the application can activate medical equipment 2132. Furthermore, the application can send a message to robotic surgical system 2111 to turn off medical equipment 2132 based on a determination that the target UI location is no longer a focus of the user's gaze. Robotic surgical system 2111 is the same as or similar to robotic surgical system 160 illustrated and described in more detail with reference to FIG. 21. Alternatively, some embodiments may forego waiting for the medical professional 2195 to focus on a particular UI location or a particular direction before activating the medical equipment 2132.

In additional embodiments, a computer system obtains patient data of a patient. A user-mapping program is used to train an intra-operative AR mapping platform based on the obtained patient data. For example, the user-mapping program is configured to receive user input for the identification of individual anatomical features. One or more anatomical features of the patient associated with a surgical plan are identified for the patient based on the obtained patient data. The computer system performs an intra-operative AR mapping of the identified one or more anatomical features using the trained intra-operative AR mapping platform. Via an AR device, the intra-operative AR mapping is displayed to be viewed by a user.

In some embodiments, performing the intra-operative AR mapping includes obtaining a surgical plan and determining one or more anatomical features to be identified based on a surgical step of the surgical plan. The one or more anatomical features are identified. The one or more anatomical features and associated information for the surgical step are labeled. For example, one or more unidentifiable anatomical features of the patient are marked. The surgical plan is modified based on the determination of the one or more unidentifiable anatomical features. In some embodiments, an autonomous mapping platform is used to perform the intra-operative AR mapping. The autonomous mapping platform is trained by multiple users inputting anatomical data for reference patient images and validated for autonomously mapping a set of anatomical features associated with a surgery.

In some embodiments, a computer system selects one or more candidate features of a virtual anatomical model displayed in a VR environment displayed to a user. For example, the candidate features can be vascular vessels, nerves, or organ names. User input is received for the selected one or more candidate features. The computer system determines whether the user input for one or more candidate features reaches a threshold confidence score. In response to the user input reaching the threshold confidence score, the user input is identified as accurately labeling the one or more candidate features. In some embodiments, a computer system stores the user input as reference label data for the corresponding one or more candidate features. For example, the user input includes a label for each one of the respective one or more candidate features. The one or more candidate features can be unknown anatomical features, and the user input identifies the unknown features.

In some embodiments, determining whether the user input for one or more candidate features reaches the threshold confidence score is based on a comparison reference user input for similar candidate features. For example, the user input is used to train a ML model. For each of the candidate features, the user input can include at least one of a name of the candidate feature, a tissue type of the candidate feature, or user annotation. For example, a tissue type can be bone, nerve tissue, or soft tissue. The user annotation can be physician notes.

Figure 22:
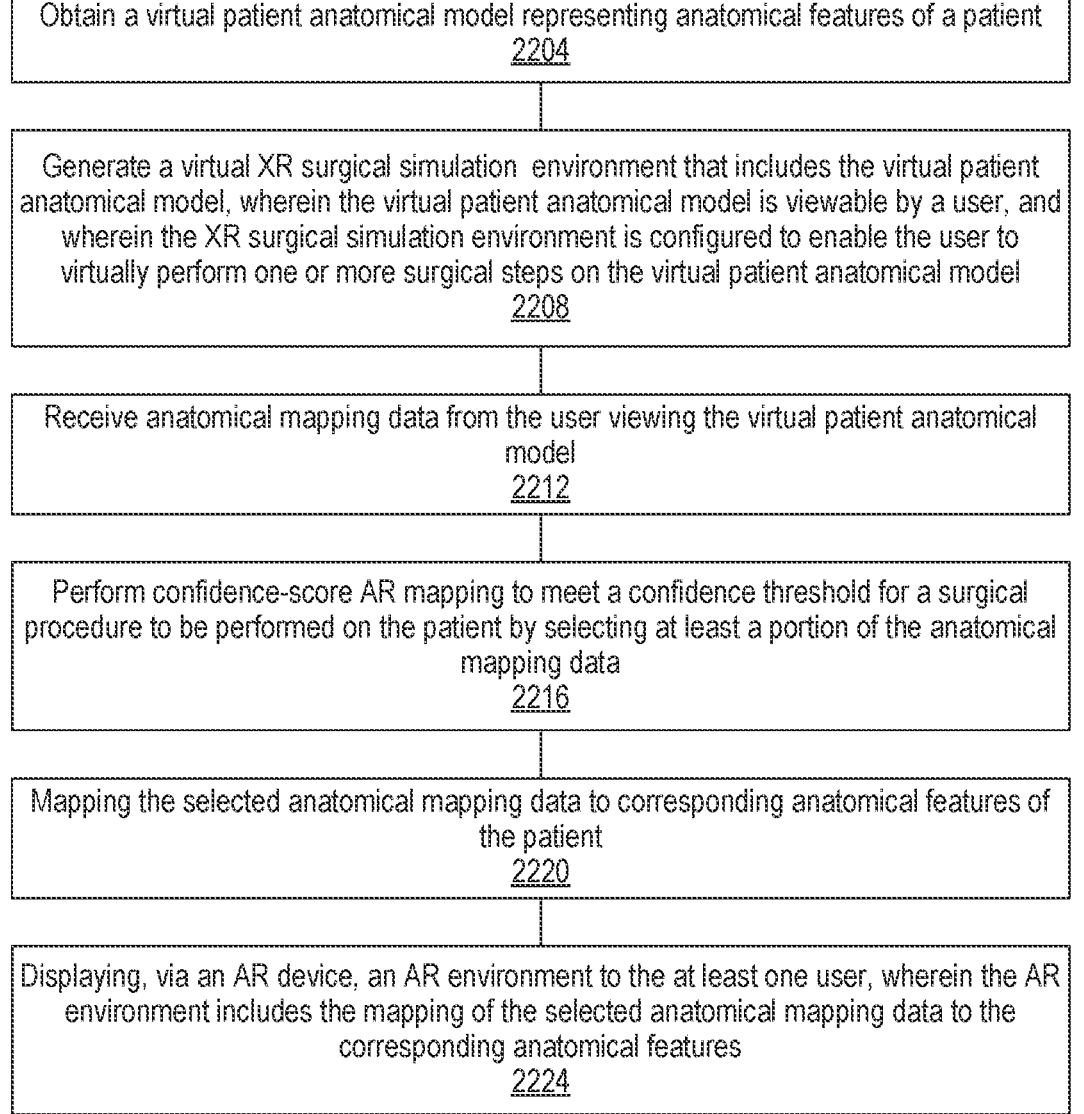
FIG. 22 is a flow diagram illustrating an extended reality (XR) process for facilitating robotic medicine, in accordance with one or more embodiments.

FIG. 22 is a flow diagram illustrating an XR process for facilitating robotic medicine, in accordance with one or more embodiments. The process can be performed by system 400 illustrated and described in more detail with reference to FIGS. 4A-C, system 600 illustrated in and described in more detail with reference to FIG. 6, system 1900 illustrated and described in more detail with reference to FIG. 19, system 2000 illustrated and described in more detail with reference to FIG. 20, the components illustrated and described in more detail with reference to FIG. 21, or the computer system 300 illustrated and described in more detail with reference to FIG. 3. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

In step 2204, a computer system performs an XR method by obtaining a digital anatomical model representing the anatomical features of a patient. The digital anatomical model is sometimes referred to as a virtual patient anatomical model or a digital twin. Digital twins are described in more detail with reference to FIG. 19. The digital anatomical model is generated using the imaging methods described in more detail with reference to FIG. 1 and the methods described in more detail with reference to FIG. 19.

In step 2208, the computer system generates an XR surgical simulation environment that includes the digital anatomical model. XR environments are described in more detail with reference to FIG. 19. The digital anatomical model is viewable by at least one user (e.g., a surgeon, a doctor, or another medical specialist) using an AR device, e.g., the devices illustrated and described in more detail with reference to FIGS. 20-21. The XR surgical simulation environment is configured to enable the at least one user to virtually perform one or more surgical steps on the digital anatomical model. Surgical simulation is described in more detail with reference to FIG. 20.

In step 2212, the computer system receives anatomical mapping information from the at least one user via the AR device. For example, a joystick, a keyboard, a touchscreen, or smart gloves are used to provide the input. The anatomical mapping information can include positions (e.g., coordinates), shapes, and sizes of anatomical systems, organs, and tissues. The anatomical mapping information can include the appearance and position of the various anatomical parts and their relationships with other parts. The anatomical mapping information can include macroscopic features, microscopic features, superficial anatomy or surface anatomy, etc.

In step 2216, the computer system performs confidence-score AR mapping to meet a confidence threshold for the one or more surgical steps to be performed on the anatomy of the patient by selecting at least a portion of the anatomical mapping information for the AR mapping to the anatomy. In some embodiments, fiducial markers, a global positioning system (GPS) unit, microelectromechanical systems (MEMS) sensors, such as digital compasses, accelerometers, or gyroscopes, are used to determine a confidence score for the mapping. The confidence score reflects the level of accuracy of the mapping from virtual anatomical features in the digital anatomical model to physical anatomical features of the patient. The confidence threshold can be, e.g., 90%, 95%, 99%, or 99.9%).

The confidence-score AR mapping is based on performing numerous XR/VR simulated procedures to identify/label anatomy to a sufficient level. The XR system would reach a threshold training level before it would be deployed autonomously by a surgeon. The confidence threshold can be procedure focused, e.g., higher for high-precision surgery (e.g., brain) or lower for low-precision surgery. For example, the confidence-score AR mapping is confidence-trained differently for different surgical platforms (e.g., cardiovascular, orthopedic, or brain). The confidence-score AR mapping can be confidence-trained differently for surgical steps performed by a surgical robot compared to surgical steps performed by a surgeon.

The confidence threshold can be physician or healthcare provider focused. For example, the confidence level is set by a user based on historical data. Such a confidence level enables greater customization. The confidence threshold can be surgical plan focused. For example, an analyzed surgical plan provides the confidence scores for an individual or for a series of surgical steps.

In some embodiments, the confidence-score AR mapping uses simultaneous localization and mapping (SLAM) markerless trackers, such as parallel tracking and mapping (PTAM), an Image Linked Map (ILM), or projection mapping. For example, the user can be enabled to touch physical objects in a process that provides passive haptic sensation to support both graphical visualization and passive haptic sensation.

In step 2220, the computer system maps the selected anatomical mapping information to the anatomical features of the patient. The mapping can be based on identifying anatomical features based on the size and configuration of the anatomical features, surrounding anatomical features, or the like. Anatomical feature detection routines, matching routines, ML algorithms, and other techniques can be used to isolate and then identify discrete anatomical features. In some embodiments, the confidence threshold (e.g., 90%, 95%, or 99%) is selected based on a surgery type of the one or more surgical steps. For example, the confidence threshold indicates at least one of a likelihood of a favorable outcome, a likelihood of completing the one or more surgical steps within a time period, or a likelihood of avoiding an intraoperative life-threatening adverse event (obtained from historical surgical patient outcomes). The user can input other confidence thresholds.

Image data of the patient is segmented to identify digital anatomical features associated with the surgery type. For example, the identification is performed using the ML system 200 of FIG. 2. The digital anatomical features are part of the digital anatomical model. Via a VR device, one or more anatomical identification prompts are generated for receiving the anatomical mapping information from the at least one user to label one or more discrete anatomical features viewed by the user. The surgery type can be a cardiovascular surgery, an orthopedic surgery, brain surgery, a joint replacement surgery, or an anatomical features repair surgery. The discrete anatomical features associated with the surgery type can be identified using one or more ML algorithms.

In some embodiments, the one or more anatomical identification prompts are displayed based on at least one of manipulation of the digital anatomical model or a zoom level of the digital anatomical model. For example, the digital anatomical model is regenerated based on the received anatomical mapping information. The one or more anatomical identification prompts are repeatedly displayed, and the regenerating is performed to obtain an amount of the anatomical mapping information for the confidence-score AR mapping that meets the confidence threshold. For example, the anatomical features are dynamically labeled based on at least one action performed by the at least one user within the AR environment. The anatomical elements displayed in the AR environment can be labeled based on the zoom level of the AR device.

In step 2224, the computer system displays, via the AR device, an AR environment to the at least one user. The AR environment includes the mapping of the selected anatomical mapping information to the anatomical features. In some embodiments, the computer system maps at least some of the anatomical features of the patient using a ML platform. The ML platform includes a plurality of surgery-type-specific ML modules to be applied to the image data of the patient to provide the anatomical surgery-type mapping. For example, each platform includes a different feature extraction module, a different ML model, and different training methods.

In some embodiments, the computer system receives a surgery type of the one or more surgical steps. A digital anatomical model is generated based on the surgery type. The digital anatomical model includes anatomical information associated with a portion of the anatomical features to be surgically altered during the one or more surgical steps. For example, the computer system retrieves modeling parameters for generating the digital anatomical model based on the one or more surgical steps. The digital anatomical model is generated according to the modeling parameters. The anatomical features are identified within the digital anatomical model. Anatomical characteristics are assigned to the identified anatomical features for viewing by the at least one user.

In some embodiments, the computer system identifies known anatomical features in the digital anatomical model, e.g., using vision processing, object recognition, and ML. Unidentifiable anatomical features are marked and collected from the digital anatomical model. The computer system determines whether one or more of the unidentifiable anatomical features are associated with the one or more surgical steps based on a surgical plan for the one or more surgical steps. Example surgical plans are described in more detail with reference to FIG. 5. At least one of the unidentifiable anatomical features are visually indicated within the digital anatomical model for identification by the user.

In some embodiments, the computer system determines to perform one or more surgical steps on the anatomy of the patient based on the known anatomical features. The known anatomical features enable AR mapping of a portion of the anatomical features to be surgically altered during the one or more surgical steps according to a surgical plan. In response to determining to perform one or more surgical steps, a notification to perform the one or more surgical steps on the anatomy of the patient is sent to a surgical robot, e.g., the surgical robot illustrated and described in more detail with reference to FIGS. 4A-C.

Figure 23:
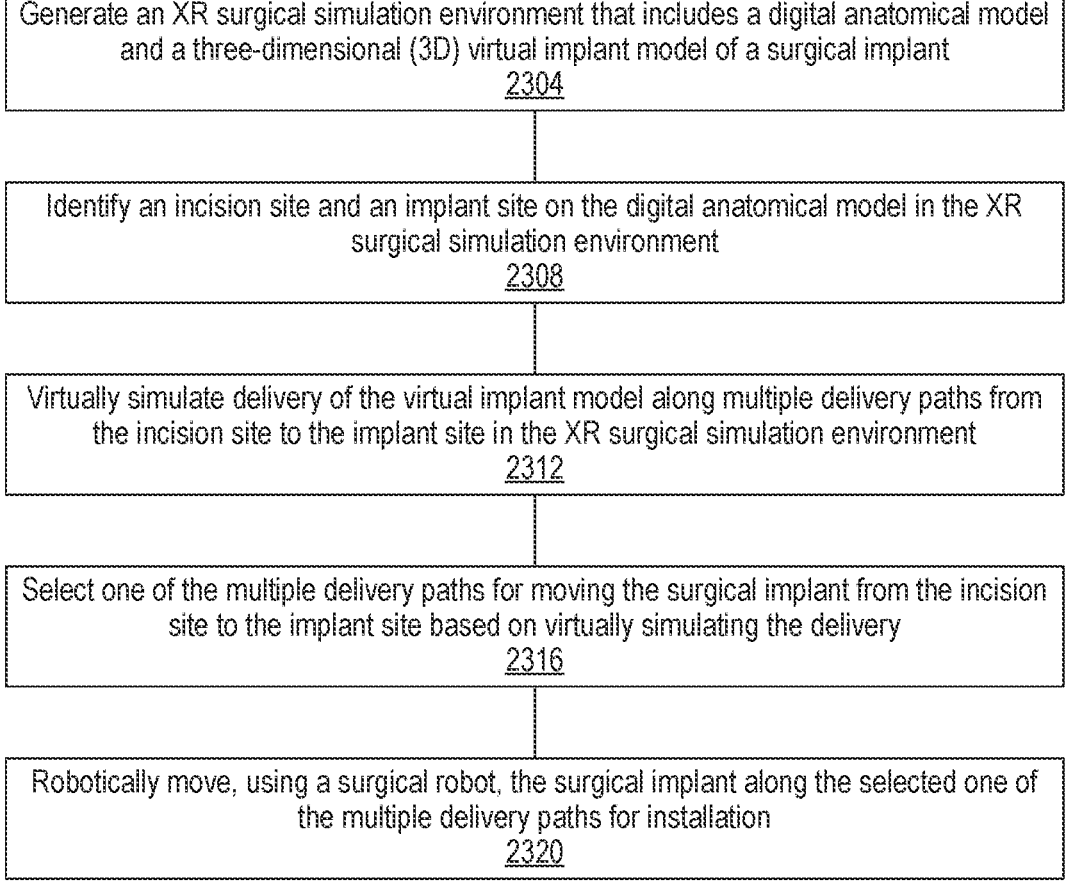
FIG. 23 is a flow diagram illustrating an example process for facilitating robotic surgical implant installation, in accordance with one or more embodiments.

FIG. 23 is a flow diagram illustrating an example process for facilitating robotic surgical implant installation, in accordance with one or more embodiments. The process can be performed by system 400 illustrated and described in more detail with reference to FIGS. 4A-C, system 600 illustrated and described in more detail with reference to FIG. 6, system 1900 illustrated and described in more detail with reference to FIG. 19, system 2000 illustrated and described in more detail with reference to FIG. 20, the components illustrated and described in more detail with reference to FIG. 21, or the computer system 300 illustrated and described in more detail with reference to FIG. 3. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

In act 2304, a computer system performs a computer-implemented method by generating an XR surgical simulation environment that includes a digital anatomical model and a three-dimensional (3D) virtual implant model of a surgical implant. XR environments are described in more detail with reference to FIG. 19. The XR surgical simulation environment can be viewable by at least one user (e.g., a surgeon, a doctor, or another medical specialist) using an AR device, e.g., the devices illustrated and described in more detail with reference to FIGS. 20-22. The digital anatomical model can represent the anatomical features of a patient. The digital anatomical model is sometimes referred to as a virtual patient anatomical model or a digital twin herein. Digital twins are described in more detail with reference to FIG. 19. In some embodiments, the digital anatomical model is generated using one or more images of a patient. The 3D virtual implant model of a surgical implant can be generated using stored implant designs or completely customized implants to meet the physiology or needs of the patient as described in more detail with reference to FIGS. 6 and 11. In some embodiments, the 3D virtual implant model can be segmented into a plurality of implant components. The segmentation of implant components is described in more detail with reference to FIG. 11. The digital anatomical model and the 3D virtual model can be generated using the imaging methods described in more detail with reference to FIG. 1 and the methods described in more detail with reference to FIG. 19.

In act 2308, a route planning module of the computer system identifies incision sites on the digital anatomical model in the XR surgical simulation environment. As described in more detail with reference to FIGS. 12 and 19, an incision site is a location through which at least some virtual tools, equipment, implant components, etc., will enter the digital anatomical model or the digital twin of the patient in the XR surgical simulation environment. The incision site can refer to the point at which the virtual implant or implant component enters the patient's body on the digital anatomical model or the digital twin in the XR surgical simulation environment. A combination of digital image segmentation, representation, and numerical description can be employed and validated on the digital anatomical model. For example, the ML model 216 (see FIG. 2) can be used for exploration of digital anatomical model, e.g., obtained from a Computed Tomography (CT) or Magnetic Resonance Imaging (MRI) scanner to identify an incision site and an implant site for surgical planning. Though the examples provided may refer to and utilize a single incision site, such reference should not be construed as a limitation, as multiple incision sites can be used. Similarly, the 3D virtual model of the implant or the implant components can be inserted through any number of incision sites in any combination in the XR surgical simulation environment.

In act 2312, the route planning module of the computer system generates multiple delivery paths from the incision site to the implant site in the XR surgical simulation environment. The multiple routes can be used for virtual delivery of the virtual implant model in the digital anatomical model or digital twin. Multiple routes can exist from the same incision site to the implant site in the digital anatomical model. The multiple routes are also possible paths along which a virtual tool and/or the virtual implant model can be navigated through the digital anatomical model and/or digital twin. The routes can direct virtual tools and/or the virtual implant model along different paths around anatomical structures.

In act 2316, the computer system selects one of the multiple delivery paths for moving the surgical implant from the incision site to the implant site based on virtually simulating the delivery. Based on the generated multiple delivery paths, the computer system determines at least one surgical movement modality for the virtual surgical implant in the XR surgical simulation environment. Movement of the surgical implant model using the at least one surgical movement modality through the identified routes is simulated. For each route, virtual simulations may be performed such that the virtual implant model is inserted into the anatomy through the virtual incision site and passed along the identified route. The virtual implant model may then be virtually installed at the virtual implant site. In some embodiments, virtual simulations may be performed for assembly of one or more virtual implant components, such that the virtual implant components are delivered virtually along the simulated path, assembled into the virtual implant model, and installed. If the virtual implant model is able to navigate from the virtual incision site to the virtual implant site and can be installed, the computer system may manufacture the surgical implant according to the implant design or three-dimensional virtual implant model, as described in more detail with reference to FIG. 6. Additionally or alternatively as described in FIG. 6, if the virtual implant model is able to navigate from the incision site to the implant site and can be installed in the digital anatomical model, the route is added to a list of verified routes.

In some embodiments, route constraints can be used to select one of the multiple delivery paths. For example, the computer system can determine the route constraints for the passage of the virtual implant model from the incision site to the implant site based on the size and shape of the virtual implant model. The virtual implant model can include the physical dimensions of the implant and the margins required to safely install the implant at the implant site, which can include varying margins depending on the type of tissues in proximity to the implant as it travels along the delivery route. For example, a virtual implant model can be allowed to be within 0.1 cm of a bone of the digital anatomical model, but no less than 0.5 cm from nerves or blood vessels of the digital anatomical model. The virtual implant model and constraints can additionally include deployment of a collapsed implant and the space required for expansion and activation of expansion at the implant site. The virtual implant model and constraints of the model can also include the flexibility of the implant at the implant site and amount of flex. The route with generally the highest scored route constraints for safely installing the virtual implant model at the implant site is chosen. In some embodiments, one or more routes can have equivalent scored route constraints and a user can manually select a route. As described in more detail with reference to FIG. 12, the routes evaluated for route constraints are called compliant routes. The complaint routes are routes that are able to accommodate the virtual implant model including the implants physical dimensions, flexibility or rigidity, and the location of anatomical structures in the digital anatomical model.

In some embodiments, the computer system may determine a predicted patient outcome based on the virtual simulations. The virtual simulations can be scored for a success rate, a risk of damage to the patient, a healing outcome, or other metric. In some embodiments, the route or delivery path may be selected based on the virtual simulation or the score for the predicted patient outcome, as described in more detail with reference to FIG. 6.

In act 2320, the computer system robotically moves, using a surgical robot, the surgical implant along the selected one of the multiple delivery paths for installation in the patient. The system identifies at least one route through which the surgical implant can be navigated from the incision site to the implant site using the surgical movement modality. The surgical robot performs the installation of the surgical implant at the surgical implant site based on the computer instructions and the virtually simulated route.

In some embodiments, surgical actions performed by a user on the digital anatomical model or digital twin using the XR environment are identified. A surgical workflow is generated for the surgical robot based on the surgical actions. The surgical workflow comprises workflow objects for the surgical procedure based on the surgical actions, and the surgical robot performs the surgical actions on the patient using the surgical workflow. As described in more detail with reference to FIG. 19, the surgical workflow can be adjusted based on a comparison to stored historical workflow.

The functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

The description and drawings herein are illustrative and are not to be construed as limiting. Numerous specific details are described to provide a thorough understanding of the disclosure. However, in certain instances, well-known details are not described in order to avoid obscuring the description. Further, various modifications can be made without deviating from the scope of the embodiments.

The terms used in this specification generally have their ordinary meanings in the art, within the context of the disclosure, and in the specific context where each term is used. Certain terms that are used to describe the disclosure are discussed above, or elsewhere in the specification, to provide additional guidance to the practitioner regarding the description of the disclosure. For convenience, certain terms can be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. One will recognize that "memory" is one form of a "storage" and that the terms can on occasion be used interchangeably.

Consequently, alternative language and synonyms can be used for any one or more of the terms discussed herein, and no special significance is to be placed upon whether or not a term is elaborated or discussed herein. Synonyms for certain terms are provided. A recital of one or more synonyms does not exclude the use of other synonyms. The use of examples anywhere in this specification, including examples of any term discussed herein, is illustrative only and is not intended to further limit the scope and meaning of the disclosure or of any exemplified term. Likewise, the disclosure is not limited to various embodiments given in this specification.

It is to be understood that the embodiments and variations shown and described herein are merely illustrative of the principles of this invention and that various modifications can be implemented by those skilled in the art.

We claim:

1. A computer-implemented method comprising:
generating an extended reality (XR) surgical simulation environment that includes a digital anatomical model and a three-dimensional (3D) virtual implant model of a surgical implant;
identifying at least one incision site and an implant site on the digital anatomical model in the XR surgical simulation environment;
simulating delivery of virtual components of the virtual implant model using a virtual surgical robot under control of a user, wherein the delivery of virtual components of the 3D virtual implant model are delivered, via the virtual surgical robot, along corresponding ones of multiple delivery paths in the digital anatomical model for delivery to the implant site in the digital anatomical model within the XR surgical simulation environment;
selecting a set of the multiple delivery paths for delivery of physical components of the surgical implant based on a simulated outcome score for the set of the multiple delivery paths being above a threshold;
robotically delivering, using a surgical robot, the physical components of the surgical implant using the set of the multiple delivery paths; and
robotically assembling the surgical implant using the physical components positioned in a patient.

2. The method of claim 1, wherein the XR surgical simulation environment is configured to enable at least one user to:
virtually perform one or more surgical steps associated with the delivery of the virtual implant components; and
view, using an XR device, the one or more surgical steps, the virtual implant model, and/or the digital anatomical model within the XR surgical simulation environment.

3. The method of claim 1, comprising:
retrieving modeling parameters for generating the digital anatomical model;
generating the digital anatomical model according to the modeling parameters;
identifying anatomical features within the digital anatomical model; and
assigning anatomical characteristics to the identified anatomical features for viewing.

4. The method of claim 1, comprising modifying the at least one incision site and the implant site based on simulating the delivery of the virtual components of the virtual implant model in the XR surgical simulation environment.

5. The method of claim 1, comprising:
for each delivery path,
predicting a patient outcome based on simulating the delivery of the virtual components of the virtual implant model to the implant site in the digital anatomical model within the XR surgical simulation environment; and
determining a score for the predicted patient outcome.

6. The method of claim 5, wherein one of the multiple delivery paths is selected based on at least one of simulating the delivery of the virtual components of the virtual implant model or the score for the predicted patient outcome.

7. The method of claim 5, comprising:
ranking scores for the predicted patient outcomes, wherein the scores for the predicted patient outcomes indicate at least one of:
a likelihood of a favorable outcome,
a likelihood of completing one or more surgical steps within a time period, or
a likelihood of avoiding an intraoperative life-threatening adverse event; and
using the ranking to select one of the multiple delivery paths.

8. A computer system comprising:
one or more computer processors; and
a non-transitory-computer-readable storage medium storing computer instructions, which when executed by the one or more computer processors cause the computer system to:
generate an extended reality (XR) surgical simulation environment that includes a digital anatomical model and a three-dimensional (3D) virtual implant model of a surgical implant;
identify at least one incision site and an implant site on the digital anatomical model in the XR surgical simulation environment;
simulate delivery of virtual components of the virtual implant model using a virtual surgical robot under control of a user, wherein the delivery of virtual components of the 3D virtual implant model are delivered, via the virtual surgical robot, along corresponding ones of multiple delivery paths in the digital anatomical model for delivery to the implant site in the digital anatomical model within the XR surgical simulation environment;
select a set of the multiple delivery paths for delivery of physical components of the surgical implant based on a simulated outcome score for the set of the multiple delivery paths being above a threshold; and
robotically deliver, using a surgical robot, the physical components of the surgical implant using the set of the multiple delivery paths; and
robotically assemble the surgical implant using the physical components positioned in a patient.

9. The computer system of claim 8, wherein the XR surgical simulation environment is configured to enable at least one user to:
virtually perform one or more surgical steps associated with the delivery of the virtual implant model; and
view, using an XR device, the one or more surgical steps, the virtual implant model, and/or the digital anatomical model within the XR surgical simulation environment.

10. The computer system of claim 8, wherein the computer instructions cause the computer system to:
retrieve modeling parameters for generating the digital anatomical model;

generate the digital anatomical model according to the modeling parameters;

identify anatomical features within the digital anatomical model; and assign anatomical characteristics to the identified anatomical features for viewing.

11. The computer system of claim 8, wherein the computer instructions cause the computer system to modify the at least one incision site and the implant site based on simulating the delivery of the virtual components of the virtual implant model in the XR surgical simulation environment.

12. The computer system of claim 8, wherein the computer instructions cause the computer system to:

for each delivery path, determine a predicted patient outcome based on simulating the delivery of the virtual components of the virtual implant model to the implant site in the digital anatomical model within the XR simulation environment; and determine a score for the predicted patient outcome.

13. The computer system of claim 12, wherein one of the multiple delivery paths is selected based on at least one of simulating the delivery of the virtual components of the virtual implant model or the score for the predicted patient outcome.

14. The computer system of claim 12, wherein the computer instructions cause the computer system to:

rank scores for predicted patient outcomes, wherein the scores for the predicted patient outcomes indicate at least one of:

a likelihood of a favorable outcome, a likelihood of completing one or more surgical steps within a time period, or a likelihood of avoiding an intraoperative life-threatening adverse event; and use the ranking to select one of the multiple delivery paths.

15. A non-transitory-computer-readable storage medium storing computer instructions, which when executed by one or more computer processors cause the one or more computer processors to:

generate an extended reality (XR) surgical simulation environment that includes a digital anatomical model and a three-dimensional (3D) virtual implant model of a surgical implant;

identify at least one incision site and an implant site on the digital anatomical model in the XR surgical simulation environment;

simulate delivery of virtual components of the virtual implant model using a virtual surgical robot under control of a user, wherein the delivery of virtual components of the 3D virtual implant model are delivered, via the virtual surgical robot, along corresponding ones of multiple delivery paths in the digital anatomical model for delivery to the implant site in the digital anatomical model within in the XR surgical simulation environment;

select a set of the multiple delivery paths for delivery of physical components of the surgical implant based on a simulated outcome score for the set of the multiple delivery paths being above a threshold; and robotically deliver, using a surgical robot, the physical components of the surgical implant using the set of the multiple delivery paths; and robotically assemble the surgical implant using the physical components positioned in a patient.

16. The non-transitory-computer-readable storage medium of claim 15, wherein the XR surgical simulation environment is configured to enable at least one user to:

virtually perform one or more surgical steps associated with the delivery of the virtual components; and view, using an XR device, the one or more surgical steps, the virtual implant model, and/or the digital anatomical model within the XR surgical simulation environment.

17. The non-transitory-computer-readable storage medium of claim 15, wherein the computer instructions cause the one or more computer processors to:

retrieve modeling parameters for generating the digital anatomical model;

generate the digital anatomical model according to the modeling parameters;

identify anatomical features within the digital anatomical model; and assign anatomical characteristics to the identified anatomical features for viewing.

18. The non-transitory-computer-readable storage medium of claim 15, wherein the computer instructions cause the one or more computer processors to modify the at least one incision site and the implant site based on simulating the delivery of the virtual components of the virtual implant model in the XR surgical simulation environment.

19. The non-transitory-computer-readable storage medium of claim 15, wherein the computer instructions cause the one or more computer processors to:

for each delivery path, determine a predicted patient outcome based on simulating the delivery of the virtual components of the virtual implant model to the implant site in the digital anatomical model within the XR surgical simulation environment; and determine a score for the predicted patient outcome.

20. The non-transitory-computer-readable storage medium of claim 19, wherein one of the multiple delivery paths is selected based on at least one of simulating the delivery of the virtual components of the virtual implant model or the score for the predicted patient outcome.

* * * * *